(12) United States Patent
Freitas, Jr. et al.

(10) Patent No.: US 10,138,172 B2
(45) Date of Patent: *Nov. 27, 2018

(54) METHODS, SYSTEMS AND WORKPIECES USING MECHANOSYNTHESIS

(71) Applicant: CBN Nano Technologies Inc., Ottawa OT (CA)

(72) Inventors: Robert A. Freitas, Jr., Pilot Hill, CA (US); Ralph C. Merkle, Cupertino, CA (US)

(73) Assignee: CBN Nano Technologies, Inc., Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/204,845

(22) Filed: Jul. 7, 2016

(65) Prior Publication Data
US 2018/0093930 A1    Apr. 5, 2018

Related U.S. Application Data

(60) Division of application No. 13/781,532, filed on Feb. 28, 2013, now abandoned, which is a continuation-in-part of application No. 13/187,523, filed on Jul. 21, 2011, now abandoned, which is a division of application No. 12/204,642, filed on Sep. 4, 2008, now Pat. No. 8,171,568.

(60) Provisional application No. 60/970,658, filed on Sep. 7, 2007.

(51) Int. Cl.
*B82B 3/00* (2006.01)
*C07B 61/00* (2006.01)
*B82Y 40/00* (2011.01)

(52) U.S. Cl.
CPC ............ *C07B 61/00* (2013.01); *B82B 3/0033* (2013.01); *B82Y 40/00* (2013.01)

(58) Field of Classification Search
CPC ................................ B82B 1/00; B82B 3/0009
See application file for complete search history.

(56) References Cited

U.S. PATENT DOCUMENTS

| | | | |
|---|---|---|---|
| 4,952,749 A | 8/1990 | Alexander et al. | |
| 4,987,312 A | 1/1991 | Eigler | |
| 5,144,148 A | 9/1992 | Eigler | |
| 5,372,659 A | 12/1994 | Lamaze et al. | |
| 5,411,797 A | 5/1995 | Davanloo et al. | |
| 5,824,470 A | 10/1998 | Baldeschwieler et al. | |
| 6,017,504 A | 1/2000 | Kaliaguine et al. | |
| 6,339,227 B1 | 1/2002 | Ellenbogen | |
| 6,348,700 B1 | 2/2002 | Ellenbogen et al. | |
| 6,422,077 B1 | 7/2002 | Krauss et al. | |
| 6,531,107 B1 | 3/2003 | Spencer et al. | |
| 6,716,409 B2 | 4/2004 | Hafner et al. | |
| 6,783,589 B2 | 8/2004 | Dahl | |
| 6,827,979 B2 | 12/2004 | Mirkin et al. | |
| 6,835,534 B2 | 12/2004 | Weiss et al. | |
| 6,864,481 B2 | 5/2005 | Kaito et al. | |
| 6,886,395 B2 | 5/2005 | Minne | |
| 6,987,277 B2 | 1/2006 | Baur et al. | |
| 7,049,374 B2 | 5/2006 | Liu et al. | |
| 7,189,455 B2 | 3/2007 | Wong et al. | |
| 7,211,795 B2 | 5/2007 | Collier et al. | |
| 7,282,710 B1 | 10/2007 | Black et al. | |
| 7,291,284 B2 | 11/2007 | Mirkin et al. | |
| 7,309,476 B2 | 12/2007 | Carlson et al. | |
| 7,312,562 B2 | 12/2007 | Dahl et al. | |
| 7,326,293 B2 | 2/2008 | Randall et al. | |
| 7,326,923 B2 | 2/2008 | Berstis | |
| 7,381,625 B2 | 6/2008 | Xi et al. | |
| 7,687,146 B1 | 3/2010 | Freitas | |
| 2009/0056802 A1 | 3/2009 | Rabani | |

OTHER PUBLICATIONS

Freitas et al. "Nanofactory Collaboration". Version as edited on Aug. 1, 2006. Retrieved from Internet Archive Wayback capture from Aug. 20, 2006. (Year: 2006).*
Freitas et al. "Introduction to Diamond Mechanosynthesis (DMS)". Version as edited Jul. 27, 2006. Retrieved from Internet Archive Wayback capture from Aug. 20, 2006. (Year: 2006).*
Freitas. "A simple tool for positional diamond mechanosynthesis, and its method of manufacture". Dated Jan. 12, 2004. (Year: 2004).*
Jingping Peng, Robert A. Freitas Jr., Ralph C. Merkle, James R. Van Ehr, John N. Randall, George D. Skidmore, "Theoretical Analysis of Diamond Mechanosynthesis. Part III. Positional C2 Deposition of Diamond C(110) Surface using Si/Ge/Sn-based Dimer Placement Tools," J. Comput. Theor. Nanosci. 3 (Feb. 2006):28-41.
Berhane Temelso, C. David Sherrill, Ralph C. Merkle, Robert A. Freitas Jr., "High-level Ab Initio Studies of Hydrogen Abstraction from Prototype Hydrocarbon Systems," J. Phys. Chem. A 110 (Sep. 28, 2006):11160-11173.
Berhane Temelso, C. David Sherrill, Ralph C. Merkle, Robert A. Freitas Jr., "Ab Initio Thermochemistry of the Hydrogenation of Hydrocarbon Radicals Using Silicon, Germanium, Tin and Lead Substituted Methane and Isobutane," J. Phys. Chem. A 111(Aug. 15, 2007):8677-8688.
K. Eric Drexler, Nanosystems: Molecular Machinery, Manufacturing, and Computation, John Wiley & Sons, New York, 1992, Chapter 8.
D.M. Eigler, E.K. Schweizer, "Positioning Single Atoms with a Scanning Tunnelling Microscope," Nature 344(Apr. 5, 1990):524-526.
Noriaki Oyabu, Oscar Custance, Insook Yi, Yasuhiro Sugawara, Seizo Morita, "Mechanical vertical manipulation of selected single atoms by soft nanoindentation using near contact atomic force microscopy," Phys. Rev. Lett. 90(May 2, 2003):176102.

(Continued)

*Primary Examiner* — Donald R Spamer

(57) ABSTRACT

Methods and systems for building three-dimensional workpieces are described using a plurality of mechanosynthetic reactions. These methods may employ engineered reliability in reactions and process conditions and may use simulated or otherwise vetted reaction sequences, to allow workpieces requiring many reactions to be built with acceptable reliability. These many reactions may be the repetition of one or a small number of reactions, or many diverse reactions, or a combination thereof.

18 Claims, 22 Drawing Sheets

(56) References Cited

OTHER PUBLICATIONS

Ralph C. Merkle, "A proposed 'metabolism' for a hydrocarbon assembler," Nanotechnology 8(1997):149-162.

M.C. Hersam, G.C. Abeln, J.W. Lyding, "An approach for efficiently locating and electrically contacting nanostructures fabricated via UHV-STM lithography on Si(100)," Microelectronic Engineering 47(Jun. 1999):235-237.

D.H. Huang, Y. Yamamoto, "Physical mechanism of hydrogen deposition from a scanning tunneling microscopy tip," Appl. Phys. A 64(Apr. 1997):R419-R422.

Morita, S., Sugimoto, Y., et al. (2004). "Atom-selective imaging and mechanical atom manipulation using the non-contact atomic force microscope." J. Electron Microsc. 53(2): 163-168.

J. Franks, "Preparation and properties of diamondlike carbon films," J. Vac. Sci. & Technol. A 7(May 1989):2307-2310.

C.A. Rego, P.W. May, E.C. Williamson, M.N.R. Ashfold, Q.S. Chia, K.N. Rosser, N.M. Everitt, "CVD diamond growth on germanium for infra-red window applications," Diam. Rel. Mater. 3(1994):939.

D.S. Patil, K. Ramachandran, N. Venkatramani, M. Pandey, R. d'Cunha, "Microwave plasma deposition of diamond-like carbon coatings," Pramana J. Phys. 55(Nov./Dec. 2000):933-939.

Y. Fukuda, M. Shimomura, G. Kaneda, N. Sanada, V.G. Zavodinsky, I.A. Kuyanov, E.N. Chukurov, "Scanning tunneling microscopy, high-resolution electron energy loss spectroscopy, and theoretical studies of trimethylphosphine (TMP) on a Si(111)-(7×7) surface," Surf. Sci. 442(1999):507-516.

M.J. Bronikowski, R.J. Hamers, "The chemistry of gallium deposition on Si(001) from trimethylgallium: an atomically resolved STM study," Surf. Sci. 348(Mar. 10, 1996):311-324.

D.M. Gruen, S. Liu, A. R. Krauss, X.Pan, "Buckyball microwave plasmas: Fragmentation and diamond-film growth," J. Appl. Phys. 75(1994):1758-1763.

Ansoon Kim, Jae Yeol Maeng, Jun Young Lee, Sehun Kim, "Adsorption configuration and thermal chemistry of acetylene on the Ge(100) surface," J. Chem. Phys. 117(Dec. 8, 2002):10215-10222.

Guangquan Lu, John E. Crowell, "The adsorption and thermal decomposition of digermane on Ge(111)," J. Chem. Phys. 98(Feb. 15, 1993):3415-3421.

N. Oyabu, O. Custance, M. Abe, S. Moritabe, "Mechanical Vertical Manipulation of Single Atoms on the Ge(111)-c (2×8) Surface by Noncontact Atomic Force Microscopy," Abstracts of Seventh International Conference on Non-Contact Atomic Force Microscopy, Seattle, Washington, USA, Sep. 12-15, 2004.

P.D. Nellist, M.F. Chisholm, N. Dellby, O.L. Krivanek, M.F. Murrill, Z.S. Szilagyi, A.R. Lupini, A. Borisevich, W.H. Sides, Jr., S.J. Pennycock, "Direct Sub-Angstrom Imaging of a Crystal Lattice," Science 305 (Sep. 17, 2004):1741.

G. Basile, P. Becker, A. Bergamin, G. Cavagnero, A. Franks, K. Jackson, U. Kuetgens, G. Mana, E.W. Palmer, C.J. Robbie, M. Stedman, J. Stumpel, A. Yacoot, G. Zosi, "Combined optical and X-ray interferometry for high-precision dimensional metrology", Proc. R. Soc. Lond. A (2000) 456, 701-729.

Y. Sugimoto, P. Pou, O. Custance, P. Jelinek, M. Abe, R. Perez, S. Morita, "Complex Patterning by Vertical Interchange Atom Manipulation Using Atomic Force Microscopy", Science 322, 413 (2008).

Artyukhov, V. I., "A six degree of freedom nanomanipulator design based on carbon nanotube bundles." Nanotechnology 21(38): 9 (2010).

Duwez, A., Cuenot, S., et al., "Mechanochemistry: targeted delivery of single molecules." Nature Nanotechnology 1(2): 122-125 (2010).

Ho W. and Lee, H., "Single bond formation and characterization with a scanning tunneling microscope." Science (286): 1719-1722 (2010).

Tarasov, D., Akberova, N., et al. (2010). "Optimal Tooltip Trajectories in a Hydrogen Abstraction Tool Recharge Reaction Sequence for Positionally Controlled Diamond Mechanosynthesis." J. Comput. Theor. Nanosci. 7(2): 325-353.

Yang, S. H., Kim, Y.-S., et al. (2012). "Microelectromechanical systems based Stewart platform with sub-nano resolution." Appl. Phys. Lett. 101(6): 5.

Johannes, M. S. (2006). "Automated CAD/CAM-based nanolithography using a custom atomic force microscope." IEEE Transactions on Automation Science and Engineering 3(3): 236-239.

Ramachandran, T., Baur, C., et al. (1998). "Direct and Controlled Manipulation of Nanometer-Sized Particles Using the Non-Contact Atomic Force Microscope." Nanotechnology(9): 237-245.

Tay, A. B. H. and Thong, J. T. L. (2004). "Fabrication of super-sharp nanowire atomic force microscope using a field emission induced growth technique." Review of Scientific Instruments 75(10).

Wong, S., Woolley, A., et al. (1999). "Functionalization of carbon nanotube AFM probes using tip-activated gases." Chemical Physics Letters(306): 219-225.

Hafner, J., Cheung, C., et al. (2001). "Structural and Functional Imaging with Carbon Nanotube AFM Probes." Progress in Biophysics & Molecular Biology 1(77): 73-110.

Chen, H. (2006). "CAD-guided automated nanoassembly using atomic force microscopy-based nonrobotics." IEEE Transactions on Automation Science and Engineering 3(3): 208-217.

Grandbois, M., Dettmann, W., et al. (2000). "Affinity Imaging of Red Blood Cells Using an Atomic Force Microscope." Journal of Histochemistry & Cytochemistry(48): 719-724.

\* cited by examiner

METHODS, SYSTEMS AND WORKPIECES USING MECHANOSYNTHESIS

CROSS-REFERENCE TO RELATED APPLICATIONS

This application is a divisional of pending application Ser. No. 13/781,532 filed 28 Feb. 2013, which application is a continuation-in-part of, and claims priority to, pending application Ser. No. 13/187,523, filed 21 Jul. 2011, which is a divisional application of, and claims the benefit of, U.S. Pat. No. 8,171,568, filed 4 Sep. 2008, which claims the benefit of U.S. Provisional Patent Application No. 60/970,658 filed 7 Sep. 2007. All of these applications and patents are incorporated herein by reference. Related applications which are continuations-in-part of U.S. Pat. No. 8,171,568 are Ser. No. 13/781,515 filed 2013 Feb. 28, Ser. No. 13/781,526 filed 2013 Feb. 28, Ser. No. 14/047,668 filed 2013 Oct. 7, Ser. No. 14/542,547 filed 2014 Nov. 15, and Ser. No. 15/050,067 filed 2016 Feb. 22. Issued patent which is a divisional of U.S. Pat. No. 8,171,568 is U.S. Pat. No. 8,276,211 and issued patent which is a continuation-in-part of U.S. Pat. No. 8,171,568 is U.S. Pat. No. 9,244,097.

FEDERALLY SPONSORED RESEARCH

Not applicable.

SEQUENCE LISTING OR PROGRAM

A CD containing data for molecular models in .hin format, containing 33 files totaling 814 KB, representing the molecular models shown in FIGS. 24-56, has been included with this application and is incorporated herein by reference.

FIELD OF INVENTION

The present application relates to mechanosynthesis, the fabrication of atomically precise tools and materials using individual atoms or small groups of atoms as the fundamental building blocks, and more particularly, to devices, methods and systems for performing ordered sequences of site-specific positionally controlled chemical reactions that are induced by use of mechanical force.

BACKGROUND OF THE INVENTION

Traditional Manufacturing Techniques Versus Mechanosynthesis.

The benefits of being able to manufacture with microscopic precision are well-known. For example, lithography is used to create the features on integrated circuits and may also be used to create MEMS (microelectromechanical systems) or NEMS (nano-electromechanical systems) devices. Smaller features on integrated circuits enable them to run faster and use less power, and MEMS and NEMS technologies are used to create devices as diverse as airbags and cell phones (e.g., accelerometers and attitude sensing), projection screens (e.g., digital light projection), and medical diagnostics (e.g., lab-on-a-chip devices).

However, even though such devices or the features on such devices may be microscopic, they are not atomically-precise nor are they of the scale of single atoms. For example, the feature size currently used for Intel Corporation's "Ivy Bridge" line of processors is 22 nanometers. This is over 100 times the diameter of a carbon atom, and about 200 times the diameter of a hydrogen atom.

Of course, the precision of lithography continues to be improved, and various other technologies are being pursued in an attempt to manufacturer ever-smaller features and devices. For example, self-assembly is aimed at using microscopic units with specific shapes and charges that essentially snap together to create tiny structures. But, self-assembly is limited in the structures that can be created by the need to design around the shape and charge requirements of the individual units.

Many other techniques for the creation of microscopic features and devices also exist. For example, e-beam deposition, micro-machining, and selective etching can all be used to create microscopic features. However, none of these techniques can provide atomic accuracy while manufacturing devices with diverse functions, out of a wide range of materials.

Mechanosynthesis offers the ability to create atomically-precise structures out of a wide variety of atoms or molecules, while being relatively unconstrained in the shapes and properties of the devices which can be built. This offers great benefit to numerous industries not only because it allows the construction of parts and devices which cannot be manufactured through other means, but even with respect to bulk materials which can be manufactured through other means, the materials manufactured via mechanosynthesis, due to their atomic precision, can have properties superior to the same materials manufactured by conventional means.

Mechanosynthesis and Mechanosynthesis Terminology.

The present invention describes methods, systems and products relating to the manufacture of atomically-precise structures using atoms as raw material. These atoms are referred to as feedstock. The structures are referred to as workpieces. Workpieces are built using positionally-controlled tips, such as the tips on Atomic Force Microscopes, to move feedstock atoms into desired locations on a workpiece. Mechanical force is applied to atoms via these tips to make and break chemical bonds. This mechanical making or breaking of bonds at specific locations is called mechanosynthesis.

The order in which atoms are added to, or removed from, a workpiece is referred to as a build sequence or reaction sequence. A build sequence also encompasses the concept of a trajectory, which is the path along which an atom moves during a mechanosynthetic reaction. By using tips to move feedstock along a trajectory, to a specific location with respect to a workpiece, and then applying mechanical force to bond the atom into position, devices can be manufactured where the position of every atom is known.

Tips Used in Mechanosynthesis.

The mechanosynthesis processes described herein use a variety of ultra-sharp tips designed to move atoms with sub-angstrom precision and to facilitate different reactions with those atoms. The tips may be, but do not have to be, atomically-precise. While some embodiments of the invention use atomically-precise tips, others do not. For example, a bootstrap sequence is presented herein which allows the creation of atomically-precise tips using non-atomically-precise tips.

Atomically imprecise, but ultra-sharp tips, also called probes, are available commercially (e.g., from Nanotools Gmbh, Munich, Germany, or from NANOSENSORS, Neuchatel, Switzerland), or can be made using electron-beam induced deposition (EBID), among others techniques. Tay, A. B. H. and Thong, J. T. L. (2004) "Fabrication of super-sharp nanowire atomic force microscope using a field emission induced growth technique." Review of Scientific Instruments 75(10). Such tips can serve as a starting point for the bootstrap process described herein.

In general, the important characteristic of a tip is that it reliably performs the desired mechanosynthetic reaction. Atomic precision is a helpful characteristic of tips for mechanosynthesis because knowing the precise placement of atoms on the tip allows design of reliable reactions via computational chemistry simulations. This is not to say that atomically imprecise tips could not be used in sophisticated mechanosynthesis processes (as the bootstrap process discussed herein demonstrates), for example, by characterizing each tip before use, by designing reactions where variation at the tip does not substantially affect the intended reactions, or by designing procedures which result in minimal variation when preparing tips. However, we will focus on the use of atomically-precise tips (after bootstrapping) due to their advantages.

Note that "tips" and "workpieces" are discussed extensively herein. However, while these terms are used for clarity, defining one structure as the tip and another as the workpiece can be arbitrary in certain circumstances. Consider that, for example, when a tip removes a hydrogen atom from a workpiece, one might also say that the workpiece donated a hydrogen atom to the tip, logically reversing their roles. This distinction may seem pedantic, but is of more than academic importance during mechanosynthetic processes such as tip refresh or using one set of tips to build another. In such instances, because you are adding or removing atoms from the tip to refresh it for the next reaction, or because you are building new tips, the tip could be considered the workpiece.

Enabling Technologies.

Mechanosynthesis is largely based upon the confluence of atomic microscopy and computational chemistry. Microscopy techniques such as Scanning Probe Microscopy (SPM), Scanning Tunneling Microscopy (STM) and Atomic Force Microscopy (AFM) have led to the ability to image and manipulate individual atoms, while computational chemistry has led to the ability to model structures which can be built by manipulating atoms, the reactions used to build those structures, and the tools required to carry out those reactions.

The ability to perform robust mechanosynthesis requires that one be able to position atoms (generally with sub-angstrom precision), that one be able to apply mechanical force to an atom in a specific direction to cause the making or breaking of bonds, that one be able to define a desired workpiece (or at least certain regions of the workpiece) with atomic precision, that one be able to calculate trajectories which will result in successful mechanosynthetic reactions and that one possess, or be able to design, tips to carry out the intended reactions. In addition to this list of necessities, it would be beneficial to be able to calculate the likelihood of pathological side reactions during mechanosynthetic reactions (the likelihood that, for example, a feedstock atom bonds to a workpiece atom adjacent to the intended target atom), the likelihood of pathological rearrangements before, during, or after a mechanosynthetic reaction, and to have control of the reaction environment (e.g., to make sure that it is inert and kept at an appropriate temperature).

Herein we describe methods, products and systems for addressing each one of these issues, taking mechanosynthesis from a laboratory curiosity to an actual manufacturing technology.

AFM/SPM/STM Microscopy. By 2006, sub-angstrom positioning in three dimensions was available for SPM. For comparison purposes, the diameter of a carbon atom is 1.54 angstroms, meaning that SPM tips could be reliably positioned to substantially less than the diameter of an atom. Also by 2006, such microscopy could be performed in ultra-high vacuum and at cryogenic temperatures, and "Vibration and drift have been controlled such that a probe tip can be held over a single molecule for hours of observation." Bharat Bhushan (Ed.) (2006) Springer Handbook of Nano-technology, Springer.

Subsequent advances in positional control have included MEMS-based platforms with additional degrees of freedom at sub-nanometer resolution. Yang, S. H., Kim, Y.-S., et al. (2012) "Microelectromechanical systems based Stewart platform with sub-nano resolution." Appl. Phys. Lett. 101 (6): 5. It should be noted that the invention discussed herein is not limited to being practiced with AFM, SPM or STM devices, but rather could use any device with the requisite positional control of a tip relative to a workpiece, and other requirements as may be necessary on a case-by-case basis (e.g., an inert environment and temperature control). While atomic microscopy equipment is exceptionally accurate, no equipment is perfect. Note that equipment capabilities could have an effect on reaction simulations. For example, Monte Carlo simulations could take into account the positional error in the equipment when determining the likelihood of a successful mechanosynthetic reaction. Note multi-tip SPM or related devices are well-known and may also be applied to the present invention. For example, force may be applied, or bonds formed, in more than one location simultaneously to stabilize an unstable intermediate workpiece structure during reactions.

Computational Chemistry in General.

Computational chemistry algorithms have existed for decades, and it is well-known that if chemical reactions are simulated at a high enough level of detail, the results are extremely accurate. Such simulations, for any large number of atoms, require substantial computer processing power. Jensen sums this up succinctly with the following quote:

"The only systems that can be solved exactly are those composed of only one or two particles . . . . Numerical solutions to a given accuracy (which may be so high that the solutions are essentially "exact") can be generated for many-body systems, by performing a very large number of mathematical operations." Jensen, F. (2007) Introduction to Computational Chemistry, John Wiley & Sons.

While the definition of "a very large number of mathematical operations" tends to change over time as computing technology progresses, generally such calculations require either supercomputers or other specialized computer hardware (e.g., ASICs, or GPUs), or clusters of commodity computer hardware. Processing power (CPU or equivalent) tends to be the limiting factor in such computations, although the memory and storage requirements (e.g., RAM, ROM, SSD, or hard drive, etc.) are not necessarily trivial.

It should be noted that there are many algorithms which can be used for computational chemistry, and that choices as to which algorithms, or when appropriate, what basis sets to use, must be made on a case by case basis considering the reactions, number of atoms, required accuracy and available computing power. And, it may be appropriate to use multiple algorithms on the same molecular model (e.g., ONIOM). We describe herein the algorithms and basis sets that we have used to calculate reactions and build sequences, and simulate workpieces.

Computational Chemistry in Mechanosynthesis.

Even on powerful computers, simulating large numbers of atoms at high levels of detail can be extremely computationally-demanding. However, an entire mechanosynthetic system need not be simulated at a high level of detail. Mechanosynthesis can be carried out in a more controlled environment than, for example, traditional liquid or gas phase chemistry, or biology, resulting in the ability to simplify simulations by reducing the number of atoms which are simulated at high levels of detail.

In mechanosynthesis, only a few positionally-controlled atoms are participating in a reaction at any given time. Most reactions away from the intended reaction position can be prevented by using an inert environment (e.g., a vacuum), and the ability to carry out reactions at low temperatures helps with reactions that cannot be prevented in this manner. Therefore, the number of atoms that are relevant to a given reaction and thus must be simulated at a high level of detail is quite small compared to the overall mechanosynthetic system or to other common settings in which chemical reactions take place. The result is that it is feasible to use computational chemistry techniques to simulate mechanosynthetic systems and reactions in a level of detail that enables one to make accurate predictions about the behavior of those systems and reactions.

Element Grouping and Simulation.

When referring to groups of elements herein, we may talk about metals, non-metals, noble gases (which we consider largely unsuited to participating directly in mechanosynthetic reactions due to their unreactive nature), transuranic elements (which we consider difficult to simulate using current software tools and hardware capabilities due to their complex electronic structure and/or lack of basis sets), stable elements (which are defined as non-radioactive isotopes and isotopes with half-lives long enough to support manufacturing and use of a product), or other logical groupings. The rationale behind these groupings would be obvious to one skilled in the art: generally the distinction is one of chemical properties (e.g., those in the same family on the periodic table or with the same valence), simulation feasibility, or practicality (e.g., safety aside, creating a device using isotopes with half-lives of minutes or shorter would seem to pose problems in manufacturing and using the device before the isotope decays).

In instances where a seemingly-arbitrary group of elements is specified, this is generally because the reactions have been simulated using the elements in the group. This will be clear from the data presented herein.

The basis sets available to simulate various elements of the periodic table can have an effect on what can be accurately simulated, though the creation of new basis sets is certainly possible.

Feedstock and Presentation Surfaces.

Mechanosynthesis requires a source of atoms on which to perform reactions. These atoms are referred to as feedstock, and to the location at which these atoms are stored as the feedstock depot. Feedstock generally resides on a presentation surface although other ways of supplying feedstock are feasible, such as liquid, gas, or as bulk solids rather than just a surface layer. Feedstock could also come attached to a tip and the tip disposed of after use.

Assuming the use of a feedstock depot, a tip under positional control can be brought to the feedstock depot and bonded to feedstock, allowing the tip to remove the feedstock from the feedstock depot and carry it away to participate in mechanosynthetic operations, e.g., to add one or more atoms to a specific site on a workpiece.

If the feedstock is being supplied from a presentation surface, that feedstock must somehow be attached to the presentation surface. Methods for coating surfaces with atoms or molecules are well-known in the art. For example, in the integrated circuit prior art, where the deposition of monolayers on GaAs, GaN, Ge, Si, SiN and other materials, has been the subject of much research. As early as Hill, the thermodynamics of gases physically adsorbed onto crystalline surfaces had been studied. Hill, T. (1959) Theory of Physical Adsorption; Advances in Catalysis & Related Subjects, Volume 4, W. G. Frankenburg, Academic Press: 212-258. Wu provides a quantum mechanical treatment of the topic of physical adsorption, including discussion of the behavior of noble gases and graphite as presentation surfaces. Wu, F. and Woot, C.-W. (1971) "Physically Adsorbed Monolayers." Chinese Journal of Physics 9(2): 68-91. And, Kruger carried out first-principle calculations for several types of atoms adsorbed to Si or Ge surfaces, and observed that these calculations agree very well with experimental data. Kruger, P. and Pollman, J. (1994) "Theory of Adsorption: Ordered monolayers from Na to Cl on Si(001) and Ge(001)." Appl. Phys. A 59: 487-502. With respect to Carbon, .CH2 groups may be distributed on a surface by several means including thermal adsorption and reaction of CH4 gas on Ge(100). Murota, J. and Sakuraba, M. (2004) Atomically controlled processing for high-performance Si-based devices. Tohoku-Cambridge Forum, International Workshop on Nano-Technology, Nano-Materials, Nano-Devices, and Nano-Systems, University of Cambridge. They may also be distributed by ion bombardment of Ge(111) using low-energy .CH3 ions. And, CVD of diamond and diamond-like carbon onto Ge substrates using CH4 feedstock gas is well-known and described in, among other places. Franks, J. (1989) "Preparation and properties of diamondlike carbon films." J. Vac. Sci. & Technol. A 7: 2307-2310. C2 is known to be one of the adsorbed species after a reaction involving perchloroethane on Si. Zhou, X. J., Li, Q., et al. (2006) "Formation of CdC and SisCl Adstructures by Insertion Reactions of cis-Dichloroethylene and Perchloroethylene on Si(100)2×1." J. Phys. Chem. B 110: 5602-5610. And C2 on graphene has been computationally analyzed. Ataca, C. and Ciraci, S. (2011) "Perpendicular growth of carbon chains on graphene from first-principles." PHYSICAL REVIEW B 83. Adsorption of the ethynyl radical has been demonstrated on Cu. Lauhon, L. and Ho, W. (2000) "Control and Characterization of a Multistep Unimolecular Reaction." PHYSICAL REVIEW LETTERS 84(7): 1527-1530. Adsorption of the ethynyl radical has also been demonstrated on Pt. Deng, R., Herceg, E., et al. (2005) "Identification and Hydrogenation of C2 on Pt(111)." J. Am. Chem. Soc. 127(50): 17628-17633. See also, Deng, R. and Trenary, M. (2007) "Carbon-Nitrogen Bond Formation from the Reaction of Ammonia with Dicarbon on the Pt(111) Surface." J. Phys. Chem. C 111(45): 17088-17093. Adsorption of the ethynyl radical has also been demonstrated on Co. Xu, L., Ma, Y., et al. (2012) "A Photoemission Study of Ethylene Decomposition on a Co(0001) Surface: Formation of Different Types of Carbon Species." The Journal of Physical Chemistry 116: 4167-4174. And the formation of C2 (among other species) within a noble gas matrix has been demonstrated. Andrews, L. (1979) "SPECTROSCOPY OF MOLECULAR IONS IN NOBLE GAS MATRICES." Ann. Rev. Phys. Chem. 30: 79-101. Many techniques, including physical vapor deposition (PVD), Atomic Layer CVD (AL-CVD), laser CVD, direct ion beam deposition, dual ion beam sputtering, electroplating, RF/DC glow discharge or microwave discharge can also be employed to create a presentation surface containing feedstock.

A presentation surface may provide more than one type of feedstock. Different feedstock could be arranged in a monolayer in different sectors of the presentation surface, or, with techniques like ALCVD, could be layered on top of each other. The feedstock could also be the surface itself. The range of elements and compounds that can be deposited on surfaces, part of the surface itself, or created through reactions resulting in adsorbed species, includes Al, BN, BeO, CH4, GaAs, Ir, LiMnO4, Mo, Ni, P2O5, Pt, Ru, Si, Si3N4, SiO2, SnO2, Ti, Ta, W, ZnO, ZnS, ZnSE, and ZnTe, among others.

It should be noted that there is a distinction to be made between physical adsorption and chemisorption (involving the formation of a new chemical bond). In general, feedstock could be bonded to a presentation surface in either manner. Depending on the reactivity of the feedstock relative to a given surface, a surface that chemisorbs one type of feedstock may physically adsorb another, although there are surfaces that tend to allow primarily physical adsorption, such as a frozen noble gas. Frozen noble gases are used both as a surface and a matrix (that is, throughout its bulk) for trapping small molecules, and are not the only set of fairly unreactive gases or compounds (for example, SiF4 may serve in a similar capacity, as might fluorinated polymers). In the case of reactions where little or no force need be applied to the tip to facilitate bonding the feedstock, physical adsorption may offer the advantage of ease of removal of the feedstock from the surface, while in cases where there is a barrier to bonding the feedstock to the tip, a covalent bond may be useful to prevent the feedstock from migrating on the presentation surface when force is applied. Covalent bonding may also be useful at higher temperatures that would permit migration or desorption of physically adsorbed feedstock.

Reliability.

Reliability is an important consideration in the design of reaction sequences for multi-atom workpieces. While some imperfections in a workpiece may be tolerable, all other things being equal, the higher the number of atoms in the workpiece, the greater the need for reliability. Reaction reliability can be achieved in a variety of ways, including use of reactions with energy barriers sufficient to prevent spontaneous reactions at a given temperature, reactions designed to avoid pathological side reactions, or the introduction of a testing step during mechanosynthesis. These topics are discussed in more detail below.

Reliability may also be determined via simulations incorporating realistic or actual equipment limitations. For example, if the positional means have known error bounds or distributions, these could be taken into account via Monte Carlo simulations.

It should be noted that in some cases, primarily with respect to hydrogen due to its low atomic mass, tunneling can contribute to reaction error. These errors can be reduced with slight modifications in build sequences and/or the use of deuterium in place of standard hydrogen. Deuterium's different mass and Van der Waal's radius also has effects on reaction rates (the kinetic isotope effect), vibrational frequencies, torsional coupling and other properties. All of these effects may be exploited by choosing to use hydrogen or deuterium on a case by case basis, and in general, any isotope of an element could be used where its properties are advantageous.

Reaction Barriers and Temperature.

One of the advantages of mechanosynthesis is that it facilitates specific, desired reactions by using directed mechanical force to overcome reaction barriers. In conventional chemistry, reaction barriers or energy deltas are often overcome by thermal energy. However, thermal energy is nonspecific and facilitates desired and undesired reactions alike. Reducing temperature decreases the thermal energy available to cause non-specific reactions. This reduces the likelihood of pathological side reactions while directed mechanical force, even at low temperatures, still facilitates desired reactions.

The Arrhenius equation and other principles of thermodynamics and computational chemistry may be used in conjunction with data on net energy differences and energy barriers to determine the reliability of a given reaction at a given temperature. For example, Code List 1 shows Mathematica version 8 code used to determine reaction reliability at a given temperature when considering the net energy difference between two structures (e.g., the starting and ending workpiece structures):

Code Listing 1:

```
(calculate reliability of a reaction at a given temperature)
  (Define Constants and Unit Conversions)
  (**Boltzmann constant=1.38*10^-23 J/K**)
  boltzmann=1.381*10^-23;
  (convert eV to Joules)
  jouleBarrier=barrier*1.6*10^-19;
  (inputs for specific reaction)
  (reaction barrier in eV)
  barrier=Abs[-0.6418];
  (temp in Kelvin)
  temperature=300;
  (Calculate Probability of Failure)
  probability=NumberForm[Exp[-jouleBarrier/(boltzmann*temperature)], 4]
```

Testing.

The most basic mechanosynthesis process involves performing a reaction with the assumption that the desired reaction took place as expected. This may be a reasonable assumption since reactions can be engineered to have high degrees of reliability. However, it is possible to obtain information on what reaction actually occurred. For example, AFM or STM techniques can be used to scan the workpiece after a reaction. If an undesired reaction occurred, various actions can be taken such as simply noting the error if it is not critical to the workpiece function, fixing the error, or discarding the workpiece and starting over.

There have been several examples of the computational analysis of mechanosynthesis, as well as experimental mechanosynthesis using atoms as feedstock. However, the experimental examples are generally limited to modifying surfaces rather than building complex or three-dimensional structures, lack separation of feedstock, presentation surface and workpiece (that is, the presentation surface often serves as all three), teach only a small, non-generalizable set of tools and reactions, and use atomically-imprecise tips with no bootstrap process to facilitate the transition to atomically-precise tips. The computational work contains other limitations, as discussed below.

Feedstock, Presentation Surface and Workpiece Terminology. It should be noted that the prior art frequently uses the same entity as the "feedstock," "presentation surface" and "workpiece." As a result, these items are frequently not distinguished in the prior art as separate entities, or referred to by the same names as used herein. This occurs when, as will be described in more detail herein, for example, an atom is removed from a surface, and then placed back onto that same surface. In such an example, the top atomic layer of the presentation surface is also the feedstock and the workpiece. Obviously, this limits the versatility of the products that can be manufactured since it constrains the elements used in reactions and the workpieces to which they are applied.

Previous Computational Simulations of Mechanosynthesis. The mechanosynthetic assembly of atomically-precise structures has been computationally examined. Drexler, K. E. (1992) Nanosystems: Molecular Machinery, Manufacturing, and Computation. New York, John Wiley & Sons. See also, Peng, J., Freitas, R., et al. (2006) "Theoretical Analysis of Diamond Mechanosynthesis. Part III. Positional C2 Deposition on Diamond C(110) Surface using Si/Ge/Sn-based Dimer Placement Tools." J. Comput. Theor. Nanosci 3: 28-41. See also, Temelso, B., Sherrill, D., et al. (2006) "High-level Ab Initio Studies of Hydrogen Abstraction from Prototype Hydrocarbon Systems." J. Phys. Chem. A 110: 11160-11173. See also, Temelso, B., Sherrill, C., et al. (2007) "Ab Initio Thermochemistry of the Hydrogenation of Hydrocarbon Radicals Using Silicon, Germanium, Tin and Lead Substituted Methane and Isobutane." J. Phys. Chem. A 111: 8677-8688. See also, Tarasov, D., Akberova, N., et al. (2010) "Optimal Tooltip Trajectories in a Hydrogen Abstraction Tool Recharge Reaction Sequence for Positionally Controlled Diamond Mechanosynthesis." J. Comput. Theor. Nanosci. 7(2): 325-353. Computational techniques have also been used to design and validate mechanosynthetic reactions and tools. Freitas, R. and Merkle, R. (2008) "A Minimal Toolset for Positional Diamond Mechanosynthesis." Journal of Computational and Theoretical Nanoscience 5(5): 760-861. See also, U.S. Pat. No. 8,171,568. However, due to insufficient simulation detail, lack of a bootstrap sequence, lack of a comprehensive set of reactions and tips, or other drawbacks, previous work has not been directed to a system that can be implemented using existing technology, capable of a large set of reactions that can be used to create complex atomically-precise structures.

Experimental Demonstrations of Atomic Manipulation and Mechanosynthesis. In addition to being able to image single atoms, as early as 1989 a Scanning Tunneling Microscope was used to spell "IBM" using 35 xenon atoms arranged on a nickel surface, though no covalent bonds were formed. Eigler, D. M. and Schweizer, E. K. (1990) "Positioning Single Atoms with a Scanning Tunnelling Microscope." Nature 344: 524-526.

In 2003, making and breaking of covalent bonds using mechanosynthesis via atomic force microscopy (AFM) was demonstrated for silicon atoms on a silicon surface. The AFM tip was used to remove, and re-deposit, Si atoms from the surface. Oyabu, N., Custance, O., et al. (2003) "Mechanical vertical manipulation of selected single atoms by soft nanoindentation using near contact atomic force microscopy." Phys. Rev. Lett. 90(17). Subsequently, other demonstrations of mechanosynthesis have been published, including: manipulation of silicon atoms on a silicon/oxygen surface (Morita, S., Sugimoto, Y., et al. (2004). "Atom-selective imaging and mechanical atom manipulation using the non-contact atomic force microscope." J. Electron Microsc. 53(2): 163-168.), manipulation of germanium atoms on germanium surfaces (Oyabu, N., Custance, O., et al. (2004). Mechanical Vertical Manipulation of Single Atoms on the Ge(111)-c(2×8) Surface by Noncontact Atomic Force Microscopy. Seventh International Conference on non-contact Atomic Force Microscopy, Seattle, Wash.), manipulation of polymers on silicon surfaces (Duwez, A., Cuenot, S., et al. (2006). "Mechanochemistry: targeted delivery of single molecules." Nature Nanotechnology 1(2): 122-125), and manipulation of silicon and tin atoms on a silicon surface (Sugimoto, Y., Pou, P., et al. (2008). "Complex Patterning by Vertical Interchange Atom Manipulation Using Atomic Force Microscopy." Science 322: 413-417).

Mechanosynthesis Tools in the Prior Art. Prior to Freitas and Merkle (2009), few tools for mechanosynthesis had been described in the literature. These included a hydrogen abstraction tool described by Temelso, Sherrill et al. (2006), a hydrogen donation tool described by Temelso, Sherrill et al. (2007), and a dimer placement tool as described by Peng, Freitas et al. (2006). Site-specific hydrogen abstraction has also been demonstrated. Hersam, M. C., Abeln, G. C., et al. (1999) "An approach for efficiently locating and electrically contacting nanostructures fabricated via UHV-STM lithography on Si(100)." Microelectronic Engineering 47: 235-237. However, this was not via purely mechanical means but rather used an electrically-pulsed STM tip. Similarly, site-specific hydrogen donation was achieved experimentally by depositing hydrogen atoms onto a silicon surface by applying a voltage bias to a tungsten tip. Huang, D. H. and Yamamoto, Y. (1997) "Physical mechanism of hydrogen deposition from a scanning tunneling microscopy tip." Appl. Phys. A 64: R419-R422.

Additionally, U.S. Pat. No. 7,687,146 teaches a dimer tip for mechanosynthetic fabrication. The invention is described as comprising "adamantane molecules arranged in a polymantane or lonsdaleite configuration" and a "dimerholder atom." The tip structure is thus constrained to a very specific set of structures and is directed to the use of a dimer as feedstock.

Further, the tip is intended for use with deposition surfaces "having a melting point of at least 300° C., a thermal expansion coefficient maximally different than that of diamond, a mismatch in crystal lattice constant as compared to that of diamond, resistance to carbide formation, less bonding strength to the carbon dimer as compared to bonding strength between the diamondholder atom X and the carbon dimer, and little or no solubility or reaction with carbon." Thus, the possible reactions and deposition surfaces taught are subject to many constraints.

Subsequent to 2009, a carbon nanotube-based scheme for creating atomically-precise tips that can also provide positioning capability was described. Artyukhov, V. I. (2010) "A six degree of freedom nanomanipulator design based on carbon nanotube bundles." Nanotechnology 21(38): 9.

However, none of the tools described previously, alone or in combination, could practically provide a bootstrap process, a set of tools exhibiting closure (that is, a set of tools that could build themselves), a versatile set of reactions, a set of reactions of known reliability, nor were they directed to a system for three-dimensional fabrication, among other drawbacks.

Prior Art is Surface-Based.

In the prior art mechanosynthesis is generally performed on, or to, a surface. For example, in Oyabu, Custance et al. (2003) and Oyabu, Custance et al. (2004), vertical manipulation of single atoms was performed, on either a Si or Ge surface. These manipulations consisted of removing an atom (referred to as an "adatom" in the field of surface chemistry) from the surface, and filling the vacancy left by the removal of the adatom with an identical atom. No manipulation of atoms is demonstrated except where from, or to, the very top atomic layer of a surface. Additionally, in many cases, including Oyabu, Custance et al. (2003) and Oyabu, Custance et al. (2004), not only is the work limited to surfaces, but to specific crystal structures of those surfaces, such as the 7×7 reconstruction on Si and the 2×8 reconstruction on Ge, respectively.

Prior Art Uses Presentation Surface as Feedstock and Workpiece.

As exemplified by Oyabu, Custance et al. (2003) and Oyabu, Custance et al. (2004), the prior art frequently uses the presentation surface itself as what we refer to as the feedstock depot, the feedstock, and the workpiece. For example, atoms are removed from the crystal structure of the presentation surface and then added back to a void in that same presentation surface. The atoms are not being removed from the surface to transport to a workpiece distinct from the presentation surface. In these types of experiments, the presentation surface is the source of the feedstock and it is also the workpiece which is being altered by the mechanosynthetic reactions. Use of the presentation surface as the feedstock depot, feedstock, and workpiece places limitations on what workpieces may be built, as workpieces are thus limited to being made out of the same element(s) as the presentation surface, among other drawbacks.

Prior Art Limited to One or Two Dimensions.

The prior art does not anticipate being able to extend atomically-precise mechanosynthetically-created structures into three dimensions. Creating a three-dimensional structure using mechanosynthesis is not simply the extension or repetition of a two-dimensional motif. The bonding structure and build sequence must support extension into the third dimension through a sequence of reactions that is chemically and geometrically feasible without pathological rearrangement of intermediate products. This requires a considered build sequence resulting from analysis of the reactions and intermediate structures, and such strategies are not taught in the prior art.

Prior Art Teaches Limited Reactions and Elements.

The prior art is frequently limited to the removal of a single adatom (a surface atom), or the insertion of a single atom into a vacancy left by the removal of such an adatom, often using a single element and involving a very specific crystal structure. For example, Oyabu, Custance et al. (2003) and Oyabu, Custance et al. (2004) use either all Si atoms, or all Ge atoms, respectively. There is no evidence that different intentional modifications to the presentation surface could have been made or that different crystallographic faces could have been used.

Sugimoto, Pou et al. (2008) uses two elements in a single experiment, slightly expanding upon previous work, but this work is still directed to limited modifications that are made to a two-dimensional presentation surface. As in other prior art discussed herein, the feedstock, workpiece and presentation surface are synonymous in this work.

In similar work, but induced by voltages, not mechanosynthesis, Ho teaches bond formation between Fe and CO to form Fe(CO), and then repeats the reaction to form Fe(CO)2. Ho, W. and Lee, H. (1999) "Single bond formation and characterization with a scanning tunneling microscope." Science (286): 1719-1722. Three elements and four reactions, only two of which are distinct, are thus used. Note that the experimental setup in this example does not demonstrate a robust set of reactions applicable to building complex structures. The authors avoided the need for designing reactions that could accurately bind feedstock to closely-spaced atomic structures by spacing the Fe atoms far apart and then creating a simple structure involving only a single Fe atom.

Prior Art does not Use Atomically-Precise Tips.

The prior art generally does not use atomically-precise tips (U.S. Pat. No. 7,687,146 is one exception that is discussed in detail herein). For example, the tip in Oyabu, Custance et al. (2003) is described as a "Si tip apex [that] was carefully cleaned up by argon-ion bombardment for 30 min." Such a process would result in a tip where the placement of individual atoms was unknown. When a tip is not atomically-precise its reaction characteristics cannot be exactly defined via computational chemistry modeling, and would not be the same from tip to tip.

Prior Art does not Teach Varied Tips.

When contemplating numerous reactions between various elements, different tips will be required to facilitate the specific reactions desired. To the best of our knowledge the prior art does not address this issue.

Prior Art does not Provide for Specific Levels of Reaction Accuracy.

The accuracy of the mechanosynthetic reactions must be considered if one is to build workpieces with a known level of confidence. The mechanosynthesis prior art generally does not address the issue of designing for reaction reliability. Some prior art reports the reliability of a given reaction after the fact based on experimental results, but this is very different than engineering the system ahead of time so that the reactions achieve a desired level of accuracy. For example, Sugimoto, Pou et al. (2008) provides computer modeling of a reaction barrier in rationalizing the behavior of their experimental system. But, this analysis is post-facto, using a single element. They did not attempt to design a system ahead of time with a known level of reliability.

Further, as previously noted, the prior art generally uses atomically-imprecise tips. Even where modeling is performed in the prior art, modeling of an atomically-imprecise tip is unlikely to accurately represent the actual experimental system due to lack of knowledge of the exact structure of the tip. Obviously, since the prior art is not directed to a system with a planned level of reliability, neither does the prior art investigate reaction reliability across a range of tips, elements, or conditions to teach a generalizable system.

Prior Art Using Voltage Biases.

The prior art contains examples of atomic-scale synthesis using voltage biases. Voltage biases can be used to modify surface bonding patterns by two general mechanisms: localized heating and electrostatic fields. Such mechanisms may be less specific than mechanosynthesis in their ability to facilitate reliable reactions, but provide easily-accessible ways to make and break covalent bonds. While it should be noted that mechanosynthesis and voltage-based techniques could be combined, no generalizable system using voltages has been taught in the prior art and in general, the same advantages that distinguish the present invention from the mechanosynthesis prior art also distinguish the present invention from the voltage-based prior art.

Prior Art not Using Individual Atoms or Molecules.

Prior art using large (compared to atoms) building blocks is not an appropriate parallel to positioning, and making and breaking bonds, at the atomic or molecular level. For example, (Ramachandran, Baur et al., 1998) discusses "manipulation of nanoscale three-dimensional (3D) features." On its face, this may sound similar to the present invention. However, the "features" to which they refer are gold nanoparticles ranging from 5 nm to 15 nm in diameter. Gold atoms have a diameter of approximately 0.14 nm, and therefore such particles would contain thousands of atoms, precluding the idea of atomic precision in positioning, or the making and breaking of specific bonds.

The wording of the prior art is not always clear as to when atoms are being referred to, versus some larger (and often indistinctly-defined) building block. Terminology used in the prior art includes "cluster," "nanoparticle," "nanoscale object," "particle" and "nodule," among other terms.

Regardless of the terminology, the use of imprecisely-defined multi-atom aggregates is inherently different than the use of atoms or atomically-precise molecules.

Summary of Mechanosynthesis-Based Prior Art.

Ignoring the prior art which does not result in atomically-precise products, does not act upon atomically-precise feedstock, or is not parallel to the current invention for other reasons, the prior art with respect to mechanosynthesis teaches the ability to make and break bonds using a small set of elements, with a limited set of reactions, only to specific structures (such as the 7×7 reconstruction of Silicon, or other similarly-specific and limited environments), involving only the top atomic layer of a presentation surface. And, the experimental mechanosynthetic reactions found in the prior art do not appear to have been engineered in advance for versatility or reliability using computational chemistry techniques. Reliability, while a minor issue when, for example, the goal is to simply interchange one atom for another on a surface, becomes important when the goal is to reliably build atomically-precise structures containing many atoms or requiring many reactions.

Another drawback of the prior art is that the presentation surface also frequently serves as the feedstock depot, feedstock and workpiece, such as with the "vertical manipulation" prior art, of which Oyabu, Custance et al. (2003) andOyabu, Custance et al. (2004) are representative. Without separating the presentation surface, feedstock and workpiece, the ability to create diverse structures can be limited.

Drawbacks are also created by the use of non-atomically-precise tips in the prior art. And, the prior art contains no teachings as to how one might generalize the mechanosynthetic techniques presented to other elements and reactions, or to construct complex, three-dimensional workpieces.

Overall, the prior art is directed towards viewing mechanosynthesis as a set of limited individual surface modifications which are a laboratory curiosity, not as a generalizable set of tools, reactions and procedures designed for reliably building varied workpieces. The present invention addresses all of these issues, as will be seen from the detailed explanations and exemplary embodiments.

SUMMARY OF THE INVENTION

The present invention is directed to methods and systems for building three-dimensional workpieces which are described using a plurality of mechanosynthetic reactions. These methods may employ engineered reliability in reactions and process conditions and may use simulated or otherwise vetted reaction sequences, to allow workpieces requiring many reactions to be built with acceptable reliability. These many reactions may be the repetition of one or a small number of reactions, or many diverse reactions, or a combination thereof.

BRIEF DESCRIPTION OF THE DRAWINGS

A complete understanding of the present invention may be obtained by reference to the accompanying drawings, when considered in conjunction with the subsequent, detailed description, in which.

DETAILED DESCRIPTION

Figure 1A:
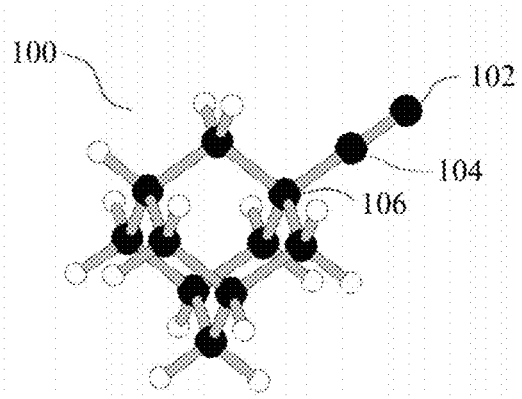
FIG. 1A is an active Hydrogen Abstraction Tool.

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed with the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, if dates of publication are provided, they may be different from the actual publication dates and may need to be confirmed independently.

Definitions

The following definitions are used herein:

An "adamantane" molecule comprises a 3D cage structure of ten carbon atoms, each terminated with one or two hydrogen atoms, having the chemical formula C10H16 and representing the smallest possible unit cage of crystalline diamond.

An "adamantane molecular structure" is a molecular structure that is similar to and may include a single adamantane molecule, but also includes adamantane molecules which (1) may lack one or more terminating atoms, (2) may be covalently bonded to one or more neighboring adamantane cages in various well-known crystallographic lattice geometries, and (3) may employ elements other than carbon and hydrogen to form equivalent cage or crystallographic lattice geometries.

An "adamantane-like molecular structure" is (1) any polycyclic closed shell molecular structure composed entirely of carbon, nitrogen, oxygen and hydrogen, or (2) any molecular structure as in (1) that has been modified by substituting one or more atoms which, in the substituted molecular structure, have similar valence to the substituted carbon, nitrogen, oxygen or hydrogen atoms. By way of example, and not of limitation, an adamantane-like molecular structure would include adamantane, polymantanes, heteroadamantanes, iceane, cubane, pagodane, dodecahedrane, cage or polycyclic hydrocarbons, graphene, fullerenes, carbon nanotubes, diamond shards terminated by hydrogen, fragments of lonsdaleite terminated with hydrogen, fragments of silicon or germanium terminated by hydrogen, fluorine terminated adamantane, or incompletely terminated polymantanes.

An "atom" includes the standard use of the term, as well as a radical, which, for example, may be just a proton in the case of $H^+$.

"Atomically-precise" means where the positions of each atom are known to a precision adequate to establish the likely bonding structure.

The "bridgehead position" of an adamantane-like molecular structure refers to a structural atom that is bonded to three other structural atoms and is terminated by one or more nonstructural atoms.

"Build sequence," see "mechanosynthetic reaction sequence."

A "chemical bond" is an interatomic covalent bond or an interatomic ionic bond, as these terms are commonly understood by practitioners skilled in the art.

A "chemical reaction" is said to occur when chemical bonds are formed or broken, or when the directionality, strength, or other salient characteristics of an existing chemical bond is altered, as for example during positionally controlled bond bending.

A "coaxial" reaction or trajectory is one in which the bond broken and the bond formed lies on the same line.

"Diamond" is a hydrocarbon adamantane molecular structure consisting of repeating adamantane cage units arranged in various well-known crystallographic lattice geometries.

"Diamondoid" materials include any stiff covalent solid that is similar to diamond in strength, chemical inertness, or other important material properties, and possesses a three-dimensional network of bonds. Examples of such materials include but are not limited to (1) diamond, including cubic and hexagonal lattices and all primary and vicinal crystallographic surfaces thereof, (2) carbon nanotubes, fullerenes, and other graphene structures, (3) several strong covalent ceramics of which silicon carbide, silicon nitride, and boron nitride are representative, (4) a few very stiff ionic ceramics of which sapphire (monocrystalline aluminum oxide) is representative, and (5) partially substituted variants of the above that are well-known to those skilled in the art.

"Feedstock" is the supply of atoms used to perform mechanosynthetic reactions on a workpiece. Feedstock may take the form an atom or atoms (a molecule), including radicals (e.g., .GeH2, .CH2).

A "handle structure" comprises a plurality of atoms whose bonding pattern or electronic state is not altered during a site-specific mechanosynthetic chemical reaction and whose primary function is to hold a mechanosynthetically active tip or tool in a fixed geometric relationship that will permit a mechanosynthetic chemical reaction to proceed when the handle is manipulated by a positional device. Handle structure may include the null case.

An "inert environment" includes, but is not limited to, UHV, helium, neon, or other noble gases either individually or in combination, or other gases or liquids that do not react with the tip or workpiece during mechanosynthetic operations.

"Mechanical force" may include applied mechanical forces having positive, negative, or zero magnitude. Chemical reactions driven by the application of mechanical force include reactions that are (1) driven through its reaction barrier by mechanically forcing reactants or products through the transition state, or (2) potentially reactive sites are driven away from a competing undesired reaction by mechanically restraining potentially reactive sites from attaining closer physical proximity, or (3) allowed to occur by bringing potentially reactive sites into closer physical proximity when zero mechanical force is required to do so, as for example when no reaction barrier exists.

"Mechanosynthesis" uses chemical reactions driven by the application of mechanical force using site-specific positional control to facilitate the fabrication of multi-atom, atomically-precise structures.

A "mechanosynthetically active tip" is a tip controlled by a positional device that can perform mechanosynthetic reactions.

A "mechanosynthetic reaction" (sometimes referred to as a "reaction" when context makes it clear that the reaction is mechanosynthetic) is an individual chemical reaction that is driven to completion by the application of mechanical force.

A "mechanosynthetic reaction sequence" (sometimes referred to as a "reaction sequence" when context makes it clear that the reaction sequence is mechanosynthetic) is a series of reactions arranged in an ordered sequence that permits the fabrication of complex atomically-precise structures comprising a plurality of atoms and chemical bonds. Also referred to as a build sequence.

A "positional device" is a device capable of exerting atomically-precise positional control on a mechanosynthetic tip, tool, or workpiece, and may include, but is not limited to, a conventional scanning probe microscope (SPM) such as an atomic force microscope (AFM), a miniaturized or MEMS-scale SPM or AFM, a robotic arm mechanism of any size scale, or other appropriate manipulation system capable of atomically-precise positional control.

A "pathological side reaction" is an undesired reaction which may happen in the course of mechanosynthesis, such as bonding feedstock to the wrong atom on a workpiece, or a rearrangement of atoms on a workpiece due to instability of an intermediate structure during the building process.

The "sidewall position" of an adamantane-like molecular structure refers to a structural atom that is bonded to two other structural atoms and is terminated by one or more nonstructural atoms.

"Site-specific" refers to knowing, and being able to constrain, with the necessary degree of reliability, the site at which mechanosynthetic reactions take place.

A "structural atom" in an adamantane-like molecular structure refers to an atom comprising the cage framework, for example a carbon atom in an adamantane molecule.

A "structural substituent atom" is an atom that occupies either a bridgehead or a sidewall position in an adamantane-like molecular structure.

A "terminating atom" in an adamantane-like molecular structure refers to an atom that does not serve as a constituent atom in the cage structure but absorbs unused valences of a structural atom comprising the cage framework, for example a hydrogen atom in an adamantane molecule.

A "three-dimensional" workpiece means a workpiece composed of a lattice of atoms which occupies three dimensions if an individual atom is assumed to be without size. Similarly, a two-dimensional workpiece would be composed of a plane of atoms.

A "tool" is a mechanosynthetically active tip covalently bonded to a handle structure.

A "toolset" is a selected set of mechanosynthetic tools.

A "tip" is a device for facilitating mechanosynthetic reactions which includes one or more "active" atoms whose bonding pattern or electronic state is altered during a mechanosynthetic operation, and one or more "support" atoms whose bonding pattern or electronic state is not altered during a mechanosynthetic operation. The support atoms function to hold the active atoms in position. A tip may be atomically-precise or imprecise.

A "transfer passivating atom" is an atom that passivates one or more open valences of a transfer substituent atom.

A "transfer substituent atom" is an atom that terminates a structural substituent atom via a single covalent bond, and that may be chemically transferred to a workpiece during a site-specific positionally-controlled mechanosynthetic chemical reaction driven by the application of mechanical force.

A "workpiece" is an object built via mechanosynthesis. In addition to the common scenario where a workpiece is a product or device, a workpiece may be, or include, feedstock, tools, waste atoms, intermediate structures, combinations thereof, or other objects. A system may have more than one workpiece.

A dot (".") is frequently used in chemical structures herein to represent an electron, as in the radical group ".CH2". For ease of typesetting, the notation herein generally omits subscript, in favor of simply writing the number in-line (again, as in ".CH2"), as its meaning is still clear and unambiguous. Superscript may be written using the "^" character when required for clarity.

Applications of the Invention

The invention is used to fabricate atomically-precise, multi-atom structures. The present invention has many advantages, including the ability to fabricate complex structures to atomically-precise specifications, the ability to position individual atoms or groups of atoms in specific locations on a workpiece, the ability to remove specific groups of atoms from specific sites on a workpiece, the ability to make atomically-precise modifications to a workpiece, the ability to make specific sites on a workpiece become reactive while the rest of the workpiece remains relatively unreactive, and the ability to make specific sites on a workpiece become unreactive.

The particular tools, tips, reactions, build sequence and other teachings herein are embodiments of the invention and should not be construed to limit the invention to only the disclosed embodiments. The teachings herein readily extend the invention to a wider range of tools, tips, reactions, elements, structures and conditions.

Overview of the Bootstrap Tools and Reactions

The present invention provides a pathway for the creation of a set of mechanosynthetic molecular tools that are able to fabricate the self-same set, refresh all tools in the set, allow for numerous reactions using many elements, and create diverse workpieces, including many-atom, three dimensional structures. Described is a set of mechanosynthetic tools that achieves all these objectives, and then described is a bootstrap process to build the first set of such tools.

While some of these mechanosynthetic tools have been analyzed in the literature, no complete set of tools has been described which are able to fabricate a wide variety of complex structures, including themselves, with a bootstrap sequence to allow the creation of the first set of tools.

The set of mechanosynthetic molecular tools comprises: (1) the Hydrogen Abstraction Tool, shown in FIG. 1; (2) the Hydrogen Donation Tool, shown in FIG. 2; (3) the Germanium Radical Tool, shown in FIG. 3; (4) the Methylene Tool, shown in FIG. 4; (5) the GermylMethylene Tool, shown in FIG. 5; (6) the Germylene Tool, shown in FIG. 6; (7) the Hydrogen Transfer Tool, shown in FIG. 7; (8) the Adamantane Radical Tool, shown in FIG. 8; and (9) the Dimer Placement Tool, shown in FIG. 9.

While this specific set of tools has the ability to fabricate and refresh (charge or discharge a tool, as needed) all the tools in the toolset as well as the ability to make a range of other products (in this case, a wide range of structures composed of hydrogen, carbon and germanium), it is provided as an exemplary embodiment and it should be understood that other sets of mechanosynthetic tools would be apparent to one skilled in the art and having the benefit of the teachings presented herein.

In the following description, it is described how, given a sufficient number of each type of molecular tool, one can fabricate more molecular tools of any given type, how to recharge the molecular tools, and how to use the molecular tools to fabricate other molecular structures.

Tool Details

The nine principal tools have been listed above. A detailed description of these tools follows. For clarity, all figures show the active atoms of each tip for a given tool, and some supporting atoms but do not show the handle structure that is attached to each tip to make the complete tool. This is because the handle structure can be much larger than the tip and the site of mechanosynthetic chemical activity is the tip, not the handle. Understand that while a handle may not be shown, it is assumed to exist when necessary for positioning the tools with atomic precision.

All atomically-precise tools and mechanosynthetic reactions described have been analyzed at high levels of accuracy, using supercomputers and/or parallel processing. Generally, coarse structure determination was done using molecular mechanics methods, and these designs were subsequently refined using Density Functional Theory (DFT) methods. Thousands of tool structures, reactions, and reaction sequences have been examined, using millions of CPU hours (where a "CPU" is equivalent to a 3 GHz standard processor).

In more detail, the bootstrap tools are:

(1) The Hydrogen Abstraction Tool. FIG. 1A illustrates the active tip of the Hydrogen Abstraction Tool 100 which is used to selectively abstract a single hydrogen atom from a workpiece. Hydrogen Abstraction Tool 100 is shown prior to the abstraction of a hydrogen atom. The distal carbon atom 102 is a radical with a high affinity for hydrogen. Carbon atoms 102 and 104 are triply bonded to each other and in this and other structures are commonly referred to as "an ethynyl radical" or a "dimer." The ethynyl radical is bonded to carbon atom 106, called a "bridgehead" carbon atom. The remainder of the adamantane cage consists of 10 carbon atoms and the hydrogen atoms which terminate them.

In general use, the 6 carbon atoms at the base of the adamantane cage (i.e., the six carbon atoms in the adamantane cage most distant from carbon atom 106 in FIG. 1A) are bonded to a handle structure by which the tool is positioned.

The Hydrogen Abstraction Tool is used by positioning the tool so that carbon atom 102 is in close proximity (e.g., one or two angstroms) to a hydrogen atom which is to be abstracted.

When the Hydrogen Abstraction Tool is so positioned, the selected hydrogen atom will bond more strongly to carbon atom 102 than to almost any other molecular structure and hence will transfer from that other structure to carbon atom 102. The Hydrogen Abstraction Tool 100 following a hydrogen abstraction will appear as a spent Hydrogen Abstraction Tool 110 shown in FIG. 1B, where the abstracted hydrogen 112 is shown bonded to carbon atom 102.

Figure 2:
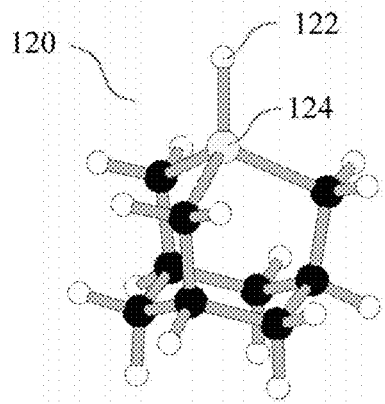
FIG. 2 is a Hydrogen Donation Tool.

(2) The Hydrogen Donation Tool. FIG. 2 illustrates the Hydrogen Donation Tool 120. The hydrogen atom 122 is bonded to germanium atom 124. Because the bond between germanium atom 124 and hydrogen atom 122 is not as strong as the bond that can be formed between hydrogen atom 122 and a carbon radical on a workpiece, the hydrogen atom 122 will, when positioned close to a carbon radical and with the application of mechanical force to overcome reaction barriers, transfer to that carbon radical and so donate a hydrogen to it.

Figure 3:
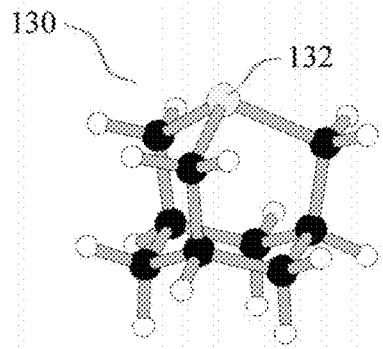
FIG. 3 is a Germanium Radical Tool.

(3) The Germanium Radical Tool. FIG. 3 illustrates the Germanium Radical Tool 130. The germanium atom 132 is a radical. The Germanium Radical Tool 130 results from the reaction that will occur when the Hydrogen Donation Tool 120 donates hydrogen atom 122 to a carbon radical.

Figure 4:
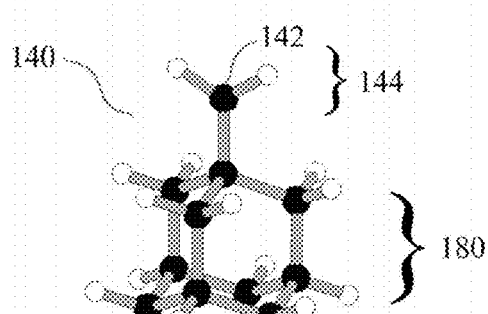
FIG. 4 is a Methylene Tool.

(4) The Methylene Tool. FIG. 4 illustrates the Methylene Tool 140. The Methylene Tool is formed by adding a .CH2 group 144 to the Adamantane Radical Tool 180. The carbon atom 142 in .CH2 group 144 is highly reactive because it is a radical.

Figure 5:
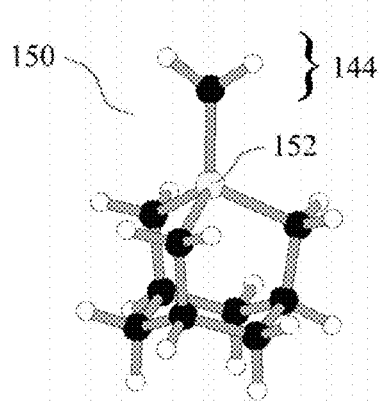
FIG. 5 is a GermylMethylene Tool.

(5) The GermylMethylene Tool. FIG. 5 illustrates the GermylMethylene Tool 150. Because the bond between .CH2 group 144 and germanium atom 152 is relatively weak, the GermylMethylene tool can be used to transfer the .CH2 group 144 to a carbon radical site on a growing workpiece.

Figure 6:
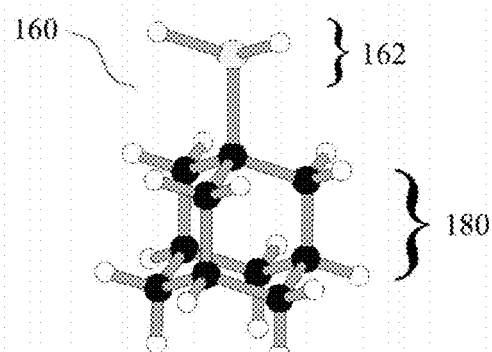
FIG. 6 is a Germylene Tool.

(6) The Germylene Tool. FIG. 6 illustrates the Germylene Tool 160 which can be formed by adding a .GeH2 group 162 to the Adamantane Radical Tool 180. Germylene Tool 160 can be used in reaction sequences that add a germanium atom to a workpiece (and in particular, can be used during the synthesis of the Germanium Radical Tool 130).

Figure 7:
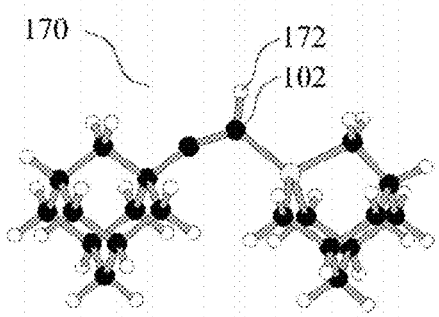
FIG. 7 is a Hydrogen Transfer Tool.

(7) The Hydrogen Transfer Tool. FIG. 7 illustrates the Hydrogen Transfer Tool 170 which can be formed by the reaction shown in FIG. 12A. The Hydrogen Transfer Tool is particularly useful because the bond between carbon atom 102 and hydrogen atom 172 is particularly weak, making it an excellent hydrogen donation tool.

Figure 8:
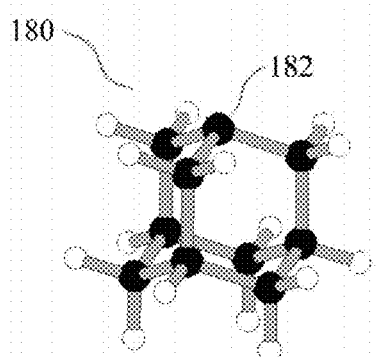
FIG. 8 is an Adamantane Radical Tool.

(8) The Adamantane Radical Tool. FIG. 8 illustrates the Adamantane Radical Tool 180 which can be formed by abstracting a hydrogen atom from an exposed adamantane cage on any diamond surface located, e.g., at the terminus of a tip, producing a single carbon radical 182.

Figure 9:
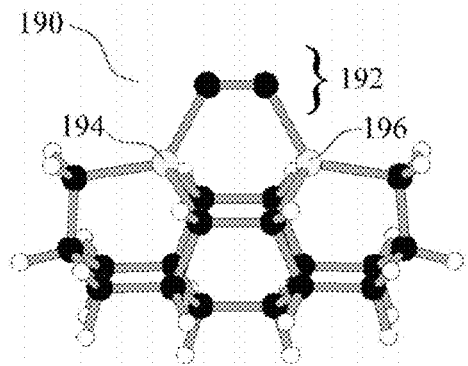
FIG. 9 is a Dimer Placement Tool.

(9) The Dimer Placement Tool. FIG. 9 illustrates the Dimer Placement Tool 190 in which a dimer 192 bonds to a tip which has two germanium atoms 194 and 196. The two bonds between the dimer 192 and the two germanium atoms 194 and 196 are highly strained, making the resulting Dimer Placement Tool 190 reactive and suitable for adding a dimer to a growing workpiece, particularly when two adjacent radical sites are present on the workpiece to which the dimer can bond.

Use of the Tools

These nine tools are used in an inert environment (e.g., ultra-high vacuum, a pressure of $10^{-9}$ Torr ($10^{-12}$ atm) or less) and require that some suitable positional device be used to position the tools with high accuracy. In addition, there must be a source of feedstock to provide the needed hydrogen, carbon and germanium atoms and optionally a sink for discard atoms if there is excess hydrogen.

One way to provide hydrogen is from a presentation surface covered by hydrogen atoms (e.g., a bulk produced flat hydrogenated diamond surface).

One way to provide carbon is in the form of .CH2 groups distributed on a suitable presentation surface (e.g., on a bulk produced flat germanium surface). This also provides hydrogen, which may eliminate the need for an independent source for hydrogen. One way to provide germanium is in the form of .GeH2 groups distributed on a suitable presentation surface (e.g., on a bulk produced flat germanium surface).

Both carbon and germanium can also enter the system when provided as methyl or germyl groups (CH3 or GeH3) on a suitable presentation surface. In this case, they can be made chemically active by abstracting a hydrogen atom and converting them into .CH2 or .GeH2 groups respectively.

Excess hydrogen must be removed if, for example, the product structure being built has fewer hydrogen atoms than are present in the feedstock, in which case, e.g., the excess hydrogen atoms provided by the .CH2 groups must be disposed of. One way of doing this is to provide a surface to which the Hydrogen Donation Tool can donate hydrogen atoms. One such surface would be a bulk-produced atomically flat non-hydrogenated diamond surface.

These nine tools are used to carry out the various reactions needed to recharge themselves, to fabricate more tools, and to make other atomically-precise structures (products).

Hydrogen Abstraction

Figure 10A:
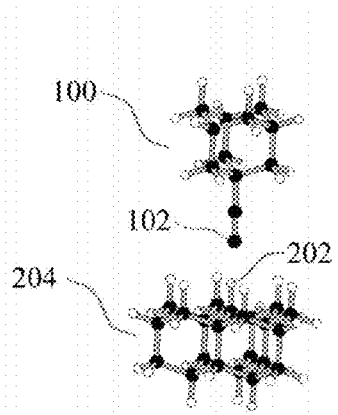
FIG. 10A shows a Hydrogen Abstraction Tool selectively abstracting a hydrogen atom.

FIG. 10A illustrates the use of the Hydrogen Abstraction Tool 100 to selectively abstract hydrogen atom 202. Hydrogen Abstraction Tool 100 is positioned so that radical carbon atom 102 is just above hydrogen atom 202 which is bonded to diamond surface 204. When Hydrogen Abstraction Tool 100 is brought into close proximity to diamond surface 204, the hydrogen atom 202 will bond to carbon atom 102, and thus transfer from diamond surface 204 to Hydrogen Abstraction Tool 100.

Figure 10B:
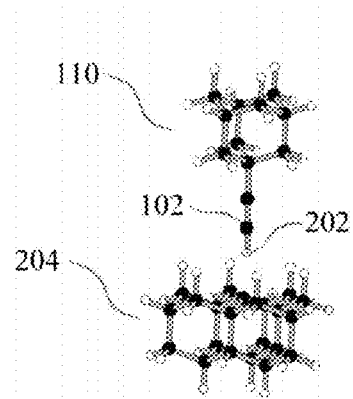
FIG. 10B shows abstraction in the transfer of a hydrogen atom and conversion to a spent Hydrogen Abstraction Tool.

FIG. 10B illustrates the result of the transfer of the hydrogen atom 202 to the Hydrogen Abstraction Tool 100 which serves to convert the Hydrogen Abstraction Tool 100 into a spent Hydrogen Abstraction Tool 110.

Hydrogen Donation

In one embodiment, a reaction sequence transfers a hydrogen atom from a Hydrogen Donation Tool to a diamond surface, both hydrogenating the radical site on the diamond surface and converting the Hydrogen Donation Tool to a Germanium Radical tool.

Figure 11A:
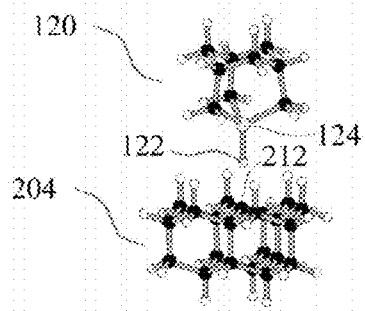
FIG. 11A shows a Hydrogen Donation Tool selectively donating a hydrogen atom.

FIG. 11A illustrates the use of the Hydrogen Donation Tool 120 to selectively donate one hydrogen 122 atom to carbon radical 212 on diamond surface 204. The Hydrogen Donation Tool 120 can be positioned directly above diamond surface 204 proximally close to carbon radical 212. When Hydrogen Donation Tool 120 is brought into close proximity to diamond surface 204 such that the attractive force between hydrogen atom 122 and carbon radical 212 exceeds the attractive force between the hydrogen atom 122 and the germanium atom 124, the hydrogen atom 122 will transfer from the germanium atom 124 and bond to the diamond surface 204 at the site of the carbon radical 212.

Figure 11B:
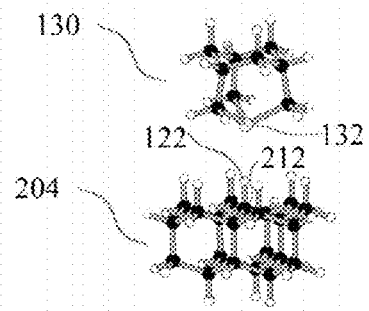
FIG. 11B shows the donation of a hydrogen atom and conversion to a Germanium Radical Tool.

FIG. 11B illustrates the result of the transfer of the hydrogen atom 122 to carbon atom 212 (now no longer a radical), which serves to convert the Hydrogen Donation Tool 120 into a Germanium Radical Tool 130 now having a germanium radical 132.

Recharge of Hydrogen Abstraction and Hydrogen Donation Tools

In one embodiment, a reaction sequence refreshes a Hydrogen Abstraction Tool by transferring a hydrogen atom from a spent Hydrogen Abstraction Tool to a Germanium Radical Tool.

Figure 12A:
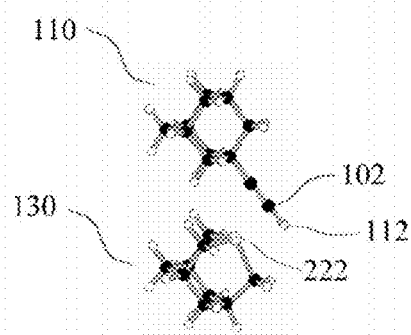
FIG. 12A shows a Germanium Radical Tool bonding to a spent Hydrogen Abstraction Tool.

FIG. 12A illustrates a Germanium Radical Tool 130 and a spent Hydrogen Abstraction Tool 110 with distal carbon atom 102 bonded to hydrogen atom 112. The spent Hydrogen Abstraction Tool is then brought into proximity to the Germanium Radical Tool 130 so that germanium radical 222 bonds to carbon atom 102 of spent Hydrogen Abstraction Tool 110. The result of the reaction is illustrated in FIG. 12B.

Figure 12B:
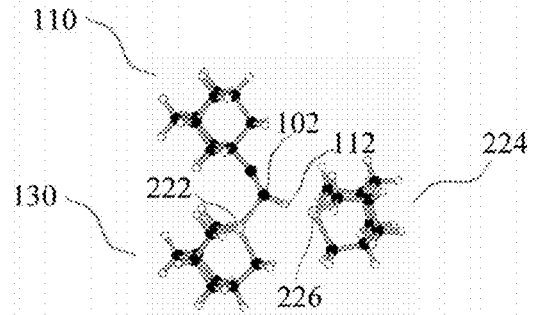
FIG. 12B shows a Germanium Radical Tool weakly bonded to a spent Hydrogen Abstraction Tool.

FIG. 12B illustrates the germanium radical 222 of the Germanium Radical Tool bonded to the distal carbon of the spent Hydrogen Abstraction Tool 110 in which hydrogen atom 112 is weakly bonded to carbon atom 102, along with a second (unbonded) Germanium Radical Tool 224. When the second Germanium Radical Tool 224 is positioned in close proximity to hydrogen atom 112 the hydrogen atom 112 debonds from carbon atom 102 and bonds to the germanium radical 226 of the second Germanium Radical Tool 224, thereby converting the second Germanium Radical Tool 224 into a Hydrogen Donation Tool. The result of the reaction is illustrated in FIG. 12C.

Figure 12C:
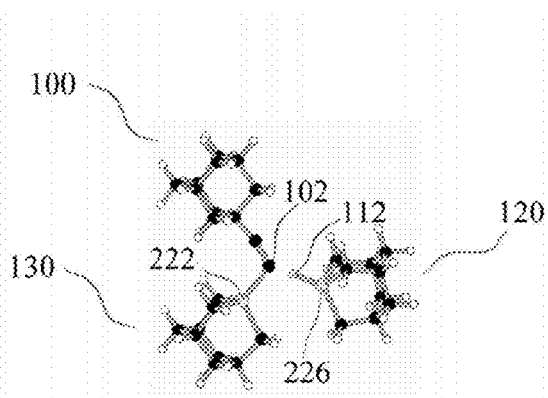
FIG. 12C shows a Germanium Radical Tool breaking bond to spent Hydrogen Abstraction Tool.
Figure 12D:
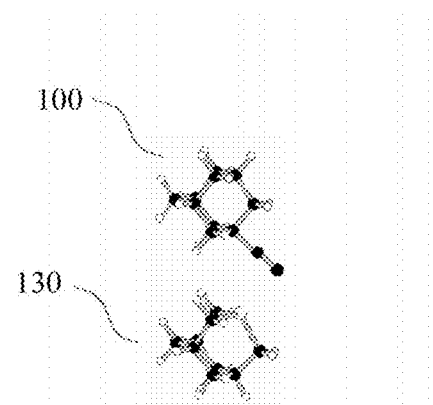
FIG. 12D shows a refreshed Hydrogen Abstraction Tool.

FIG. 12C illustrates the germanium radical 222 of the first Germanium Radical Tool 130 bonded to the distal carbon 102 of the Hydrogen Abstraction Tool 100, along with the resulting Hydrogen Donation Tool 120. When the first Germanium Radical Tool 130 is withdrawn by sufficient applied force from the Hydrogen Abstraction Tool 100, the bond between germanium atom 222 at the tip of the first Germanium Radical Tool 130 and carbon atom 102 at the tip of the Hydrogen Abstraction Tool 100 will break. The result of this mechanosynthetic reaction is illustrated in FIG. 12D, which shows the resulting refreshed Hydrogen Abstraction Tool 100 and recovery of the original Germanium Radical Tool 130 unchanged.

During mechanosynthesis, as many hydrogen atoms as desired can be added by abstracting hydrogen atoms from some convenient source (e.g., a hydrogenated diamond surface) using the Hydrogen Abstraction Tool, and then transferring the hydrogen atoms so obtained to Hydrogen Donation Tools from which they can be added to a workpiece. The reverse of this process can be used to get rid of excess hydrogen atoms by donating them to a convenient sink (e.g., a non-hydrogenated diamond surface) using a Hydrogen Donation Tool. Consequently, the sequence described above can accommodate the net addition or removal of hydrogen atoms.

Charging the GermylMethylene Tool

The discharge of a GermylMethylene Tool creates a spent GermylMethylene Tool, which is identical to a Germanium Radical Tool. A GermylMethylene Tool can be charged by starting with a Germanium Radical Tool and .CH2 groups distributed on a suitable presentation surface (e.g., germanium). The Germanium Radical Tool is touched to a .CH2 group on the presentation surface, and then withdrawn. Although the .CH2 group is bonded to a germanium atom on the presentation surface and to a germanium atom on the tip of the Germanium Radical Tool, the bond to the germanium atom on the tip of the Germanium Radical Tool is stronger (the germanium on the tip of the Germanium Radical Tool is in a different atomic bonding environment than the germanium on the presentation surface—in particular, it is bonded to 3 carbon atoms rather than being bonded to other germanium atoms).

Upon withdrawal of the tool handle from the presentation surface, the .CH2 group is withdrawn with it, thus converting the Germanium Radical Tool back into a GermylMethylene Tool, completing the recharge process.

Methylation of a Selected Site on a Diamondoid Workpiece

FIGS. 13A-E illustrate mechanosynthetic methylation of a selected atomic site. During fabrication, workpieces will frequently be hydrogenated to eliminate dangling bonds and to avoid unexpected reconstructions. Some of these hydrogenations, particularly when immediately followed by hydrogen abstraction, can simply be omitted. Because of this general assumption, the first step in the methylation sequence is to abstract a hydrogen atom from the specific site to allow addition of a CH3 group. When this general assumption is not used (i.e., when exposed radical sites are not immediately hydrogenated) there might be multiple radical sites available on the workpiece that could be methylated without first abstracting a hydrogen. In such cases, the step illustrated in FIG. 13A in the following sequence could be eliminated, and steps illustrated in FIG. 13D and FIG. 13E might also be eliminated if there is no immediate need to hydrogenate this particular added .CH2 group, leaving only steps illustrated in FIG. 13B and FIG. 13C as required for this method. The need (or lack thereof) for hydrogenation or dehydrogenation in a given case will be readily apparent to a practitioner skilled in the art.

Figure 13A:
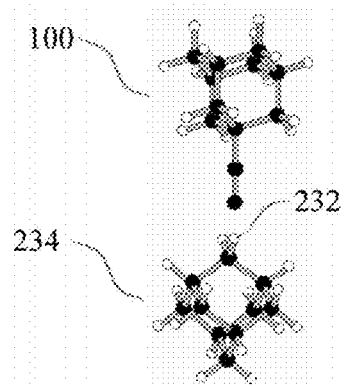
FIG. 13A shows abstracting hydrogen from a workpiece.

FIG. 13A illustrates abstracting the hydrogen atom 232 that occupies the site where the methyl group is to be placed. Hydrogen Abstraction Tool 100 abstracts hydrogen atom 232 from adamantane cage 234, which represents a few atoms from a larger diamond workpiece.

Figure 13B:
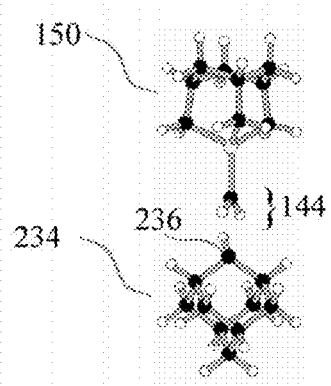
FIG. 13B shows a GermylMethylene Tool being position in close proximity to a radical carbon atom.

FIG. 13B illustrates GermylMethylene Tool 150 being positioned so that .CH2 group 144 is in close proximity to radical carbon atom 236. With the application of mechanical force to overcome reaction barriers, the .CH2 group 144 will then bond to radical carbon atom 236 as shown in FIG. 13C, the next step in the sequence.

Figure 13C:
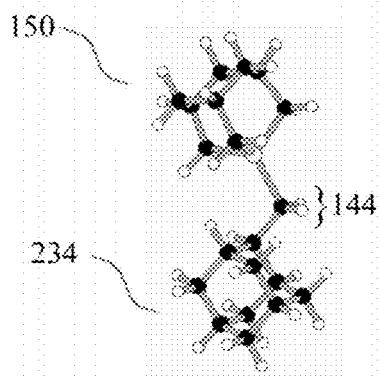
FIG. 13C shows a GermylMethylene Tool bonded to a CH2 group.

FIG. 13C illustrates the GermylMethylene Tool 150 bonded to the .CH2 group 144. The GermylMethylene Tool 150 is withdrawn by the application of mechanical force, converting GermylMethylene Tool 150 into a Germanium Radical Tool (not shown) and the .CH2 group is left behind on the workpiece 234.

Figure 13D:
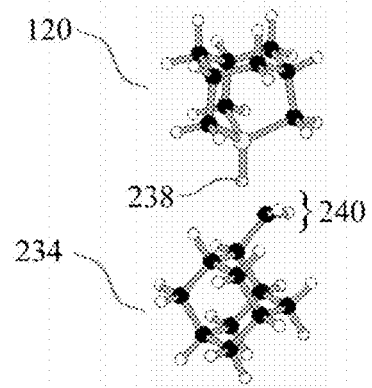
FIG. 13D shows a Hydrogen Donation Tool positioned to donate a hydrogen atom to the CH2 group.

FIG. 13D illustrates a Hydrogen Donation Tool 120 which is positioned to donate hydrogen atom 238 to the radical site on the .CH2 group 240. With the application of mechanical force to overcome reaction barriers, hydrogen atom 238 is bonded to the .CH2 group 240.

Figure 13E:
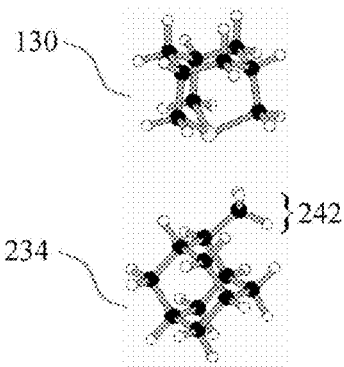
FIG. 13E shows hydrogen transferred to radical site on CH2 group and a Hydrogen Donation Tool converted into a Germanium Radical Tool.

FIG. 13E illustrates the result of the reaction in which the hydrogen on the Hydrogen Donation Tool has been transferred to the radical site on .CH2 group 240, converting it to CH3 group 242. The Hydrogen Donation Tool is converted by this process into Germanium Radical Tool 130.

This reaction sequence provides a specific example of a more general method. This method can be applied to add a methyl group to virtually any exposed carbon radical on any hydrocarbon structure. It can also be used to add a methyl group to a wide range of other possible target structures.

Ring Closure on a Diamondoid Workpiece

The addition of individual methyl groups is a versatile technique, and in conjunction with the ability to close a ring, provides a mechanism for fabricating a wide range of diamondoid structures.

Figure 14A:
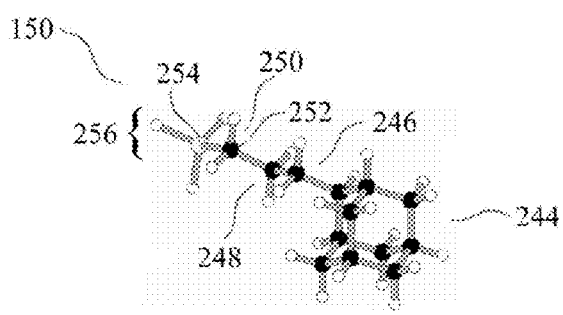
FIG. 14A shows a GermylMethylene Tool bonded to the third methylene group of a chain of three methylene groups that has been bonded to an adamantane workpiece.

FIG. 14A illustrates a structure to which three CH2 groups have already been added. The first CH2 group 246 is attached to a sidewall site on adamantane cage 244, a cage that represents a few atoms from a larger diamond workpiece. The second CH2 group 248 is added to the first CH2 group 246, and the third CH2 group 250 is added to the second CH2 group 248. The GermylMethylene Tool 150 that is used to add the third CH2 group 250 (thus incorporating the final carbon atom 252 in the chain) is not withdrawn, but instead is left attached so that this tool can be used to re-position carbon atom 252. For purposes of brevity of illustration only, the GermylMethylene Tool 150 is represented by a single germanium atom 254 and 3 attached hydrogen atoms 256, rather than the full adamantane cage structure of the GermylMethylene Tool 150 as shown in FIG. 5.

Figure 14B:
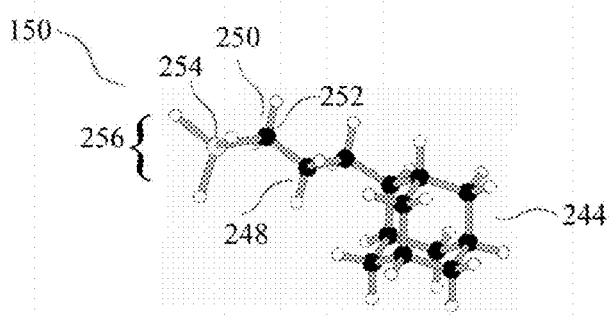
FIG. 14B shows the third methylene group rotated to a different position relative to the chain of three methylene groups attached to an adamantane workpiece, using a GermylMethylene Tool.

FIG. 14B illustrates the structure that results after CH2 group 250 has been rotated from the trans to the cis configuration relative to CH2 group 248, which is accomplished by the application of lateral forces transmitted through the handle of the attached GermylMethylene Tool 150.

Figure 14C:
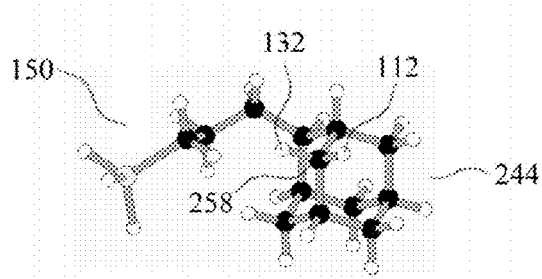
FIG. 14C shows the chain of three methylene groups rotated into a cagelike configuration relative to an adamantane workpiece, using a GermylMethylene Tool bonded to the third methylene group in the chain of three methylene groups.

FIG. 14C illustrates the structure that results after CH2 group 248 has been further rotated relative to CH2 group 246 such that the three CH2 groups 246, 248 and 250 are re-oriented into a cage-like configuration relative to the workpiece; this re-orientation is accomplished by the application of lateral forces transmitted through the handle of the attached GermylMethylene Tool 150. FIG. 14C also shows the location of hydrogen atom 132 that will be abstracted in the next reaction step, and the location of hydrogen atom 112 that will be abstracted in the next reaction step after that.

Figure 14D:
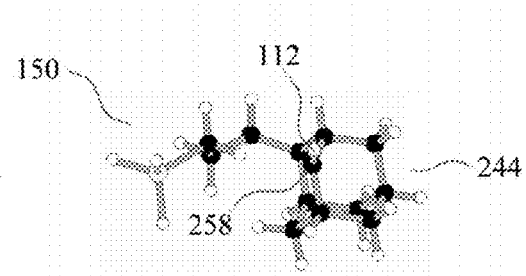
FIG. 14D shows the configuration of FIG. 14C after a first hydrogen atom has been abstracted from a sidewall carbon atom of the adamantane workpiece.

FIG. 14D illustrates the workpiece 244 after the abstraction of hydrogen atom 132 from carbon atom 258. FIG. 14D also shows the location of hydrogen atom 112 that will be abstracted in the next reaction step.

Figure 14E:
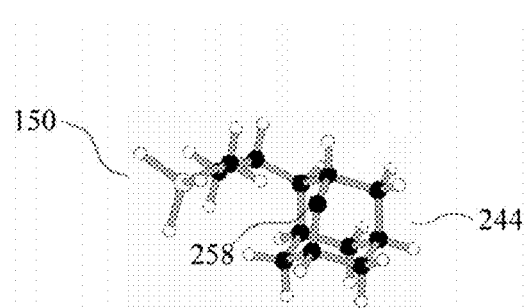
FIG. 14E shows the configuration of FIG. 14D after a second hydrogen atom has been abstracted from the same sidewall carbon atom of the adamantane workpiece.

FIG. 14E illustrates the workpiece 244 after the abstraction of a second hydrogen atom 112 from the same carbon atom 258, which becomes a carbene diradical. The two hydrogen abstractions that occur in FIG. 14D and FIG. 14E are not shown explicitly but require the use of two Hydrogen Abstraction Tools in the abstraction process.

Figure 14F:
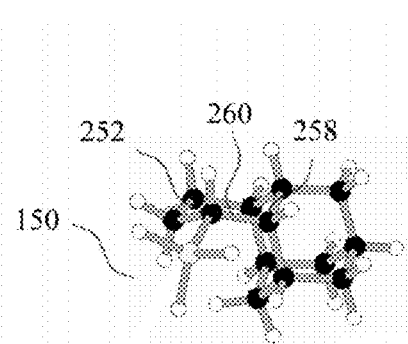
FIG. 14F shows the chain of three methylene groups bonded to a sidewall carbon atom of the adamantane workpiece, thus closing a ring of three methylene groups, with the GermylMethylene Tool still attached.

FIG. 14F illustrates GermylMethylene Tool 150 being positioned so that carbene 258 inserts into the CH bond between carbon atom 252 and one of its attached hydrogen atoms with the application of mechanical force. Following this insertion reaction, carbon atom 252 will bond to carbon atom 258 via bond 260.

Figure 14G:
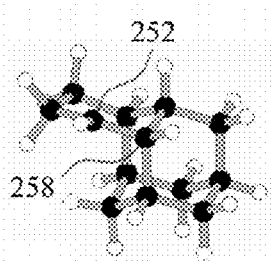
FIG. 14G shows the configuration of FIG. 14F after the GermylMethylene Tool is detached.

FIG. 14G illustrates the workpiece after the GermylMethylene Tool 150 is withdrawn, leaving carbon atom 252 attached to carbon atom 258. Carbon atom 252 is now, because of the withdrawal of GermylMethylene Tool 150, a radical.

Figure 14H:
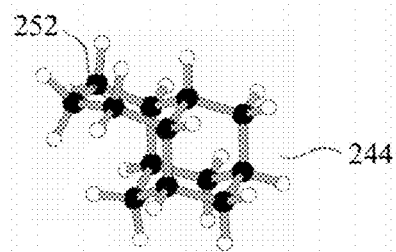
FIG. 14H shows the adamantane workpiece with a fully passivated three-methylene ring attached between two sidewall sites.

FIG. 14H illustrates the state after the final step in the mechanosynthetic reaction sequence which is to hydrogenate the radical site at carbon atom 252 using a Hydrogen Donation Tool 120 (not shown). The donation reaction, which requires the application of mechanical force to overcome a reaction barrier, is not shown explicitly but requires the use of a Hydrogen Donation Tool. Following this hydrogenation, carbon atom 252 has four bonds, two bonds to adjacent carbon atoms and two bonds to hydrogen atoms. This mechanosynthetic reaction sequence results in a closed chain of 3 carbon atoms (derived from CH2 groups 246, 248 and 250) being added to workpiece 244.

GermylMethylene Tool 150 must be positionally rotated during this sequence. An alternative method of changing the orientation of GermylMethylene Tool 150 is to perform a handle exchange, substituting a new tool in a new orientation for the existing GermylMethylene Tool 150. In this alternative method, a hydrogen atom is first abstracted from CH2 group 250 at the tip of the attached GermylMethylene Tool 150, creating a radical site at carbon atom 252 to which a new Germanium Radical Tool which is already in the desired new orientation (and precisely positioned in X, Y and Z) can next be bonded. Following this bonding, withdrawal of the GermylMethylene Tool 150 leaves the carbon atom 252 bonded to the new Germanium Radical Tool (not shown in this figure). The radical carbon atom 252 is then hydrogenated with an additional Hydrogen Donation Tool (not shown in this figure). This process effectively performs a handle exchange, with the new handle in a different orientation. This avoids the need to manipulate a single handle and change its orientation while it is attached to the workpiece, simplifying the positioning required during the ring-closing reaction sequence described above.

While the above described method of creating a ring is often useful due to its versatility, it is possible to fabricate diamond using simpler methods in some cases. In particular, in the case of mechanosynthetic manufacture of the C(110) diamond surface, methyl groups can be added on top of the troughs on the C(110) surface and then cross-bonded. This process described in more detail below (and illustrated in FIG. 19) in the context of fabricating a simple handle structure during a bootstrap process.

Building Tool Handles

Once the ability to fabricate diamond and similar hydrocarbons is achieved (using the ring closure reaction as described above, or using methylation of a C(110) diamond surface as described below, or using other reactions that would readily be apparent to someone skilled in the art and having the benefit of the teachings presented herein), atomically-precise handle structures can be fabricated that will be suitable for supporting the various tips illustrated in FIGS. 1-9.

Building Specific Tools

Figure 1B:
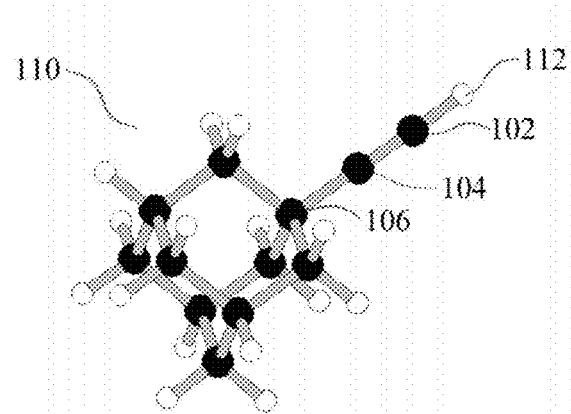
FIG. 1B is a spent Hydrogen Abstraction Tool.

Given a sufficient number of each type of the bootstrap tools, it is possible to build more of any of the nine tools. Once having built a suitable handle structure, the specific tip can be added. Reviewing the tools in order:

(1) Hydrogen Abstraction Tool. Having built the handle and the adamantane cage at the end of the handle, we then add a methyl group at the apex, followed by adding a second methyl group to the first methyl group. All but one of the hydrogen atoms on these two methyl groups are then abstracted using other Hydrogen Abstraction Tools, creating the Hydrogen Abstraction Tool in its spent version (as shown in FIG. 1B). This structure is then refreshed using the Hydrogen Abstraction Tool recharge sequence shown in FIG. 12.

(2) Hydrogen Donation Tool. We use a Germanium Radical Tool in the Hydrogen Abstraction Tool recharge sequence shown in FIG. 12 to convert the Germanium Radical Tool to a Hydrogen Donation Tool.

(3) Germanium Radical Tool. Having built the handle, we use the Germylene Tool to add the single germanium atom needed at the tip of this tool.

(4) Methylene Tool. Starting with the Adamantane Radical Tool, we bond the Adamantane Radical Tool to a .CH2 group on a suitable presentation surface (e.g., germanium) and retract the tool producing a Methylene Tool.

(5) GermylMethylene Tool. Starting with the Germanium Radical Tool, we bond the Germanium Radical Tool to a .GeH2 group on a suitable presentation surface (e.g., germanium). The reaction energetics favor transfer of the .GeH2 group to the tool from a germanium presentation surface. We then retract the tool, producing a GermylMethylene Tool.

(6) Germylene Tool. Starting with the Adamantane Radical tool, we bond the Adamantane Radical Tool to a .GeH2 on a suitable presentation surface (e.g., germanium) and retract the tool, producing a Germylene Tool.

Figure 15A:
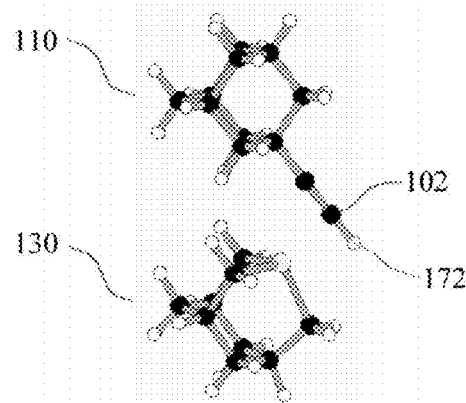
FIG. 15A shows a Germanium Radical Tool bonded to a spent Hydrogen Abstraction Tool.
Figure 15B:
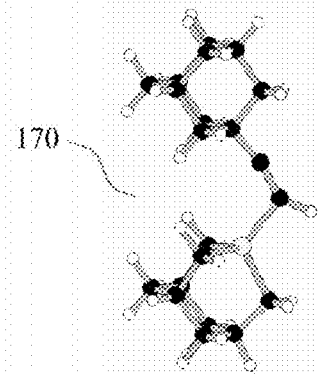
FIG. 15B shows a resulting Hydrogen Transfer Tool.

(7) Hydrogen Transfer Tool. Starting with a spent Hydrogen Abstraction Tool and a Germanium Radical Tool as shown in FIG. 15A, Germanium Radical Tool 130 is bonded to the distal carbon atom 102 of the spent Hydrogen Abstraction Tool 110 yielding Hydrogen Transfer Tool 170 as shown in FIG. 15B.

(8) Dimer Placement Tool. After fabricating a first Germanium Radical Tool, a second Germanium Radical Tool is constructed in a lonsdaleite polytype configuration on the side of the first Germanium Radical Tool, yielding a discharged Dimer Placement Tool which is then recharged with C2 dimer by the addition of two carbon atoms using two GermylMethylene Tools, followed by the abstraction of four hydrogen atoms using four applications of Hydrogen Abstraction Tools.

(9) Adamantane Radical Tool. Using the Hydrogen Abstraction, Hydrogen Donation and GermylMethylene Tools, we can build the handle structure for the Adamantane Radical Tool and the Adamantane Radical Tool itself.

Given enough Hydrogen Abstraction Tools and Hydrogen Donation Tools, we can build a limited number of Germanium Radical Tools (limited by the number of Hydrogen Donation Tools) by using the Hydrogen Donation Tools to donate hydrogen atoms to a hydrogen dump (e.g., a non-hydrogenated diamond surface). With these Germanium Radical Tools we can build and recharge GermylMethylene Tools (given the availability of a suitable presentation surface for .CH2 groups). Using these tools, and recharging the tools as needed, we can then build as many Hydrogen Abstraction Tools and as many Adamantane Radical Tools as desired (these tools are made from carbon and hydrogen only, and have no germanium).

With the availability of a suitable presentation surface for .CH2 groups, the Adamantane Radical Tools can be charged with .CH2 groups, producing as many Methylene Tools as desired. And, with the availability of a suitable presentation surface for .GeH2 groups, the Adamantane Radical Tools can be charged with .GeH2 groups, producing as many Germylene Tools as desired.

The Germylene Tools, along with the previously available tools, allows the fabrication of as many Germanium Radical Tools as desired, which in turn allows the fabrication of as many GermylMethylene Tools and as many Hydrogen Donation Tools as desired. Combining spent Hydrogen Abstraction Tools and Germanium Radical Tools allows the fabrication of as many Hydrogen Transfer Tools as desired. Finally, as many Dimer Placement Tools as desired can be fabricated using the previous tools.

Although various embodiments have been described in considerable detail above, many other embodiments are possible. For example, having fabricated a sufficient number of rechargeable atomically-precise tools, it will be apparent that other build sequences would allow the fabrication of a wide range of atomically-precise structures, and that other tools designs are readily created using the teachings herein, as are reactions to include many other elements and molecules.

Bootstrap Process

Once the first atomically-precise tools exist, they can be used to fabricate more of the self-same tools. But the first set of atomically-precise tools must be manufactured using only currently available atomically imprecise tools, or proto-tools, a process called bootstrapping. Numerous approaches exist for bootstrapping the first atomically-precise tools from proto-tools.

One approach is to synthesize appropriate molecules and then attach these (or similar molecules that have appropriate tip structure) to the tip structure of an SPM-like device to create the first proto-tools via tip functionalization; a wide range of molecular structures having the desired functionality similar to atomically-precise tools are feasible. AFM tip functionalization is well-known in the prior art. Wong, S., Woolley, A., et al. (1999) "Functionalization of carbon nanotube AFM probes using tip-activated gases." Chemical Physics Letters (306): 219-225. See also, Grandbois, M., Dettmann, W., et al. (2000) "Affinity Imaging of Red Blood Cells Using an Atomic Force Microscope." Journal of Histochemistry & Cytochemistry (48): 719-724. See also, Hafner, J., Cheung, C., et al. (2001). "Structural and Functional Imaging with Carbon Nanotube AFM Probes." Progress in Biophysics & Molecular Biology 1(77): 73-110.

Another approach is to use commercially available SPM ultra-sharp tips. This approach is described in detail below.

The present invention describes a set of nine molecular tools sufficient to make additional sets of the self-same tools (the "minimal toolset") as described above. These tools are illustrated in FIGS. 1-9. Given an adequate initial number of each of these nine tools, with the tools being positionally controlled by suitable positional devices and given suitable presentation surfaces for feedstock, it is possible to build additional sets of the self-same tools.

The first toolset, however, must be built without the benefit of a previously existing toolset. Thus, this first toolset must be fabricated from simpler proto-tools using methods that are experimentally accessible. Once such a bootstrap process has been executed, yielding a first set of tools in small but adequate numbers, the bootstrap process need not be repeated again.

Hence, each reaction sequence comprising the bootstrap process need only be carried out a small number of times. As a consequence, any methods (even those that would be too expensive or unreliable for continued use) of building the first set of tools are sufficient to enable the fabrication of more tools. These methods can be carried out at low temperature (e.g., 77K-80 K is readily available using liquid nitrogen, or 4 K using liquid helium) and by the use of proto-tools having only modest reliability. Reducing the temperature dramatically increases the number of reliable operations that are available for use during the bootstrap sequence using proto-tools, even if the resulting more sophisticated final toolset (which is fabricated by the proto-tools) is intended for use at higher temperatures.

It is possible to make the complete set of nine tools given only the Hydrogen Abstraction and Hydrogen Donation Tools. With a small but adequate initial supply of these two tools, when operated with appropriate positional control in an inert environment, and when provided with a source of feedstock (e.g., .CH2, .GeH2 and H distributed on appropriate presentation surfaces) and a hydrogen dump (a surface with a high affinity for hydrogen on which excess hydrogen would be placed, e.g., bulk-produced atomically flat clean diamond), it is possible to manufacture all nine tools. Therefore, in one embodiment of a representative bootstrap process, proto-tools are fabricated that are the functional equivalent of the Hydrogen Abstraction and Hydrogen Donation Tools.

There are many possible bootstrap sequences depending on the toolset, on the particular method of selecting an initial subset of the tools, and on the particular method of creating functional equivalents of those initial tools using existing technology. One approach is to synthesize appropriate molecules and then attach these (or similar molecules that have appropriate tip structure) to the tip structure of an SPM-like device to create the first proto-tools via tip functionalization. Another approach is using commercially available SPM ultra-sharp tips. The particular sequence described here employs existing ultrasharp silicon and diamond SPM tips.

Current ultrasharp scanning probe tips having nanometer or sub-nanometer radius of curvature, when operated at low temperature, are sufficient for the modest reliability requirements of a bootstrap sequence. Such ultrasharp scanning probe tips are commercially available, e.g., silicon tips with tip radii of 2 nm or less, and diamond-like carbon (DLC) spike-probe tips having a sub-nanometer asperity that is only a few carbon atoms wide at its distal terminus.

Bootstrap processes are simplified by following the general principle that feedstock is moved downhill in energy or bonding force as it is transferred, for example, from the feedstock presentation surface, to the tip, and finally to the workpiece. While other sequences are possible (e.g., when removing atoms from a workpiece) the principle is the same: design the combination of feedstock, tip, and workpiece so that the desired reactions are favored by the net energy change or binding force differences.

Implementing this general principle proceeds in the following stages:

(1) Distribute desired feedstock onto a presentation surface. While the feedstock bonds more weakly to the surface than to the tip (making it easy to acquire the feedstock with the tip), the feedstock bonds strongly enough to prevent problematic migration or departure from the presentation surface at the designated operating temperature.

(2) If necessary, activate the feedstock (e.g., by abstracting a hydrogen atom and making it reactive, once the first hydrogen abstraction tool is available).

(3) Bring a tip (positioned by an SPM-like apparatus or some other positional device) into contact with the activated feedstock, and bond to it with the tip, possibly requiring the application of mechanical force to overcome reaction barriers. The resulting newly formed bond is stronger than the bond that holds the feedstock to the presentation surface.

(4) Withdraw the tip, and with it withdraw the transferred feedstock from the presentation surface.

(5) Use the SPM tip to position the transferred molecule next to a workpiece, and form a bond with the feedstock and the workpiece, possibly requiring the application of mechanical force to overcome reaction barriers. For an appropriately selected workpiece and feedstock, the bond that forms between the workpiece and the cluster will be stronger than the bond between the cluster and tip.

(6) Withdraw the tip, leaving the transferred feedstock behind on the workpiece.

If the presentation surface is germanium (which forms relatively weak bonds) and the feedstock is .CH2, .GeH2 or even more simply just a single hydrogen atom H, then a silicon tip will bond to the feedstock more strongly than the germanium surface bonds to the feedstock. If the workpiece is a stiff hydrocarbon structure, the feedstock (e.g., H, .CH2, or .GeH2) will bond more strongly to a radical carbon site on the workpiece than to the silicon tip, and so can be transferred to the workpiece at a desired location. That is, the feedstock's net energy decreases, or bonding force increases, as it transfers from the presentation surface, to the tip, and finally to the workpiece.

Even when the bond strengths or energies between the feedstock, the presentation surface, the SPM tip and the workpiece are very similar, test-and-repeat steps, or other techniques can be used to obtain adequately reliable results. Such procedures are discussed in more detail herein.

Lowering the temperature can also be used to reduce the randomizing effect of thermal noise. At a sufficiently low temperature for a given reaction, thermal noise will no longer significantly disturb the outcome and the reliability of the operations is then limited by other factors.

Starting a Bootstrap Sequence: The Proto-Hydrogen Abstraction Tip

Figure 16A:
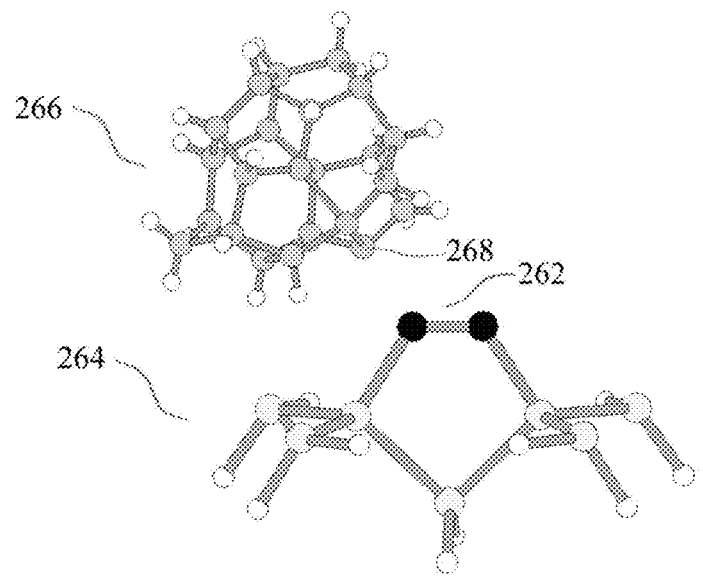
FIG. 16A shows a bootstrap sequence for a proto-Hydrogen Abstraction tip.

FIG. 16A illustrates how a bootstrap sequence may start with the fabrication of a proto-Hydrogen Abstraction tip. The proto-Hydrogen Abstraction tip 270 shown in FIG. 16B differs from the Hydrogen Abstraction Tool 100 shown in FIG. 1 in that the proto-Hydrogen Abstraction tip does not necessarily have an atomically-precise adamantane cage at the base of the ethynyl radical. It should be understood that the particular proto-Hydrogen Abstraction tip 270 is but one instance of an entire class of structures that incorporates some degree of randomness in the fabrication process but which still has the requisite properties. For the proto-Hydrogen Abstraction tip it is sufficient that the ethynyl radical is in place and functions.

One method of preparing the first proto-Hydrogen Abstraction tip is by the following five-step sequence.

(1) C2 dimers are chemisorbed onto an appropriate presentation surface. As illustrated in FIG. 16A, the preparation may begin with the direct adsorption of C2 dimers 262 onto a depassivated surface 264 (or into a matrix) which may be, among other possibilities, copper, frozen noble gases (or similarly unreactive compounds), germanium, germanium carbide, graphene, silicon carbide, or platinum.

(2) Continuing with FIG. 16A, having once obtained a suitable presentation surface with C2 dimers distributed on it, a sub-nanometer radius diamond tip 266 is at least partially depassivated by any of several methods, which might include: (A) heating to an appropriate temperature (e.g., 700-800 K for diamond C(111) and C(100) surfaces), (B) contacting the tip to an already depassivated surface (e.g., a surface with an equal or higher affinity for hydrogen), or (C) by the standard practice of applying a suitable voltage pulse to cause removal of one or more hydrogen atoms from the tip. This produces at least one radical site 268 on the tip.

(3) Continuing with FIG. 16A, the tip 266 is brought into contact with one end of a chemisorbed dimer 262, resulting in the dimer bonding to the tip, possibly requiring the application of mechanical force to overcome reaction barriers.

Figure 16B:
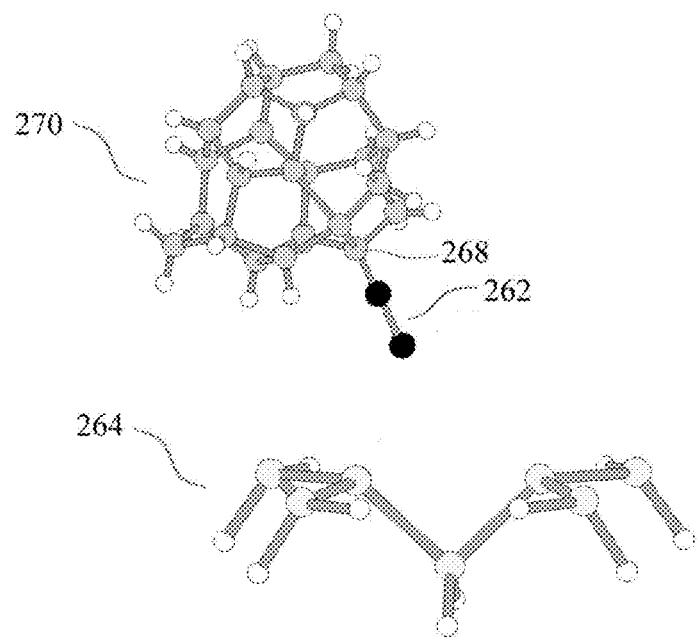
FIG. 16B shows the result when the proto-Hydrogen Abstraction tip is withdrawn from the presentation surface.

(4) Turning now to FIG. 16B, the tip is then withdrawn from the presentation surface, producing the desired proto-Hydrogen Abstraction tip 270.

(5) A "test and repeat" step may be employed to ensure that the resulting proto-Hydrogen Abstraction tip has been made successfully, if increased reliability is desired.

The resulting proto-Hydrogen Abstraction tip can then be used to selectively abstract hydrogen in subsequent mechanosynthetic steps. In addition, the minimal toolset (as described in Freitas and Merkle (2008)) reactions normally required in the recharge sequence for the proto-Hydrogen Abstraction tip are avoided during the bootstrap sequence by discarding the proto-Hydrogen Abstraction tip after a single use and making additional proto-Hydrogen Abstraction tips as needed to abstract additional hydrogen atoms. While inefficient, the above steps serve to produce a sufficient number of proto-Hydrogen Abstraction tips during the bootstrap process.

The Proto-Silicon Hydrogen Donation Tip

After creation of a proto-Hydrogen Abstraction tip, it is necessary to produce a proto-Hydrogen Donation tip. A proto-Hydrogen Donation tip will be effective at donating hydrogen atom to a carbon radical on a diamond workpiece.

The most direct method for obtaining a proto-Hydrogen Donation tip is to create an ultrasharp hydrogenated germanium tip with <2 nm radius of curvature. Ultrasharp germanium tips are not yet commercially available, but ultrasharp silicon tips are commercially available and can also be used. The hydrogenated ultrasharp silicon tip is designated as a proto-Silicon Hydrogen Donation tip. A functionally equivalent tool may substitute a silicon atom in place of germanium atom 124 in the Hydrogen Donation Tool illustrated in FIG. 2.

The primary reason for using germanium in the toolset rather than silicon is the higher reliability of operation with germanium. The substitution of a silicon tip for a germanium tip also works as required for the reactions needed during the bootstrap sequence. Silicon, being one row closer than germanium to carbon, has bond strengths to carbon atoms that are intermediate in strength between C—C bonds and C—Ge bonds. As a result the critical reactions used during the bootstrap sequence will work with silicon substituted for germanium but will have lower reliability at any given operating temperature. Lowering the temperature of operation recovers much of the foregone reliability. Thus the use of commercially available silicon tips with <2 nm radii will suffice because lower temperature operation during the bootstrap sequence is readily available, and because lower-reliability processes are tolerable during bootstrapping.

Proto-Hydrogen Abstraction tips and proto-Silicon Hydrogen Donation tips are then used to fabricate the rest of the tips in the bootstrap process, followed by all the tools in the minimal toolset as described below.

The Proto-Silicon Radical Tip

By touching the proto-Silicon Hydrogen Donation tip to the hydrogen dump (which, among other possibilities, can be a dehydrogenated atomically flat diamond surface) a hydrogen atom is donated from the proto-Silicon Hydrogen Donation tip to the diamond surface, thus creating a radical site on the tip. The resulting tip is designated as a proto-Silicon Radical tip. This provides the functionality of the Germanium Radical Tool for some or all of the bootstrap sequence.

The proto-Silicon Radical tip also may be fabricated by abstracting a hydrogen atom from the proto-Silicon Hydrogen Donation tip using the proto-Hydrogen Abstraction tip.

More generally, a wide range of possible proto-radical tips may be used, and there are many methods of manufacturing any particular tip, as for example: (1) heating a workpiece diamond, silicon or germanium tip to a temperature sufficient to drive off some of the hydrogen atoms on the tip (e.g., 700-800 K for diamond C(111) and C(100) surfaces), (2) employing the standard practice of applying a voltage pulse of appropriate magnitude and duration at the workpiece tip to remove one or more hydrogen atoms, or (3) applying a proto-Hydrogen Abstraction tip or Hydrogen Abstraction Tool to the workpiece tip.

Figure 17A:
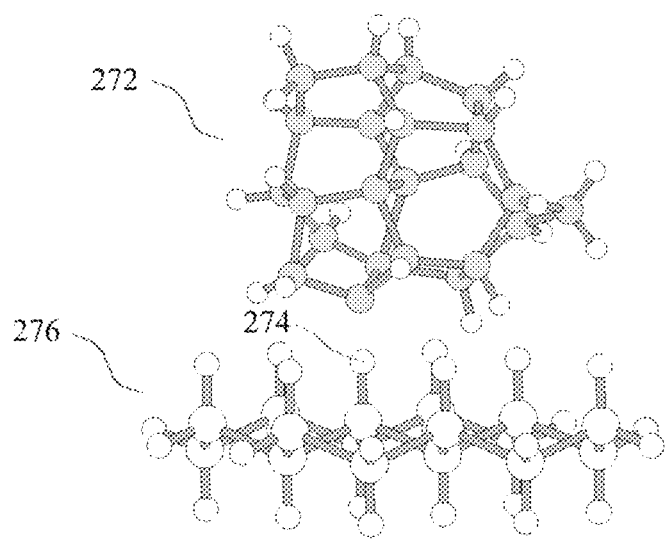
FIG. 17A shows proto-Silicon Radical tip being converted to a proto-Silicon Hydrogen Donation tip.
Figure 17B:
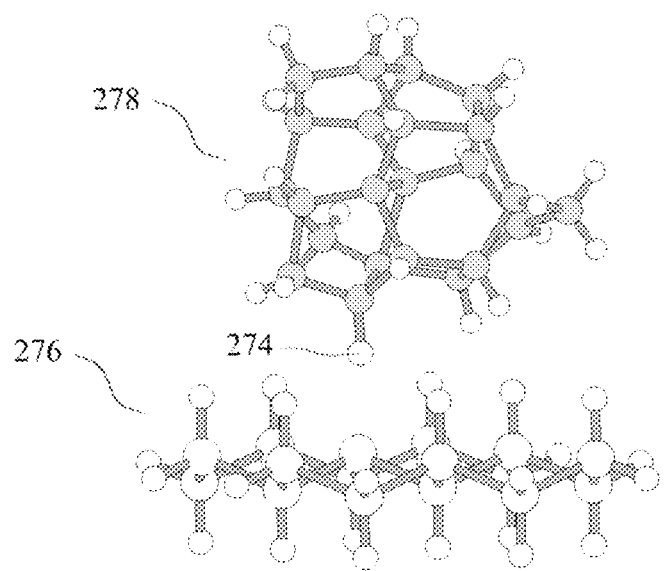
FIG. 17B shows the converted proto-Silicon Hydrogen Donation tip.

FIG. 17A illustrates the proto-Silicon Radical tip 272 being converted to the proto-Silicon Hydrogen Donation tip 278 illustrated in FIG. 17B by touching tip 272 to a hydrogen atom 274 on a suitable presentation surface 276. Of the many possible such presentation surfaces that would be suitable, an obvious choice is a hydrogenated germanium surface. This surface, upon contact by proto-Silicon Radical tip 272, transfers hydrogen atom 274 from the germanium surface 276 (where the hydrogen is more weakly bound to a germanium) to the proto-Silicon Radical tip 272 (where the hydrogen is more strongly bound to a silicon atom). The resulting proto-Silicon Hydrogen Donation tip 278 makes a suitable hydrogen donation tool.

The Proto-Silicon Methylene Tip

Once fabricated, the proto-Silicon Radical tip is touched to a .CH2 group on a suitable presentation surface to create the functional equivalent of a GermylMethylene Tool. This functional equivalent may be called a proto-Silicon Methylene tip.

Figure 18A:
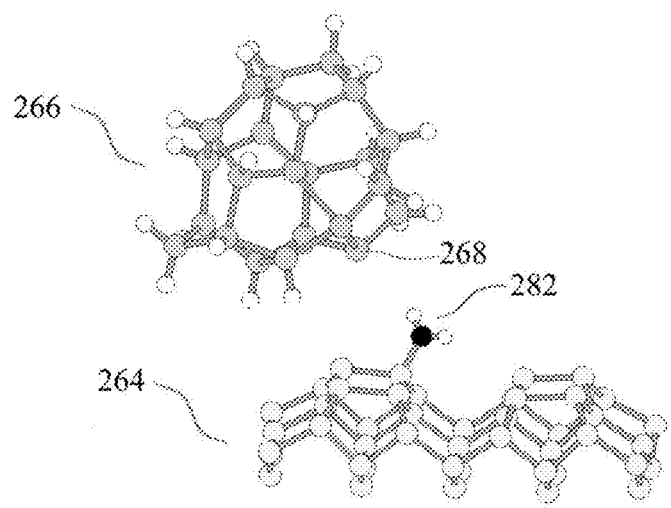
FIG. 18A shows charging a proto-Silicon Radical tip.
Figure 18B:
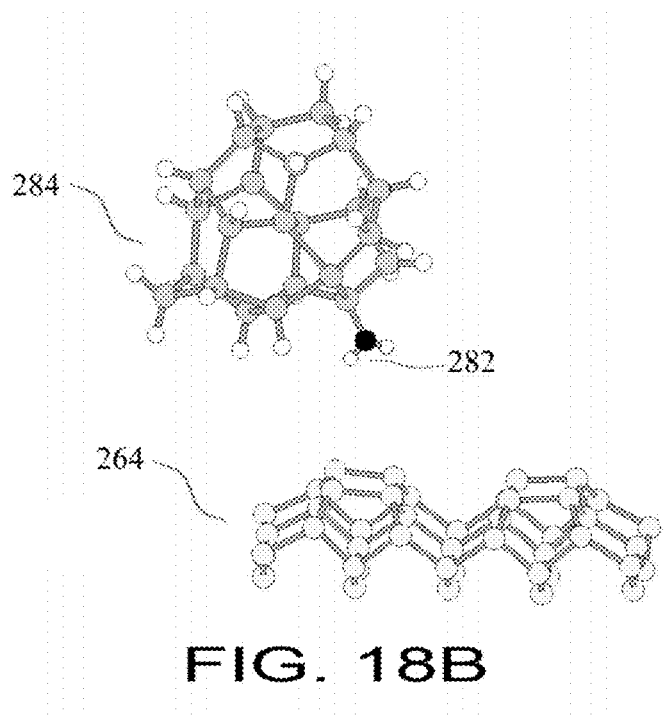
FIG. 18B shows fabrication of a proto-Silicon Methylene tip.

More generally, any radical tip, including the proto-Silicon Radical tip, can be charged by using many possible methods, as exemplified by the following series of steps illustrated by FIG. 18A:

(1) CH3 groups are distributed on a suitable presentation surface 264.
(2) A proto-Hydrogen Abstraction tip removes a selected hydrogen from a specific CH3 group chemisorbed to the presentation surface, leaving .CH2 group 282 chemisorbed to presentation surface 264.
(3) Proto-Silicon Radical tip 266 approaches .CH2 group 282 (chemisorbed to presentation surface 264).
(4) The radical site 268 on proto-Silicon Radical tip 266 bonds with .CH2 group 282 on presentation surface 264.
(5) In FIG. 18B, the proto-Silicon Methylene tip 284 is withdrawn from presentation surface 264 by the application of mechanical force, taking .CH2 group 282 with it, resulting in the fabrication of proto-Silicon Methylene tip 284 from proto-Silicon Radical tip 266. Because of the relatively low reliability and the possibility of positioning errors while using these early tips, it may be necessary to test the tip after the fifth step to determine if .CH2 group 282 has in fact attached to proto-Silicon Radical tip 284 upon its withdrawal.

This completes the fabrication of the proto-tools. The fabrication of the tools of the minimal toolset using the above-described set of proto-tools can now begin. While many of the mechanosynthesis reactions herein are generally directed towards the production of diverse, atomically-precise structures, while using the proto-tools during the bootstrap process some simplifications can be made because the objective during the bootstrap process is to manufacture a more limited set of structures; in particular, an initial set of atomically-precise tools.

Tools and Handles

Tools generally have a tip and a handle, the handle being a mounting point for the tip. In one embodiment, a suitable handle can be fabricated by starting with a small bulk-produced diamond surface. While various diamond surfaces can be used, the ring closure reactions are particularly simple when the diamond C(110) surface is used.

Figure 19A:
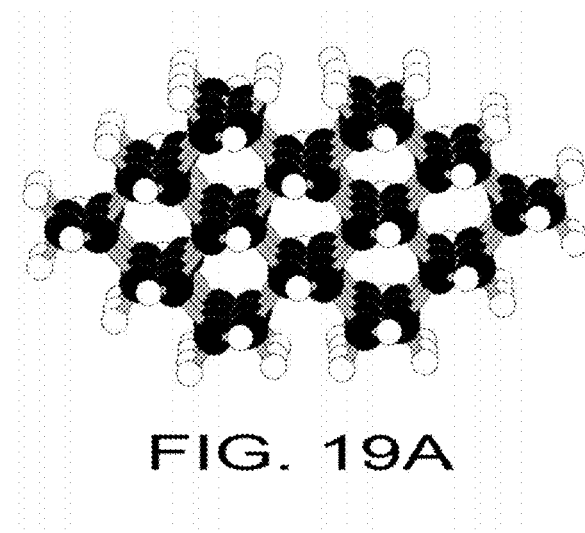
FIG. 19A shows a small section of diamond C(110) surface representing an atomically-precise workpiece upon which the C(110) surface is exposed.

FIG. 19A illustrates this surface consisting of staggered rows of atomic-scale troughs. Fabrication of additional C(110) surface takes place when a zig-zag chain of carbon atoms is emplaced straddling the length of an existing trough. Two zig-zag chains added in adjacent troughs form a new trough between them, atop which an additional chain of carbon atoms can be added. Construction of a single zig-zag chain can proceed by adding single carbon atoms to the end of the chain.

Figure 19B:
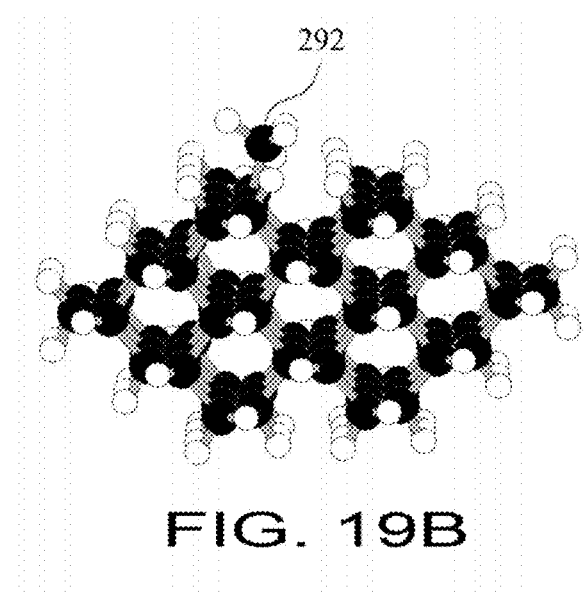
FIG. 19B shows a diamond C(110) atomically-precise workpiece surface with a CH3 group bonded to a specific atom on the left side of a trough.

Fabrication of a suitable handle using the proto-tools starting with a hydrogenated diamond C(110) surface begins as follows: (1) abstract a single hydrogen from the surface using a proto-Hydrogen Abstraction tip, creating a radical site; (2) add a .CH2 group at the radical site using a proto-Silicon Methylene tip; and (3) add a hydrogen atom to the added .CH2 group using a proto-Silicon Hydrogen Donation tip. FIG. 19B illustrates how this three-step reaction sequence adds a CH3 group containing carbon atom 292 to the left hand side of a trough on the C(110) surface.

Figure 19C:
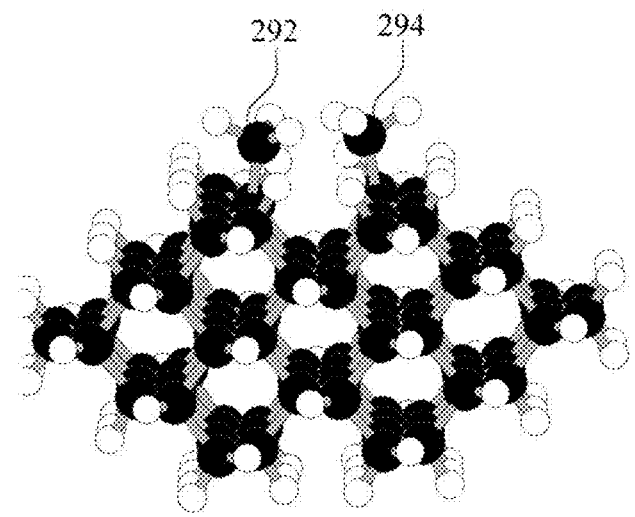
FIG. 19C shows a diamond C(110) atomically-precise workpiece surface with a CH3 group bonded to a specific atom on the left side of a trough and a second methyl group bonded to a specific neighboring atom on the right side of the same trough.
Figure 19D:
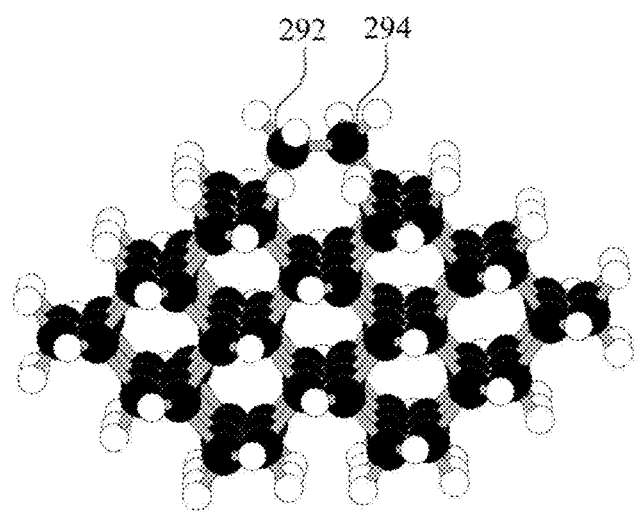
FIG. 19D shows two CH2 groups bonded across a trough on a diamond C(110) atomically-precise workpiece surface.

FIG. 19C illustrates how an additional CH3 group containing carbon atom 294 is added by the same method on the right side of the trough. After two methyl groups have been added on opposite sides of the same trough, two proto-Hydrogen Abstraction tips are applied, one to each methyl group, yielding two .CH2 groups in which both carbon 292 and carbon 294 are radicals, which then bond via radical coupling to form a single CH2CH2 group, constituting one "zig" of a zig-zag chain on the C(110) surface, as illustrated in FIG. 19D. A "zag" is then added by bonding in similar manner a third methyl group on the left hand side of the trough next to the attachment site of the first methyl group, across the trough from the attachment site of the second methyl group. A sequential application of two more proto-Hydrogen Abstraction tips to the second CH2 group and the third methyl group yields two new radical sites which then bond via radical coupling, now forming a three-carbon CH2CHCH2 "zig-zag" sequence straddling the trough of the C(110) surface. This process is continued to produce the first zig-zag chain of desired length in the lowest (most foundational) layer of the tool handle. Following the addition of this zig-zag chain, a second, third, and following chains are added in adjacent troughs on the initial C(110) surface.

This method is used to fabricate a new layer of the C(110) surface, on top of the original surface, of some specific desired size. The process is then repeated, building up a second new layer that is slightly smaller in both lateral dimensions than the first. A third layer, similarly slightly smaller than the second layer, continues this process. Additional new layers decreasing in lateral extent are fabricated until the apex of the resulting pyramid is small enough (e.g., the width of a single adamantane cage) to provide a suitable base for the intended tool whose handle is being manufactured.

The Adamantane Radical Tool

The proto-tools including the proto-Hydrogen Abstraction tip, the proto-Silicon Hydrogen Donation tip, the proto-Silicon Radical tip, and the proto-Silicon Methylene tip can be used in subsequent reactions to make the first Adamantane Radical Tool. In these reactions the proto-Hydrogen Abstraction tip would be used in place of the Hydrogen Abstraction Tool, the proto-Silicon Radical tip would be used in place of the Germanium Radical Tool, the proto-Silicon Methylene tip would be used in place of the GermylMethylene Tool, and the proto-Silicon Hydrogen Donation tip would be used in place of the Hydrogen Donation Tool.

In the case of the Adamantane Radical Tool, the tip culminates in a single bridgehead carbon atom at the apex of a pyramid structure constructed as described above. The bridgehead carbon atom apex is either manufactured in an unhydrogenated state or is dehydrogenated after manufacture using a proto-Hydrogen Abstraction tip or Hydrogen Abstraction Tool. This sequence of reactions for building the Adamantane Radical Tool is very simple because it requires only the application of a single tool or tip at a time to build the necessary handle structure. Since the handle is built layer by layer, the aspect ratio of the initial bootstrapped tips that are used during the fabrication process can be quite poor because the workpiece is geometrically accessible and all multi-tip operations are eliminated. The aspect ratio of the manufactured tools is improved during successive tool-building iterations.

Other tools are constructed by a similar sequence, but with the final apex structures and modifications thereto fabricated using a slightly different sequence of reactions. For example, the Hydrogen Abstraction Tool can be directly fabricated from the Adamantane Radical Tool, as can the Germylene Tool. It is also possible to use alternative tools, tips and processes that are less reliable at higher temperatures but which, when operated at a sufficiently low temperature, become reliable enough for use during the bootstrap process—as for example a proto-Silicon Carbene tip (which is not employed in the bootstrap process described above but could be used in an alternative process to insert a third carbon atom between two previously bonded carbon atoms in a growing diamond surface).

The Hydrogen Abstraction Tool

The Hydrogen Abstraction Tool is fabricated by touching the radical at the tip of the Adamantane Radical Tool to a C2 dimer on a suitable presentation surface.

The Methylene Tool

The Adamantane Radical Tool is also used to make the Methylene Tool by touching the radical tip of the Adamantane Radical Tool to a .CH2 group on a suitable presentation surface, in a method analogous to that used during the bootstrap procedure to fabricate the proto-Silicon Methylene tip.

The Germylene Tool and the Proto-Silicon Germanium Tip

Next, the Adamantane Radical Tool is used to make a Germylene Tool or the proto-Silicon Radical tip is used to make a proto-Silicon Germanium tip. The Germylene Tool and the proto-Silicon Germanium tip have similar functionality, so the choice about which one to use during the bootstrap sequence depends on specific issues of implementation convenience that will be evident to practitioners skilled in the art.

The Germylene Tool (or the proto-Silicon Germanium tip if fabricated) can be fabricated by touching an Adamantane Radical Tool or a proto-Silicon Radical tip (respectively) to a GeH2 group on a germanium presentation surface, in a fashion similar to the proto-Silicon Methylene tip fabrication sequence illustrated in FIG. 18 but with the .CH2 group 282 replaced by a .GeH2 group.

The Germanium Radical Tool

Either the Germylene Tool or the proto-Silicon Germanium tip can then be used during fabrication of the first Germanium Radical Tool. As the Si—Ge bond is weaker than the C—Ge bond, the reaction sequence used with the proto-Silicon Germanium tip is simpler than the reaction sequence used with the Methylene Tool.

Alternatively, the Germanium Radical Tool can be fabricated by a sequence of reactions similar to those described for the Adamantane Radical Tool and illustrated in FIG. 19, with but one exception. The single use of the proto-Silicon Methylene tip that adds the carbon atom destined to be the radical carbon at the tip of the Adamantane Radical Tool is replaced by a single use of either (1) the Germylene Tool or (2) the proto-Silicon Germanium tip, as is convenient. The remaining reactions in the sequence continue as before. As the single use of the Germylene Tool or the proto-Silicon Germanium tip is the only use of either one of these items in the entire reaction sequence required for the fabrication of the Germanium Radical Tool, the reaction reliability for this single tool application need not be high.

The GermylMethylene and Hydrogen Donation Tools

Once fabricated, the Germanium Radical Tool can be charged by touching it to a .CH2 on a suitable presentation surface, analogous to the previously described methods, producing the first GermylMethylene Tool.

The Germanium Radical Tool can also be used to make the Hydrogen Donation Tool by using the Hydrogen Abstraction recharge reaction illustrated in FIG. 12. The Hydrogen Abstraction Tool must first be used to abstract a hydrogen atom, creating a spent Hydrogen Abstraction Tool 110 requiring recharge. Then the Germanium Radical Tool 130 will bond to the spent Hydrogen Abstraction Tool 110 at the distal carbon atom 102. A second Germanium Radical Tool 224 then abstracts hydrogen 112 from the tip of the spent Hydrogen Abstraction Tool 110 to produce a new Hydrogen Donation Tool 120. The bonded Hydrogen Abstraction Tool 100 and the first Germanium Radical Tool 130 are then separated, regenerating both.

The Hydrogen Transfer and Dimer Placement Tools

As illustrated in FIG. 15, the Hydrogen Transfer Tool is fabricated by bonding a Germanium Radical Tool 130 to a spent Hydrogen Abstraction Tool 110. The Dimer Placement Tool can be made using the previous tools. The entire nine-tool minimal toolset has now been fabricated.

Summary of Bootstrap Process

The particular sequence of bootstrap operations described here is: (1) Proto-Hydrogen Abstraction tip, (2) Proto-Silicon Hydrogen Donation tip, (3) Proto-Silicon Radical tip, (4) Proto-Silicon Methylene tip, (5) Adamantane Radical Tool, (6) Hydrogen Abstraction Tool, (7) Methylene Tool, (8) Germylene Tool, (9) Proto-Silicon Germanium tip (optional), (10) Germanium Radical Tool, (11) GermylMethylene Tool, (12) Hydrogen Donation Tool, (13) Hydrogen Transfer Tool, and (14) Dimer Placement Tool. Other sequences will be apparent to practitioners skilled in the art and having the benefit of the teachings presented herein.

Bootstrapping a set of mechanosynthetic tools requires careful consideration of the reactions involved. It can be simplified by the use of additional reactions, elements, conditions, or mechanisms that are used primarily or only during the bootstrap sequence. For example, if reactions are carried out at low temperature, then reliability problems which are exacerbated by thermal noise and thermally induced errors can be reduced. Low temperature operation also allows the use of alternative reactions that might have unacceptably low reliability at higher temperatures. Auxiliary tips and processes can be introduced to simplify the steps in the bootstrap sequence. The mechanisms for providing feedstock and for disposing of excess atoms can also be chosen to simplify the bootstrap process.

Although critical in the early stages of the development of mechanosynthesis, the bootstrap process is likely to become almost immediately obsolete. Once the bootstrap proto-tools have fabricated any reasonably complete set of atomically-precise mechanosynthetic tools, this complete set of more sophisticated tools can be employed thereafter.

Energy Barriers, Tips and Reaction Design

The foregoing material has described a bootstrap process by which atomically-precise tips can be created from non-atomically-precise tips. In designing other such bootstrap processes, reactions, or tips, some useful guidelines include: use of a rigid tip geometry so that the bonds between the apical atom and the other tip atoms do not deform excessively or break as a feedstock atom is transferred; use of a tip shape and aspect ratio which allows the tip to approach a workpiece and perform the desired reaction without steric hindrance; and use of tip to feedstock bond strengths that facilitate pickup of feedstock from a feedstock depot while not making donation of feedstock to a workpiece problematic.

With regards to a rigid tip geometry, a tetrahedral structure with respect to the apical atom can be useful as, with a feedstock atom bound to one leg of the tetrahedron, the other three bonds serve to stabilize the apical atom when force is applied during a reaction. However, other geometries are possible. For example, in addition to AX4 (tetrahedral), AX5-AX8 hybridizations can also provide the necessary free electrons to bond a feedstock atom while having the ability to form at least three other bonds to create a rigid tip structure. The primary concern is simply whether or not a given tip will reliably perform the intended reaction.

To facilitate the design of new tips and reactions by example, and to provide a library of existing reactions, we have designed and tested hundreds of different tips and reactions at a high degree of simulation precision. The table below describes a large set of tips, capable of transferring many different atoms. The calculations were carried out at the B3LYP/6-311G(d,p) level of theory using the Gausian09 software package with default DFT grid size and convergence criteria. The data include net energy changes and reaction barriers to transferring many different atoms between various adamantane sidewall and bridgehead structures. These adamantine structures are used as representative tip and workpiece structures to demonstrate specific exemplary reactions that have been vetted at a high level of detail. These are certainly not the only structures and reactions that would be obvious given the teachings presented herein, but the reactions listed demonstrate transferring feedstock atoms including: Al, B, Be, Br, C, Cl, F, Ge, H, Ir, Li, Mg, N, Na, O, P, S, and Si.

With respect to the reactions in Table 1, the tip always approached the workpiece coaxially. The coaxial trajectory has been found to be widely-applicable and robust. This fact, along with the extensive data provided, should enable the facile design of a vast number of related reactions. Also, Tarasov, Akberova et al. (2010) teaches a process that may be used to determine other trajectories, and those teachings will complement the teachings present herein.

In the table below, "Tip" is the donating structure, "FS" (feedstock) is the atom being transferred, "Workpiece" is the structure to which the feedstock is transferred, "Delta (eV)" indicates the change in energy for the reaction, and "Barrier (eV)" indicates the reaction barrier.

"300K" is the probability of reaction failure at 300 Kelvin (room temperature), while "77K" is the probability at 77 Kelvin (liquid nitrogen temperature). Scientific notation is used due to the very small numbers. These calculations were performed using the formulas disclosed in Code Listing 1. 300K and 77K are representative temperatures only. Any temperature at which the reactions are reliable enough for a given purpose could be used, and it is noteworthy that most of the reactions listed would have over 99.99% reliability even at room temperature.

With respect to the structures, C9H14[Al,B,N,P] have the apical atom, to which the feedstock atom is attached, at the sidewall position of an adamantane frame. C9H15[C,Si,Ge] have the apical atom, to which the feedstock atom is attached, at the bridgehead position of an adamantane frame. The notation for the workpieces are the same, except that the apical atoms are listed first. For example, the reaction where a C914Al tip using a Be feedstock atom donates the feedstock atom to CC9H15 could be expressed as:

AdamantaneSidewall-Al-Be.+.C-AdamantaneBridge-Head→AdamantaneSidewall-Al.+.Be-C-AdamantaneBridgeHead

TABLE 1

Element Transfers with Energy Calculations and Reliabilities at Various Temperatures

| Tip | FS | Workpiece | Delta (eV) | Barrier (eV) | 77 K | 300 K |
|---|---|---|---|---|---|---|
| C9H14Al | Al | CC9H15 | −0.64 | 0.02 | 1.15E−42 | 1.72E−11 |
| C9H14Al | B | NC9H14 | −3.40 | 0.00 | 1.18E−222 | 1.09E−57 |
| C9H14Al | Be | CC9H15 | −1.46 | 0.00 | 2.39E−96 | 2.87E−25 |

TABLE 1-continued

Element Transfers with Energy Calculations
and Reliabilities at Various Temperatures

| Tip | FS | Workpiece | Delta (eV) | Barrier (eV) | 77 K | 300 K |
|---|---|---|---|---|---|---|
| C9H14Al | Be | NC9H14 | −2.71 | 0.00 | 1.14E−177 | 3.84E−46 |
| C9H14Al | H | BC9H14 | −1.05 | 0.15 | 4.94E−69 | 2.94E−18 |
| C9H14Al | H | CC9H15 | −0.90 | 0.22 | 1.77E−59 | 8.32E−16 |
| C9H14Al | H | SiC9H15 | −0.49 | 0.23 | 1.06E−32 | 6.21E−09 |
| C9H14Al | Li | NC9H14 | −0.76 | 0.00 | 1.30E−50 | 1.57E−13 |
| C9H14Al | Mg | BC9H14 | −0.22 | 0.00 | 2.48E−15 | 1.78E−04 |
| C9H14Al | Mg | NC9H14 | −0.61 | 0.00 | 1.53E−40 | 6.04E−11 |
| C9H14Al | N | BC9H14 | −1.73 | 0.04 | 6.14E−114 | 8.75E−30 |
| C9H14Al | P | BC9H14 | −0.75 | 0.14 | 1.47E−49 | 2.93E−13 |
| C9H14Al | P | NC9H14 | −0.42 | 0.00 | 4.85E−28 | 9.76E−08 |
| C9H14Al | P | SiC9H15 | −0.21 | 0.00 | 3.30E−14 | 3.47E−04 |
| C9H14Al | S | BC9H14 | −0.90 | 0.00 | 2.69E−59 | 9.27E−16 |
| C9H14B | Al | CC9H15 | −0.13 | 0.00 | 3.72E−09 | 6.86E−03 |
| C9H14B | Be | NC9H14 | −1.26 | 0.00 | 4.21E−83 | 7.19E−22 |
| C9H14B | Li | NC9H14 | −0.78 | 0.00 | 5.61E−52 | 7.01E−14 |
| C9H14B | Na | NC9H14 | −0.13 | 0.00 | 3.15E−09 | 6.58E−03 |
| C9H14N | Br | AlC9H14 | −2.48 | 0.00 | 7.75E−163 | 2.46E−42 |
| C9H14N | S | AlC9H14 | −0.65 | 0.02 | 1.95E−43 | 1.09E−11 |
| C9H14N | S | BC9H14 | −1.55 | 0.00 | 5.25E−102 | 1.01E−26 |
| C9H14N | S | SiC9H15 | −0.41 | 0.11 | 2.18E−27 | 1.44E−07 |
| C9H14P | Al | NC9H14 | −1.67 | 0.07 | 6.91E−110 | 9.60E−29 |
| C9H14P | Mg | AlC9H14 | −0.05 | 0.00 | 6.87E−04 | 1.54E−01 |
| C9H14P | Mg | BC9H14 | −0.27 | 0.02 | 1.71E−18 | 2.75E−05 |
| C9H14P | P | BC9H14 | −0.87 | 0.07 | 1.31E−57 | 2.51E−15 |
| C9H15C | Br | AlC9H14 | −1.23 | 0.01 | 3.73E−81 | 2.27E−21 |
| C9H15C | Br | BC9H14 | −1.50 | 0.00 | 1.44E−98 | 7.71E−26 |
| C9H15C | Br | GeC9H15 | −0.60 | 0.06 | 5.25E−40 | 8.28E−11 |
| C9H15C | Br | SiC9H15 | −1.01 | 0.04 | 1.27E−66 | 1.22E−17 |
| C9H15C | Cl | AlC9H14 | −1.22 | 0.17 | 9.07E−81 | 2.86E−21 |
| C9H15C | Cl | BC9H14 | −1.62 | 0.18 | 8.02E−107 | 5.87E−28 |
| C9H15C | Cl | GeC9H15 | −0.52 | 0.32 | 1.27E−34 | 2.00E−09 |
| C9H15C | Cl | SiC9H15 | −1.02 | 0.21 | 1.29E−67 | 6.79E−18 |
| C9H15C | Li | NC9H14 | −1.06 | 0.00 | 6.19E−70 | 1.72E−18 |
| C9H15C | Mg | NC9H14 | −0.61 | 0.00 | 8.90E−41 | 5.25E−11 |
| C9H15C | O | BC9H14 | −2.68 | 0.00 | 1.58E−175 | 1.36E−45 |
| C9H15C | S | AlC9H14 | −0.88 | 0.00 | 2.90E−58 | 1.71E−15 |
| C9H15C | S | BC9H14 | −1.78 | 0.00 | 7.93E−117 | 1.59E−30 |
| C9H15C | S | GeC9H15 | −0.24 | 0.00 | 2.11E−16 | 9.47E−05 |
| C9H15C | S | NC9H14 | −0.23 | 0.00 | 1.49E−15 | 1.56E−04 |
| C9H15C | S | SiC9H15 | −0.63 | 0.00 | 3.25E−42 | 2.25E−11 |
| C9H15Ge | Br | AlC9H14 | −0.63 | 0.11 | 7.10E−42 | 2.75E−11 |
| C9H15Ge | Br | BC9H14 | −0.90 | 0.14 | 2.73E−59 | 9.31E−16 |
| C9H15Ge | Br | SiC9H15 | −0.41 | 0.21 | 2.39E−27 | 1.47E−07 |
| C9H15Ge | C | CC9H15 | −1.15 | 0.00 | 9.46E−76 | 5.54E−20 |
| C9H15Ge | C | SiC9H15 | −0.46 | 0.00 | 7.39E−31 | 1.85E−08 |
| C9H15Ge | Cl | AlC9H14 | −0.71 | 0.31 | 7.12E−47 | 1.43E−12 |
| C9H15Ge | Cl | SiC9H15 | −0.51 | 0.47 | 1.00E−33 | 3.39E−09 |
| C9H15Ge | F | AlC9H14 | −1.08 | 0.01 | 2.00E−71 | 7.15E−19 |
| C9H15Ge | F | BC9H14 | −1.79 | 0.18 | 1.19E−117 | 9.76E−31 |
| C9H15Ge | Ge | CC9H15 | 0.02 | 0.00 | 6.18E−02 | 4.89E−01 |
| C9H15Ge | H | SiC9H15 | −0.35 | 0.23 | 1.12E−23 | 1.29E−06 |
| C9H15Ge | Li | NC9H14 | −0.46 | 0.00 | 1.62E−30 | 2.26E−08 |
| C9H15Ge | O | BC9H14 | −2.96 | 0.00 | 3.94E−194 | 2.29E−50 |
| C9H15Ge | O | SiC9H15 | −0.96 | 0.00 | 9.41E−64 | 6.66E−17 |
| C9H15Ge | P | BC9H14 | −0.79 | 0.03 | 5.05E−52 | 6.82E−14 |
| C9H15Ge | S | BC9H14 | −1.54 | 0.15 | 3.71E−101 | 1.67E−26 |
| C9H15Ge | Si | CC9H15 | −0.21 | 0.00 | 3.21E−14 | 3.44E−04 |
| C9H15Si | Al | CC9H15 | −0.25 | 0.02 | 4.97E−17 | 6.54E−05 |
| C9H15Si | B | CC9H15 | −1.12 | 0.14 | 4.39E−74 | 1.48E−19 |
| C9H15Si | Br | BC9H14 | −0.49 | 0.43 | 1.13E−32 | 6.31E−09 |
| C9H15Si | H | BC9H14 | −0.56 | 0.27 | 4.65E−37 | 4.73E−10 |
| C9H15Si | Li | NC9H14 | −0.57 | 0.00 | 5.33E−38 | 2.71E−10 |
| C9H15Si | P | BC9H14 | −0.54 | 0.16 | 4.44E−36 | 8.44E−10 |
| C9H15Si | S | BC9H14 | −1.14 | 0.00 | 2.44E−75 | 7.07E−20 |
| C9H15Si | Si | CC9H15 | −0.11 | 0.00 | 6.11E−08 | 1.41E−02 |
| C9H15Si | Ge | CC9H15 | −0.08 | 0.00 | 5.83E−06 | 4.53E−02 |
| C9H15Ge | Ir | CC9H15 | −0.04 | 0.00 | 1.97E−03 | 2.02E−01 |
| C9H15Ge | Ir | SiC9H15 | −0.33 | 0.00 | 1.82E−22 | 2.63E−06 |
| C9H15C | Ir | SiC9H15 | −0.29 | 0.00 | 9.36E−20 | 1.31E−05 |
| C9H15C | Ir | BC9H14 | −1.07 | 0.00 | 6.78E−71 | 9.77E−19 |

Note that it is possible for the change in energy (eV) to be positive. This is due to the fact that energy and force are not equivalent. A mechanosynthetic tip may exert force over a distance that results in a net change in energy which is positive, even if the reaction product resides in a local energy minima.

Workpiece Specification and Build Sequences

The ability to create atomically-precise tips from non-atomically-precise tips via a bootstrap process has been described in detail herein. And, reaction energetics and reliabilities from detailed simulations have been reported which, when coupled with the teachings presented herein, would enable one skilled in the art to make many tips sufficient for carrying out many reactions. With those tips and reactions available, to facilitate building a workpiece, once must define the workpiece in an atomically-precise manner, and then create a build sequence for assembling the workpiece.

One defines a workpiece for mechanosynthesis by specifying each atom in the workpiece and its atomic coordinates, directly or indirectly (for example, via an algorithm which generates the desired structure). Many computational chemistry programs allow the creation of models based on atomic coordinates, or algorithms to generate such coordinates.

Once the atomic coordinates have been specified, a build sequence can be created that specifies the order in which each atom is to be added to, or removed from, the workpiece. Reactions that do not add or remove atoms are also possible, such as those that change the bonding structure of the workpiece. For each reaction, the reaction parameters, including the tip, tip trajectory, feedstock, reaction temperature, and possible reaction pathologies are determined. These topics are addressed herein. Where additional reactions are desired beyond those that we present, it will be obvious to one skilled in the art how to determine new reactions using the teachings and data herein as a guide.

Exemplary Workpiece Specification and Build Sequence

Figure 30:
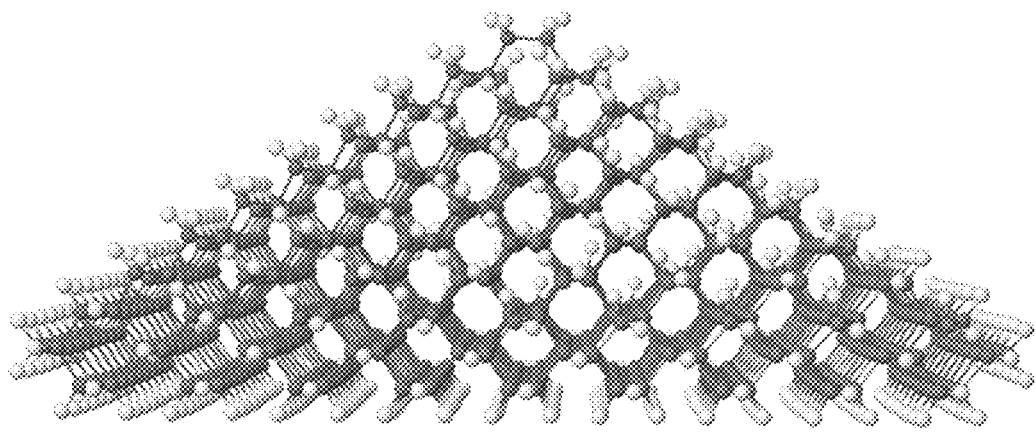
FIG. 30 shows one form of a complete pyramidal structure, the uppermost atom being Carbon.
Figure 32:
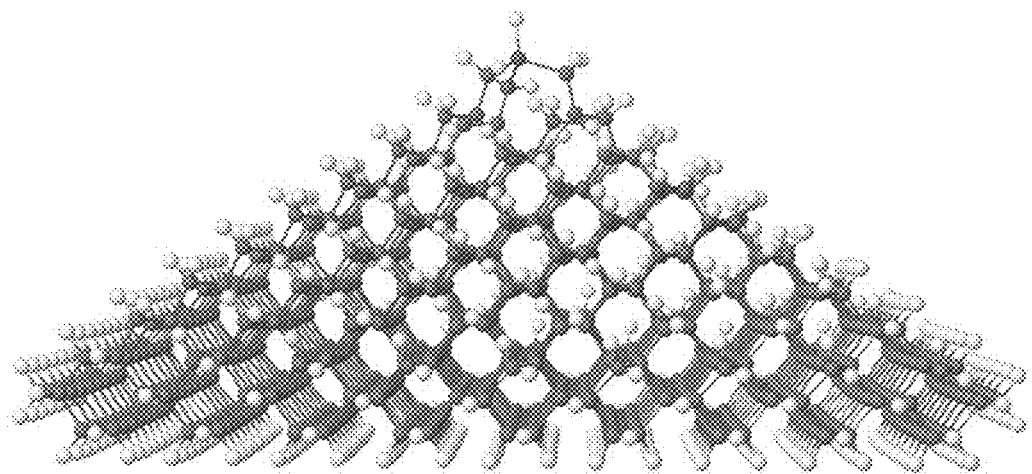
FIG. 32 shows another form of a complete pyramidal structure, the uppermost atom being Germanium.

The following illustrates the use of a build sequence for the manufacture of a pyramidal diamondoid structure in two forms (FIG. 32, which is capped with C, and FIG. 30, which is capped with Ge). This structure has multiple uses. With the apical Ge atom, it can serve as a Germanium Radical tool. Terminated with a carbon ring-closure reaction, omitting the Ge, the structure can serve as an Adamantane Radical tool. And, given the size and stepped nature of the walls, such a structure (or multiple such structures built a known distance apart) could serve as calibration standards for SFM or AFM-based metrology.

This build sequence was computed using the representative density functional method with the B3LYP/6-311G** basis set, which typically provides a good tradeoff between accuracy and computational expense. Higher reaction accuracies could be obtained using more computationally-demanding techniques such as coupled clusters. Lee, Lee, T. J., Scuseria, G. E., et al. (1995) Achieving Chemical Accuracy with Coupled-Cluster Theory. Quantum Mechanical Electronic Structure Calculations with Chemical Accuracy. Langhoff, Kluwer Academic Publisher: 47-108. 4 degrees Kelvin was assumed for this sequence (readily accessible with liquid helium) although the reactions would likely prove reliable at higher temperatures.

Workpiece Specification

A partial list of the atomic coordinates for the pyramid structure (in the Ge-capped variant) follows, though this data could take many forms. This is an excerpt of a .hin file, which may be read with, among other molecular modeling programs, Jmol. A CD containing data for molecular models in .hin format, containing 33 files totaling 814 KB, representing the molecular models shown in FIGS. 24-56, has been included with this application and is incorporated herein by reference.

Sample .hin code listing, abbreviated:
forcefield mm+
sys 0 0 1
seed −1111
mol 1
atom 1—C**-0 −7.03574 3.29651 −0.1345 4 2 s 35 s 187 s 515 s
atom 2—C**-0 −7.98407 2.0312 −0.139 4 1 s 12 s 36 s 526 s
atom 3—C**-0 −8.01136 2.01224 −2.63703 4 12 s 32 s 38 s 509 s
atom 4—C**-0 −9.91319 −1.78661 −1.41303 4 5 s 20 s 42 s 43 s
atom 5—C**-0 −8.97637 −0.52125 −1.41757 4 4 s 18 s 28 s 34 s
atom 6—C**-0 −2.41489 3.23247 −1.45796 4 11 s 26 s 39 s 216 s
atom 7—C**-0 −2.44921 0.6718 −1.4702 4 13 s 23 s 39 s 40 s
[ . . . lines removed . . . ]
atom 1392—H**-0 2.04155 1.28193 11.0572 1 1393 s
atom 1393—C**-0 1.46283 0.508671 10.5073 4 1391 s 1392 s 1382 s 1397 s
atom 1394—H**-0 −2.39766 −0.515024 11.0477 1 1396 s
atom 1395—H**-0 −1.10132 −1.6135 10.6541 1 1396 s
atom 1396—C**-0 −1.49431 −0.602855 10.405 4 1394 s 1395 s 1375 s 1397 s
atom 1397—Ge**-0-0.338415 0.785752 11.0787 4 1396 s 1389 s 1393 s 1398 s
atom 1398—H**-0 −0.446381 0.997928 12.5895 1 1397 s
endmol 1

Required Tools

The tools used in this build sequence are described in detail elsewhere herein. They are: the Hydrogen Abstraction tool (HAbst), the Hydrogen Donation tool (HDon), the Germanium Radical tool (GeRad), and the GermylMethylene tool (GM).

Required Reactions

The following reactions are used, along with the specified tools, in the building of this workpiece. In the reaction names, a reaction starting with "C" indicates a "Capping" reaction, an "M" indicates a methylating reaction, and an "R" indicates a "Row Building" reaction. Note that, since these reactions are used in sequence with each other to build the structure, the ending structure for one reaction is frequently the starting structure for another reaction.

The related figures for each reaction show only the atoms proximate to the reaction, rather than the entire workpiece. Recharge reactions are not included, but are presumed to be used as needed, as described in detail elsewhere herein. Tips are not shown as part of the reaction structures, but are listed with each reaction in the text.

TABLE 2

Figure 33:
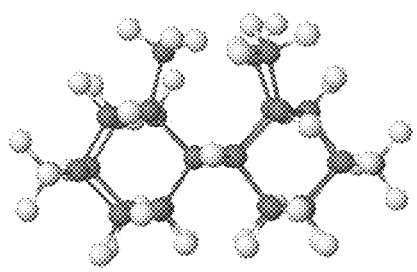
FIG. 33 shows a starting structure for reaction C002.
Figure 34:
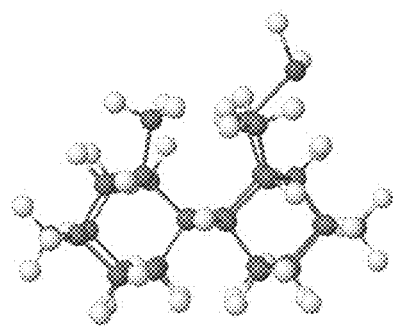
FIG. 34 shows a starting structure for reaction C004.
Figure 35:
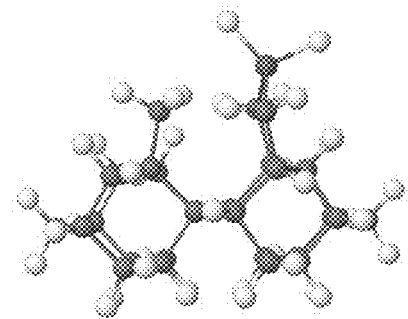
FIG. 35 shows a starting structure for reaction C006.
Figure 36:
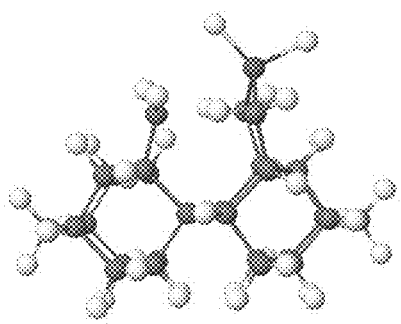
FIG. 36 shows a starting structure for reaction C008.
Figure 37:
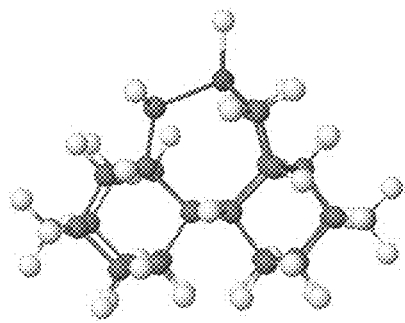
FIG. 37 shows an ending structure for reaction C008.
Figure 38:
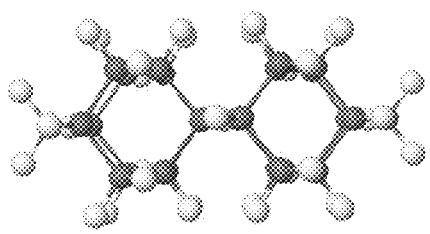
FIG. 38 shows a starting structure for reaction M002.
Figure 39:
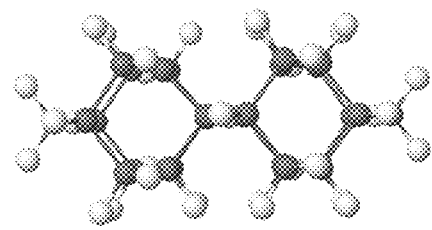
FIG. 39 shows a starting structure for reaction M004.
Figure 40:
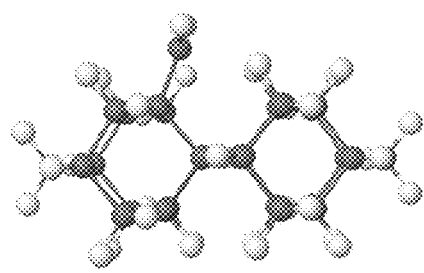
FIG. 40 shows a starting structure for reaction M006.
Figure 41:
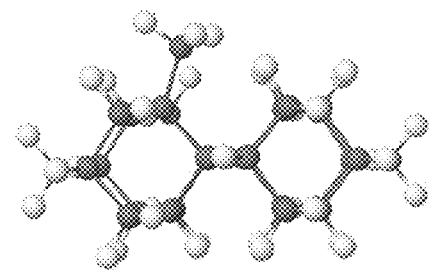
FIG. 41 shows a starting structure for reaction M008.
Figure 42:
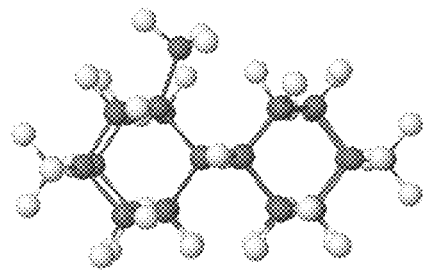
FIG. 42 shows an ending structure for reaction M008.

| Reaction | Description | Tool(s) Required | Starting Structure | Ending Structure |
| --- | --- | --- | --- | --- |
| C002 | Following three methylation steps, this is the initial step in capping the C110 pyramid with a 'GeRad' tip, via donating a radical GeH2 group to a radical methyl group on a non-outer edge carbon site with the GeRad tool, for subsequent ring closure. | GeRad | FIG. 33 | FIG. 34 |
| C004 | The second step in capping the C110 pyramid with a 'GeRad' tip, via abstracting a hydrogen from a methyl group on a non-outer edge carbon site with the HAbst tool, allowing for radical-radical coupling to close a 7-member ring on the C110 ridge. | HAbst | FIG. 34 | FIG. 35 |
| C006 | The third step in capping the C110 pyramid with a 'GeRad' tip, via abstracting a hydrogen from the third methyl group on a non-outer edge carbon site adjacent to the 7-member ring spanning the C110 ridge with the HAbst tool, for subsequent cage closure. | HAbst | FIG. 35 | FIG. 36 |
| C008 | The final step in capping the C110 pyramid with a 'GeRad' tip, via abstracting a hydrogen from the germanium of the 7-member ring spanning the C110 ridge via the HAbst tool, allowing for radical-radical coupling to close the ring. | HAbst | FIG. 36 | FIG. 37 |
| M002 | The initial step in methylating a non-outer edge carbon site, via abstracting the hydrogen from the carbon with the HAbst tool, for the subsequent addition of a radical methyl group. | HAbst | FIG. 38 | FIG. 39 |
| M004 | The second step in methylating a non-outer edge carbon site, via donating the radical methyl group to the radical carbon site with the GM tool, for subsequent hydrogenation. | GM | FIG. 39 | FIG. 40 |
| M006 | The final step in methylating a non-outer edge carbon site, via donating a hydrogen to the radical methyl group with the HDon tool. | HDon | FIG. 40 | FIG. 41 |
| M008 | The initial step in methylating an outer edge carbon site adjacent to a methylated non-outer edge carbon site, via abstracting the | HAbst | FIG. 41 | FIG. 42 |

TABLE 2-continued

Figure 43:
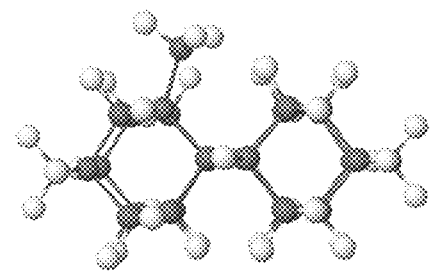
FIG. 43 shows a starting structure for reaction M009.
Figure 44:
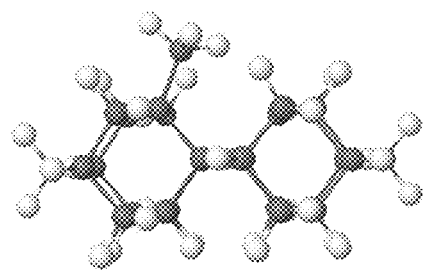
FIG. 44 shows an ending structure for reaction M009.
Figure 45:
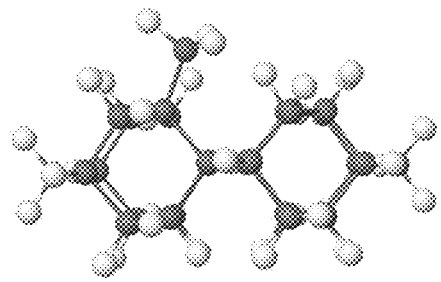
FIG. 45 shows a starting structure for reaction M011.
Figure 46:
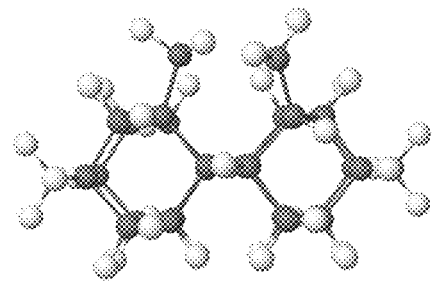
FIG. 46 shows an ending structure for reaction M011.
Figure 47:
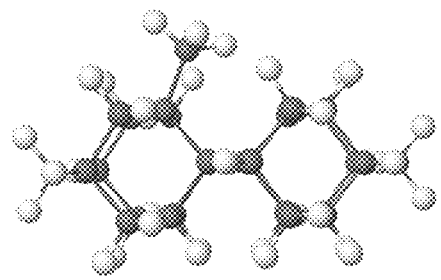
FIG. 47 shows a starting structure for reaction M012.
Figure 48:
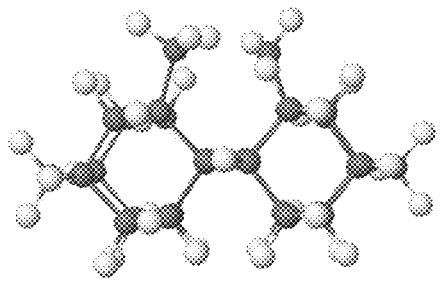
FIG. 48 shows an ending structure for reaction M012.
Figure 49:
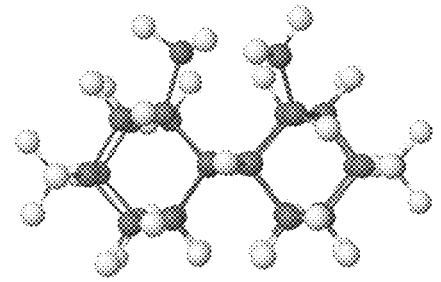
FIG. 49 shows a starting structure for reaction M014.
Figure 50:
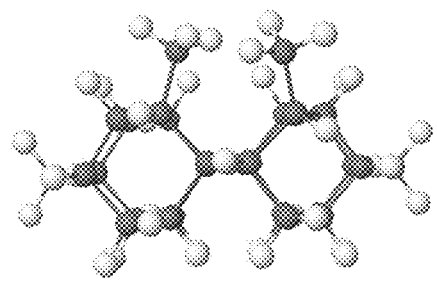
FIG. 50 shows an ending structure for reaction M014.
Figure 51:
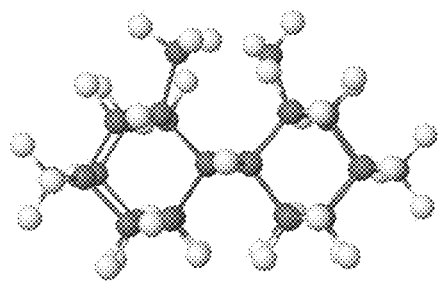
FIG. 51 shows a starting structure for reaction R003.
Figure 52:
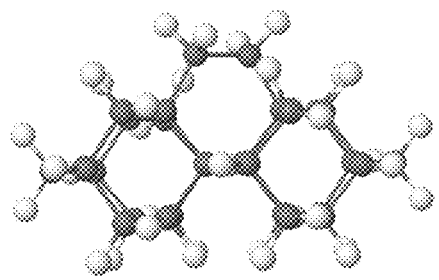
FIG. 52 shows an ending structure for reaction R003.
Figure 53:
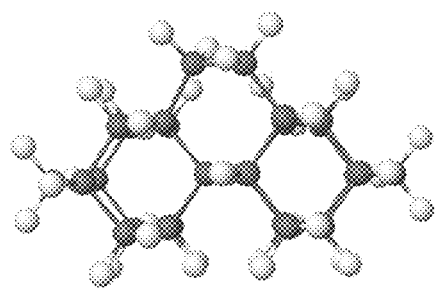
FIG. 53 shows a starting structure for reaction R004.
Figure 54:
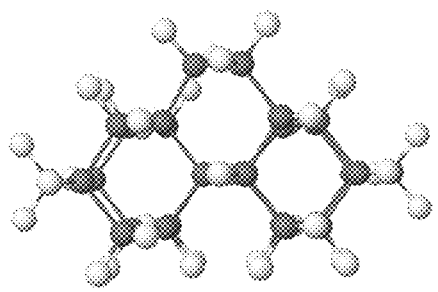
FIG. 54 shows a starting structure for reaction R005.
Figure 55:
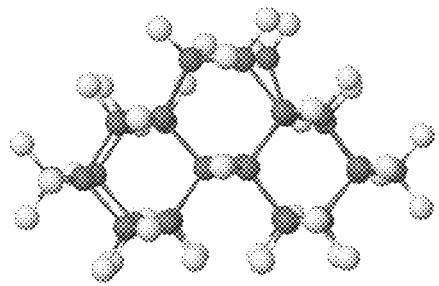
FIG. 55 shows a starting structure for reaction R006.
Figure 56:
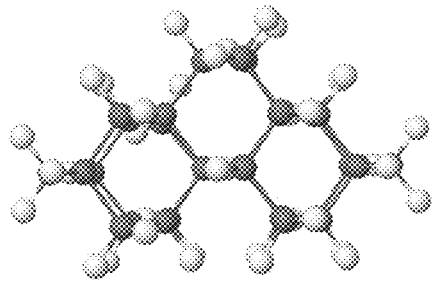
FIG. 56 shows an ending structure for reaction R006.

| Reaction | Description | Tool(s) Required | Starting Structure | Ending Structure |
|---|---|---|---|---|
| | hydrogen from the carbon with the HAbst tool, for the subsequent addition of a radical methyl group. | | | |
| M009 | The initial step in methylating a non-outer edge carbon site adjacent to a methylated non-outer edge carbon site, via abstracting the hydrogen from the carbon with the HAbst tool, for the subsequent addition of a radical methyl group. | HAbst | FIG. 43 | FIG. 44 |
| M011 | The second step in methylating an outer edge carbon site adjacent to a methylated non-outer edge carbon site, via donating a radical methyl group to the radical carbon site with the GM tool, for subsequent hydrogenation. | GM | FIG. 45 | FIG. 46 |
| M012 | The second step in methylating a non-outer edge carbon site adjacent to a methylated non-outer edge carbon site, via donating a radical methyl group to the radical carbon site with the GM tool, for subsequent hydrogenation. | GM | FIG. 47 | FIG. 48 |
| M014 | The final step in methylating an outer edge carbon site adjacent to a methylated non-outer edge carbon site, via donating a hydrogen to the radical methyl group with the HDon tool. | HDon | FIG. 49 | FIG. 50 |
| R003 | Ring closure step between radical methyl group on a non-outer edge carbon site and a methyl group on a non-outer edge carbon site, via abstracting a hydrogen from the methyl group with the HAbst tool, allowing radical-radical coupling to form a 6-member ring. | HAbst | FIG. 51 | FIG. 52 |
| R004 | The initial step in extending a C110 row, via abstracting a hydrogen from non-outer edge carbon with the HAbst tool, for the subsequent addition of a radical methyl group. | HAbst | FIG. 53 | FIG. 54 |
| R005 | The second step in extending a C110 row, via donating a radical methyl group to the radical carbon site with the GM tool, for the subsequent ring closure step. | GM | FIG. 54 | FIG. 55 |
| R006 | The final step in extending a C110 row, via abstracting a hydrogen from the existing adjacent 6-member ring with the HAbst tool, allowing for radical-radical coupling to close another 6-member ring. | HAbst | FIG. 55 | FIG. 56 |

Order of Reactions

These reactions listed above are used in specific, often iterated, sequences, to build the pyramid. FIGS. 24-32 illustrate the process, and are described in detail below.

Figure 24:
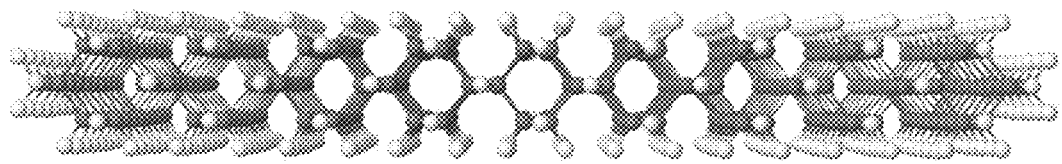
FIG. 24 shows the starting surface for a pyramid build sequence.
Figure 25:
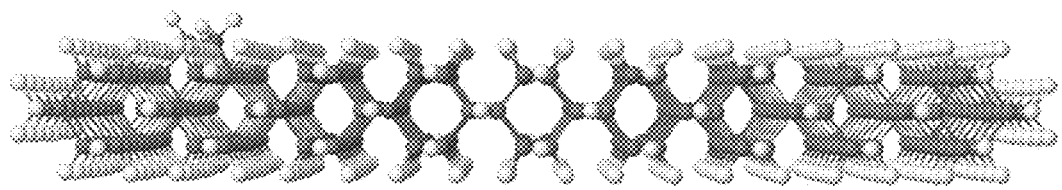
FIG. 25 shows the results of one application of a row-building sequence used to create pyramid-like structures.
Figure 26:
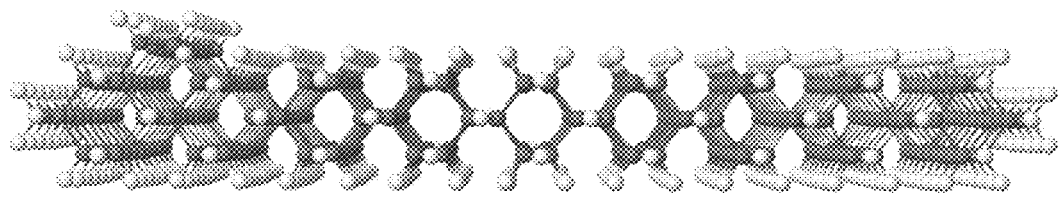
FIG. 26 shows the results of repeated applications of a row-building sequence to form a complete row.
Figure 27:
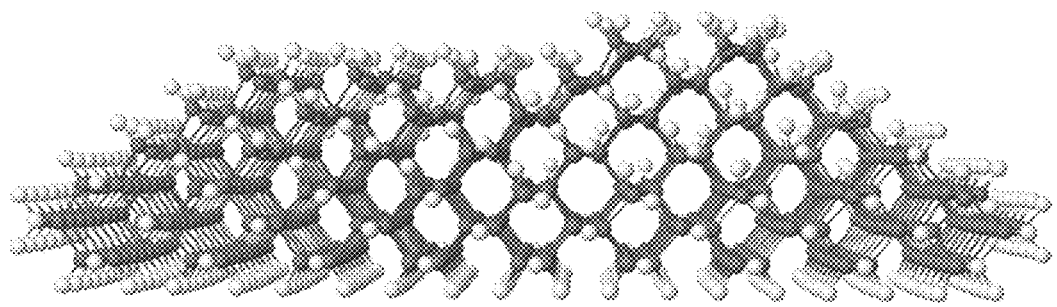
FIG. 27 shows the results of repeated applications of a row building sequence to generate multiple layers.
Figure 28:
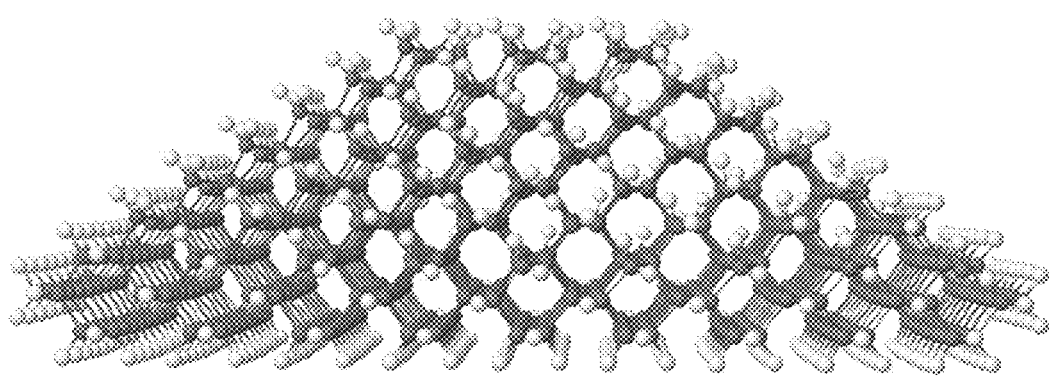
FIG. 28 shows the results of repeated applications of a row building sequence, resulting in multiple complete layers.

FIG. 24 illustrates a starting surface of C110 carbon. To start building the pyramid structure, new rows are added to the surface beginning with the following reaction sequence:

M002→M004→M006→M009→M012→R003→ R004→R005→R006

Once a new row is started, this row is extended by repeating this sequence as many times as needed:

R004→R005→R006

Successive applications of these sequences result in the structures shown in FIG. 25, FIG. 26, FIG. 27, FIG. 28, and FIG. 29, which show the structure at progressive states of completion.

Figure 29:
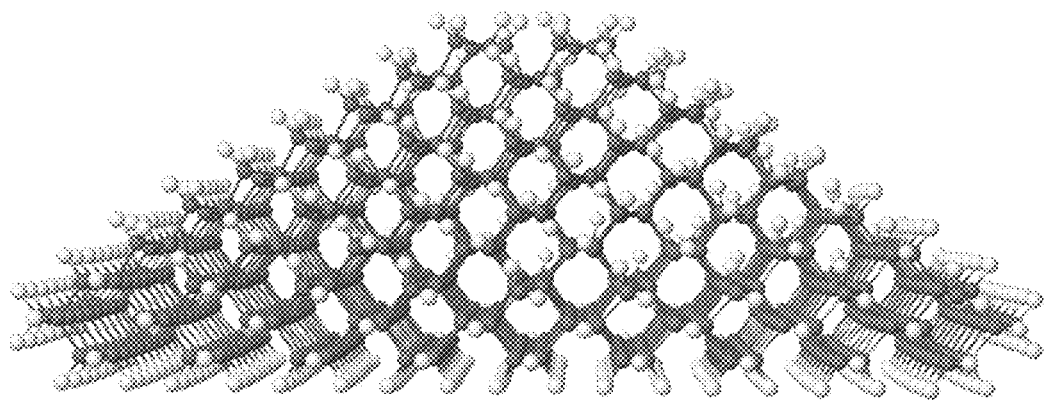
FIG. 29 shows a nearly-complete pyramidal structure.

The final set of reactions differs depending on whether Carbon or Germanium is desired as the apical atom. We illustrate both for diversity, and because this allows the creation of two different tools. Capping the pyramid with Carbon is illustrated in FIGS. 29 and 30, and is accomplished with the following sequence:

M002→M004→M006→M009→M012→R003

Figure 31:
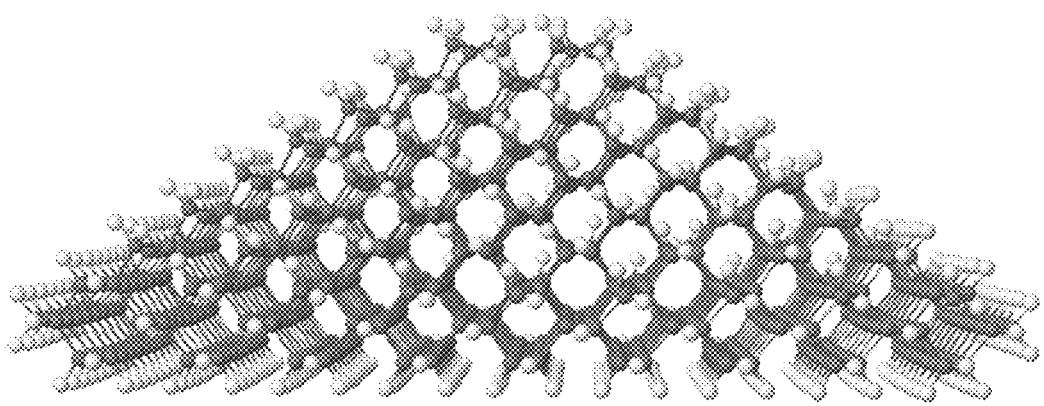
FIG. 31 shows the starting structure for an alternative manner of completing a pyramidal structure.

Capping the pyramid with Germanium is illustrated in FIGS. 31 and 32, and is accomplished with the following sequence:

M002→M004→M006→M008→M011→M014→ M009→M012→C002→C004→C006→C008

Workpiece Specification and Build Sequence Summary

The foregoing material describes how a workpiece is specified, and provides a pyramidal structure as an exemplary workpiece. The tools which would be required to build this workpiece are listed, as are all the individual reactions, and the order in which these reactions are used to build the pyramid, in two different variants.

Subsequently, we describe these and other processes at a higher level of abstraction to aid the reader in understanding the general strategy of specifying and building any workpiece.

Process Overview

To aid in the understanding of the general process of creating a workpiece, FIGS. 20 through 23 provide flow charts of various processes relating to the invention. Note that these flow charts provide only an exemplary embodiment and are in no way intended to limit the invention. Many variations on these processes are possible, and even without changing the steps involved, one might change the decision logic or loop through some processes more than once. For example, to optimally design a workpiece for manufacturability (20-2) may require an iterative process where the workpiece design is revised based on the outcome of subsequent steps or processes, such as the reaction design process described in FIG. 21.

Figure 20:
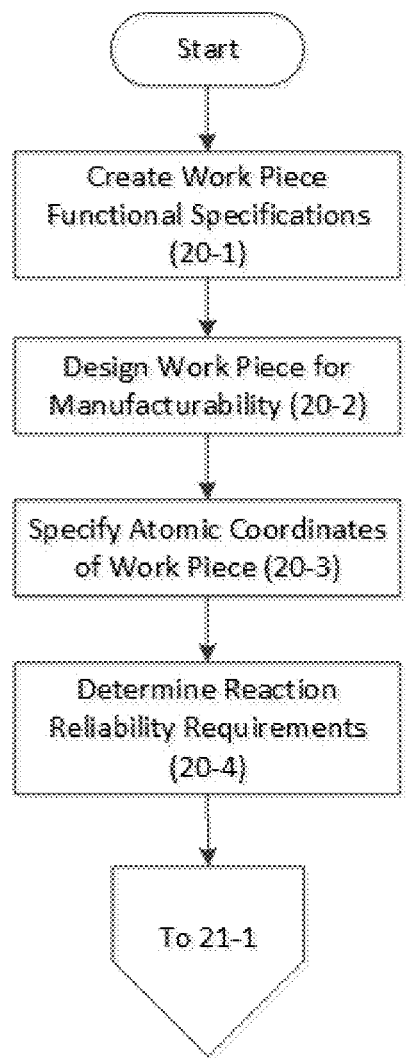
FIG. 20 shows a flow chart for workpiece specification.

The process starts in FIG. 20 at step (20-1), "Create Workpiece Functional Specifications." This step is similar to that for any traditionally-manufactured product in that product requirements must be defined before the product can be designed from an engineering perspective.

Step (20-2), "Design Workpiece for Manufacturability" also has an analog in traditional manufacturing. The product must be designed with the limitations of the manufacturing process in mind. In the case of mechanosynthesis, this means that a device should be designed with elements and geometries whose properties are understood, and for which tips and reaction sequences have been, or can be, designed.

Once the device has been designed, step (20-3) is to "Specify Atomic Coordinates of Workpiece." That is, define each atom type and its position within the structure. This step may also include determining bonding structure, as this step can be informative although technically redundant since the bonding structure may be fully specified via the atomic coordinates. This may be done in any molecular modeling or computational chemistry software with the appropriate capabilities, such as GROMACS, LAMMPS or NAMD.

Step (20-4) "Determine Reaction Reliability Requirements" involves performing an impact analysis of potential defects and the resultant establishment of reaction reliability requirements. Although the goal of mechanosynthesis is the production of atomically-precise products, unintended reactions can occur at frequencies which depend on factors including the chemical reactions being used, the tip design, the reaction trajectory, equipment capabilities and temperature. For each reaction one could analyze the most likely pathological side reactions that might occur and their impact upon the finished workpiece. For example, one could determine the impact of a feedstock atom failing to transfer, a feedstock atom bonding to a workpiece atom adjacent to the intended position, or the workpiece undergoing an unintended rearrangement. The workpiece could be simulated with each potential defect, or more general heuristics or functional testing could be used to determine the likely impact of possible errors in the workpiece.

As an example of how a defect could be insignificant in one context but not in another, consider a simple structural part such as a diamondoid beam: A small number of mistakes may not substantially affect the properties of the finished part. In such reactions, one might decide that defects under a certain number were tolerable and therefore require relatively low reaction reliability. On the other hand, if the workpiece being constructed were, for example, a single-molecule transistor that would not function correctly if crucial atoms were misplaced, one might require that such crucial reactions have high reliability.

Another option to defect impact analysis is simply to require that each reaction be reliable enough that it is statistically unlikely that the final workpiece contains any errors. This is quite feasible, as will be seen from the reaction reliability calculations presented herein. Also, the ability to correct errors may have an impact on reaction reliability requirements. If errors can be fixed, one might decide to reduce reliability requirements and simply fix errors as they occur.

Figure 21:
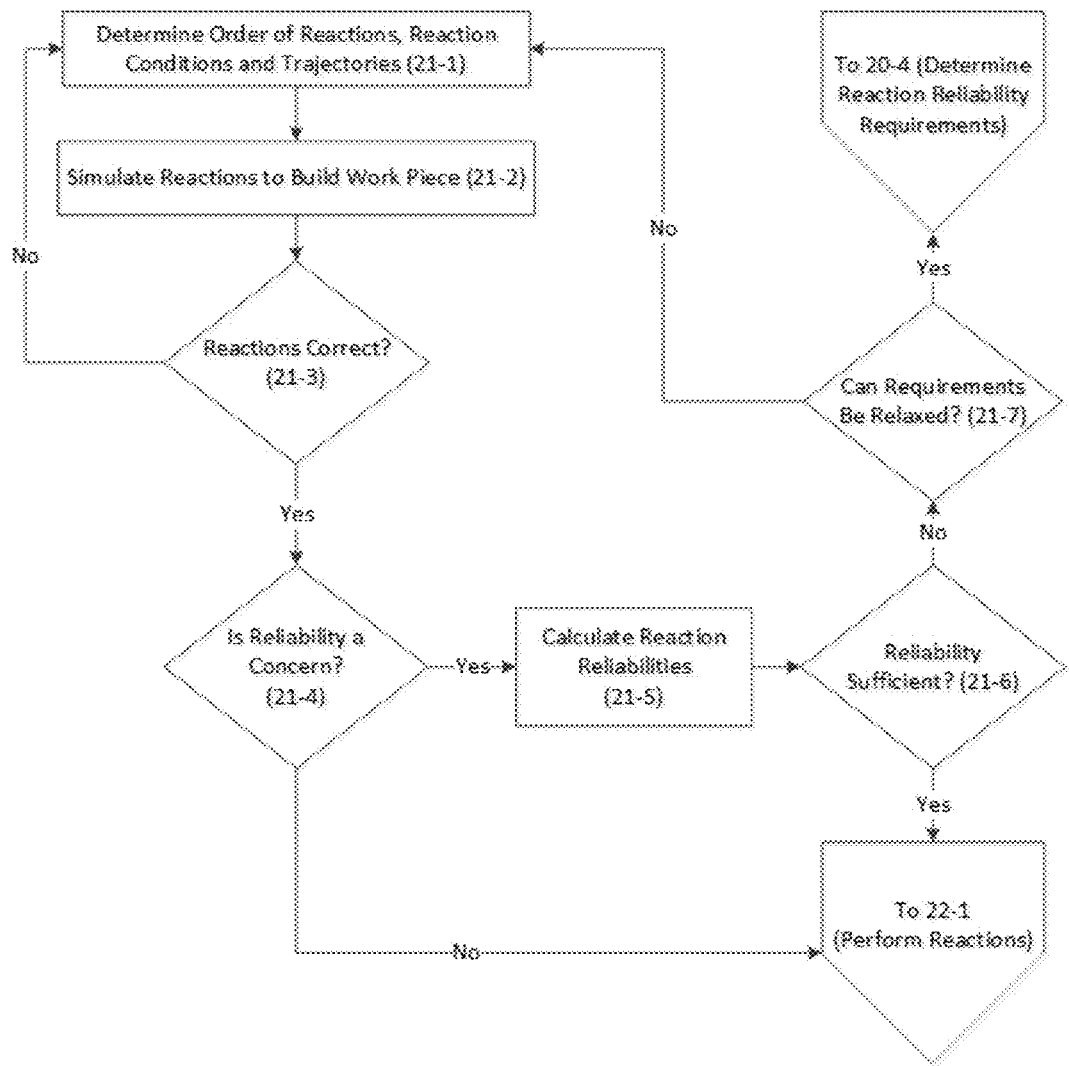
FIG. 21 shows a flow chart for mechanosynthesis reaction design.

FIG. 21 begins with step (21-1) "Determine Order of Reactions, Reaction Conditions and Trajectories." Each atom, as specified in the atomic coordinates of the workpiece, generally (but not necessarily since, for example, one could use dimers or larger molecules as feedstock) requires that a particular reaction be performed on the workpiece to deposit that atom. Abstraction reactions may also be required, as may be reactions which alter the bonding structure of the workpiece without adding or subtracting any atoms.

There may be many different reaction sequences that would permit the construction of a particular workpiece. Steric constraints will be the primary determinant of the order in which atoms are added, as a three-dimensional workpiece requires adding atoms in an order which permits access by the necessary tools to later reactions. After steric constraints have been met, the stability of the intermediate structures should be considered. For example, certain atoms, when left as radicals, might rearrange, forming undesired bonds with adjacent atoms. In addition to a logical order to the addition of atoms, other techniques can be employed to prevent undesired rearrangement. For example, hydrogen atoms can be added to radical sites to temporarily satisfy empty valances.

When a presumptive build order has been established, the reaction sequence may be simulated to determine if it works correctly (21-2). The same simulations can test reaction parameters including which tip to use, what temperature is required, and what trajectory a tip will follow. As has been previously noted, lower temperatures will favor accuracy, and unless steric issues make it obvious that a different approach is required, frequently the coaxial trajectory will enable successful reaction completion.

Note that, given that rearrangement and abstraction reactions may be required in a build sequence, workpieces may require more reactions than the number of atoms in the finished workpiece. Therefore, if the reactions are being implemented manually, for a workpiece with a high number of atoms, this obviously leads to a substantial requirement for labor. Automating the reaction steps may therefore be desirable. CAD programs can be used to specify AFM trajectories. Chen, H. (2006) "CAD-guided automated nano-assembly using atomic force microscopy-based nonrobotics." IEEE Transactions on Automation Science and Engineering 3(3): 208-217. See also, Johannes, M. S. (2006) "Automated CAD/CAM-based nanolithography using a custom atomic force microscope." IEEE Transactions on Automation Science and Engineering 3(3): 236-239. Additionally, atomic force microscopes that are programmable are commercially available, for example using LabVIEW software for control.

Based on the outcome of the simulations, a decision is reached as to whether the reactions as specified are correct (21-3). If not, the sequence is revised. If so, the process proceeds to (21-4) where a decision is made as to whether any of the calculated reactions may pose reliability concerns, for example, based on rearrangements or incorrect reactions that were seen during simulation in (21-2).

In (21-5) the reaction reliabilities can be calculated (for example, by energy barrier calculations or Monte Carlo simulations). (21-6) is a determination as to whether the proposed reaction reliabilities meet production quality needs, and, if the answer to (21-6) is no, (21-7) where requirements are reviewed to see if the build sequence restrictions can be relaxed since they were not met. From (21-7) if the answer is yes, a new iteration is started at (20-4) to determine revised reaction reliability requirements. If the answer to (21-7) is no, alternate reactions, reaction order, reaction trajectories, or reaction conditions can be simulated (21-1) to find a revised build sequence that meets the reaction reliability requirements. If the answer to (21-6) is yes, the process continues in FIG. 22, step (22-1).

Figure 22:
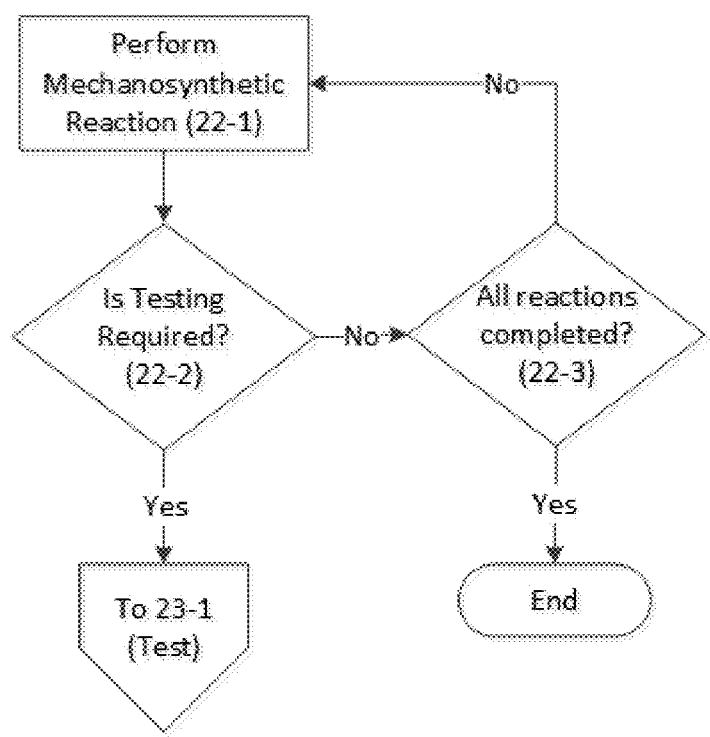
FIG. 22 shows a flow chart for carrying out mechanosynthetic reactions.

FIG. 22 is the Mechanosynthetic Reaction Process. Starting at (22-1) "Perform Mechanosynthetic Reactions," the reactions determined in the build sequence are carried out using SPM/AFM-like equipment, or other suitable equipment. This step involves, whether manually or in a computer-controlled manner, using a positionally-controlled tip to perform each mechanosynthetic reaction in the build sequence. This means picking up a feedstock atom from a presentation surface (or potentially a gaseous or liquid source of feedstock) and bonding it to the workpiece, or removing an atom from the workpiece, or changing the bonding structure of the workpiece without adding or removing an atom. This step would also encompass other reactions, including reactions not involving the workpiece, such as tip refresh or pre-reaction feedstock manipulation as may be necessary.

Step (22-2) is a decision point. If testing is not required, a decision point is reached (22-3) which depends on whether all reactions in the build sequence have been completed. If not, reactions are repeated until the answer is yes, at which point the workpiece is complete. If testing is required, the process continues in FIG. 23, starting with step (23-1).

Figure 23:
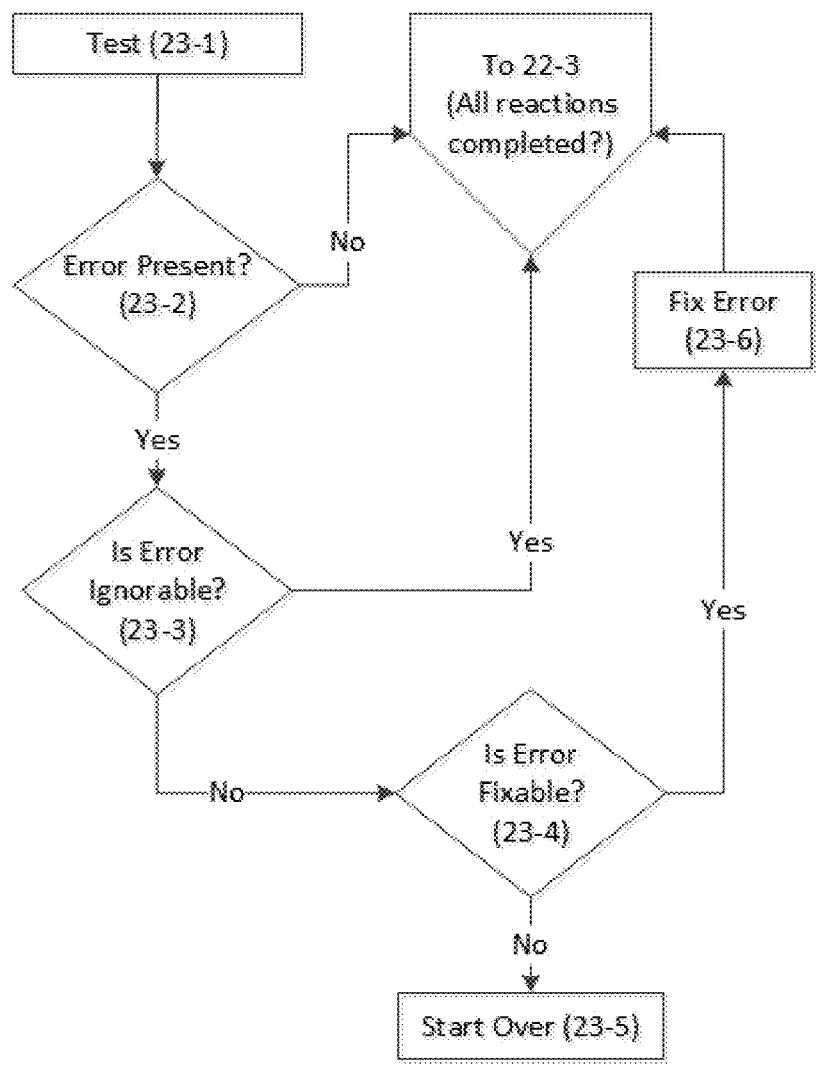
FIG. 23 shows a flow chart for a reaction testing procedure.

In FIG. 23, testing may done by, for example, scanning the surface of a workpiece using AFM or SPM-like techniques and checking to see that the expected structure is present. If no errors are found in (23-2), the process continues at (22-3). If an error is present at (23-2), a decision must be made in (23-3) as to whether the error is ignorable (e.g., not an error that would prevent the workpiece from functioning). If it is ignorable, the process again continues with (22-3), although the build sequence may require adjustment if key atoms were moved as a result of the error (not depicted). If the error is not ignorable, it must be determined if the error can be fixed (23-4). This is largely a question of whether the tools exist to reverse the reaction which caused the error so that the proper reaction can be tried again, although there could be other ways of fixing errors rather than reversing the reaction. If the error can be fixed, this is done in (23-6) and the process continues with (22-3). If the error cannot be fixed, given that it was previously determined to be a crucial error, the build sequence must be started over (23-5).

The embodiment of the process shown in FIG. 23 assumes the ability to fix errors (23-6). This is not necessarily the case, and this flow chart represents only one possible process of implementing mechanosynthesis. For example, it is possible to desire testing without the ability to fix errors, or at least not all errors, if only to know that the workpiece must be discarded and the process started anew, as in (23-5). Product requirements and process capabilities, among other considerations, will determine which steps are actually used, and in what order.

Generalizing the Exemplary Embodiments

We have described how one uses a bootstrap process to go from ultra-sharp, but atomically imprecise, tips to atomically-precise tips for the purpose of facilitating robust mechanosynthesis reactions. We note that this initial set of atomically-precise tips is capable of replicating itself, enabling the continued use of atomically-precise tips after the initial use of the bootstrap process. We have also described the use of computational chemistry techniques to design other reactions, tips that perform those reactions, and the desirable characteristics of those tips.

Additionally, we have described how one specifies a workpiece using atomic coordinates, determines a build sequence of known reliability using simulated reactions and reaction conditions, and then builds that workpiece using the reactions, tips and positional means such as an atomic force microscope, which may be computer-controlled to automate the reaction sequence process.

During the course of these descriptions, we have presented embodiments which include numerous tips (both atomically-precise and not atomically-precise) and reaction data for dozens of sets of tip/feedstock/workpiece combinations. The list of atoms for which exemplary transfer reactions have been computed spans much of the periodic table, including Al, B, Be, Br, C, Cl, F, Ge, H, Ir, Li, Mg, N, O, Na, P, S, and Si. The tip structures which are used in these transfer reactions use apical atoms including Al, B, C, Ge, N, P and Si.

There has also been presented herein a description of the reactions and build sequences used to create an exemplary complex, three-dimensional pyramidal workpiece which can serve as the basis for a Germanium Radical tool or an Adamantane Radical tool, among other uses.

It has been noted herein that the coaxial trajectory is frequently a robust way of performing mechanosynthetic reactions, but that other trajectories are possible and that varied angles can be useful to avoid steric problems when performing reactions.

It will be obvious that, due to the number of elements in the periodic table and the number of ways that such elements could be arranged, it is impossible to explicitly describe every way in which the invention could be applied or to describe every product that could be created. However, most arrangements of atoms where the reactions and structures are amenable to computational analysis could be built using the invention described. Along with the description and theory presented herein, these embodiments, data, reactions and build sequences demonstrate the wide applicability of the invention and provide substantial guidance on how to apply the concepts of the invention to cases beyond the specific embodiments presented herein. In total, the teachings herein will provide the ability to manufacture products via mechanosynthesis, means to modify a workpiece by adding or removing atoms at a specific location, bootstrap means to facilitate the creation of atomically-precise mechanosynthetic tips using non-atomically-precise tips, means of providing feedstock for reactions, methods to design mechanosynthetic reactions and reaction sequences, methods of computing reaction energetics data for designing mechanosynthetic reactions and reaction sequences, and procedures facilitating the design of workpieces, among other uses.

It should be further understood that the examples and embodiments pertaining to the systems and methods disclosed herein are not meant to limit the possible implementations of the present technology. Further, although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the Claims.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A system for building a workpiece comprising:
   a specification for a three-dimensional, atomically-precise workpiece;
   a build sequence for building said workpiece with a desired level of reliability;
   a means of providing feedstock;
   a means to position said feedstock; and
   a means to cause mechanosynthetic reactions with said feedstock, to create said workpiece,
      wherein at least some of said mechanosynthetic reactions have a calculated temperature-dependent reliability of at least about 93.8% at 77K.

2. The system of claim 1 further comprising a means for scanning said workpiece to determine if errors are present in the atomic structure of said workpiece, said means for scanning being provided by at least one of,
   said means to position when operated in a scanning mode and
   a separate means for scanning.

3. The system of claim 1 wherein said feedstock consists of at least two different chemical structures.

4. The system of claim 3 wherein said feedstock includes two or more different atoms selected from the group consisting of: Al, B, Be, Br, C, Cl, F, Ge, H, Ir, Li, Mg, N, O, Na, P, S, and Si.

5. The system of claim 1 wherein said means to cause mechanosythesis reactions performs both passivating and depassivating reactions.

6. The system of claim 1 further comprising the workpiece specified by said specification for a three-dimensional, atomically-precise workpiece; in any state of completion where said workpiece consists of at least 168 atoms.

7. A system for building a workpiece comprising:
   a specification for a three-dimensional, atomically-precise workpiece;
   a build sequence for building said workpiece with a desired level of reliability, wherein said build sequence includes mechanosythetic reactions having calculated temperature-dependent reliabilities of at least about 93.8% at 77K;
   feedstock; and
   a positioning device for engaging said feedstock and positioning said feedstock with respect to said workpiece.

8. The system of claim 7 further comprising a scanning device that scans said workpiece to determine if errors are present in the atomic structure of said workpiece, said scanning device being provided by at least one of,
   said positioning device when operated in a scanning mode and
   a separate scanning device.

9. The system of claim 7 wherein said feedstock consists of at least two different chemical structures.

10. The system of claim 9 wherein said feedstock includes two or more different atoms selected from the group consisting of: Al, B, Be, Br, C, Cl, F, Ge, H, Ir, Li, Mg, N, O, Na, P, S, and Si.

11. The system of claim 7 wherein said positioning device operates on said feedstock so as to cause both passivating and depassivating reactions to said workpiece.

12. The system of claim 7 further comprising a three-dimensional, atomically-precise workpiece built according to said build sequence by said positioning device; in any state of completion where said workpiece consists of at least 168 atoms.

13. A system for performing mechanosynthesis, comprising:
   a specification for a three-dimensional, atomically-precise workpiece;
   a build sequence for building said workpiece with a desired level of reliability;
   feedstock;
   at least one tip configured to chemically bond with said feedstock; and
   a positional device capable of moving said at least one tip so as to engage said feedstock and position said feedstock with respect to said workpiece so as to cause mechanosynthetic reactions to build said workpiece in accordance with said build sequence, wherein at least some of said mechanosynthetic reactions have a calculated temperature-dependent reliability of at least about 93.8% at 77K.

14. The system of claim 13 wherein said at least one tip further comprises at least two different tips that differ in their chemical bonding with said feedstock.

15. The system of claim 14 wherein said feedstock consists of at least two different chemical structures.

16. The system of claim 15 wherein said feedstock includes two or more different atoms selected from the group consisting of: Al, B, Be, Br, C, Cl, F, Ge, H, Ir, Li, Mg, N, O, Na, P, S, and Si.

17. The system of claim 14 wherein said at least two tips, collectively, perform both activating and passivating reactions.

18. The system of claim 13 further comprising a three-dimensional, atomically-precise workpiece built according to said build sequence by said positional device and said at least one tip; in any state of completion where said workpiece consists of at least 168 atoms.

* * * * *